US012415991B2

(12) United States Patent
Novak et al.

(10) Patent No.: US 12,415,991 B2
(45) Date of Patent: Sep. 16, 2025

(54) RECOMBINANT HEME THIOLATE OXYGENASES

(71) Applicant: bisy GmbH, Hofstätten an der Raab (AT)

(72) Inventors: Kay Domenico Novak, Graz (AT); Anton Glieder, Graz (AT); Astrid Weninger, Graz (AT); Christoph Reisinger, Graz (AT); Claudia Rinnofner, Graz (AT); Carsten Pichler, Graz (AT)

(73) Assignee: BISY GMBH, Hofstätten an der Raab (AT)

( * ) Notice: Subject to any disclaimer, the term of this patent is extended or adjusted under 35 U.S.C. 154(b) by 842 days.

(21) Appl. No.: 17/625,081

(22) PCT Filed: Jul. 6, 2020

(86) PCT No.: PCT/EP2020/069020
§ 371 (c)(1),
(2) Date: Jan. 5, 2022

(87) PCT Pub. No.: WO2021/005013
PCT Pub. Date: Jan. 14, 2021

(65) Prior Publication Data
US 2022/0282227 A1    Sep. 8, 2022

(30) Foreign Application Priority Data
Jul. 5, 2019  (EP) .................... 19184720

(51) Int. Cl.
    *C12N 9/08*       (2006.01)
    *C12N 15/81*      (2006.01)
(52) U.S. Cl.
    CPC ......... *C12N 9/0065* (2013.01); *C12N 15/815* (2013.01); *C12N 2830/00* (2013.01); *C12Y 111/02001* (2013.01)
(58) Field of Classification Search
    CPC .................................................. C12N 9/0065
    See application file for complete search history.

(56) References Cited

FOREIGN PATENT DOCUMENTS

| EP | 3382013 A1 | 10/2018 |
|---|---|---|
| WO | 2008119780 A2 | 10/2008 |
| WO | 2014090940 A1 | 6/2014 |
| WO | 2017109082 A1 | 6/2017 |

OTHER PUBLICATIONS

Babot E D et al., "Oxyfunctionalization of Aliphatic Compounds by a Recombinant Peroxygenase From Coprinopsis cinerea", Biotechnology and Bioengineering, 2013, vol. 110, No. 9, pp. 2323-2332.
Bormann S et al., "Specific oxyfunctionalisations catalysed by peroxygenases: opportunities, challenges and solutions", Catal. Sci. Technol., 2015, vol. 5, issue 4, pp. 2038-2052.
Breslmayr E. et al., "A fast and sensitive activity assay for lytic polysaccharide monooxygenase", Biotechnol Biofuels, 2018, 11:79 (13 pages).
De Vries et al., Database UniProt: A0A1L9X7H3, https://www.uniprot.org/uniprot/A0A1L9X7H3.
Faiza M et al., "New insights on unspecific peroxygenases: superfamily reclassification and evolution," BMC Evol Biol., 2019, 19:76 (19 pages).
Fischer J E et al., "Methanol Independent Expression by Pichia Pastoris Employing De-repression Technologies", J Vis Exp., 2019, 143:e58589 (6 pages).
Gröbe Glenn et al., "High-yield production of aromatic peroxygenase by the agaric fungus Marasmius rotula", AMB Express, 2011, 1:31 (11 pages).
Guan Bo et al., "Effects of co-overexpression of secretion helper factors on the secretion of a HSA fusion protein (IL2-HSA) in pichia pastoris", Yeast, 2016, vol. 33, No. 11, pp. 587-600.
Kanematsu S., Database UniProt: A0A1W2TUZ6, XP055729453,https://www.uniprot.org/uniprot/A0A1W2TUZ6, (2017), (1 page).
Kiebist J et al., "A Peroxygenase from Chaetomium globosum Catalyzes the Selective Oxygenation of Testosterone", Chembiochem., 2017, vol. 18, No. 6, pp. 563-569.
Molina-Espeja P et al., "Directed evolution of unspecific peroxygenase from Agrocybe aegerita", Appl Environ Microbiol., 2014, vol. 80, No. 11, pp. 3496-3507.
Molina-Espeja P et al., "Tandem-yeast expression system for engineering and producing unspecific peroxygenase", Enzyme Microb Technol., vol. 73-74, pp. 29-33 (2015).
Morawski B et al., "Tandem-yeast expression system for engineering and producing unspecific peroxygenase", Protein Eng., vol. 13, No. 5, pp. 377-384 (2000).
Pecyna M J et al., "Molecular characterization of aromatic peroxygenase from Agrocybe aegerita", Applied Microbiology and Biotechnology, vol. 84, No. 5, pp. 885-897 (2009).
Zámocký M et al, "Independent evolution of four heme peroxidase superfamilies", Arch Biochem Biophys, vol. 574, pp. 108-119 (2015).
Database UniProt XP055729461, (2017), (1 page).
Database UniProt XP002796392, (2012), (1 page).
Database UniProt XP002796391, (2018), (1 page).
Database UniProt: A0A1Y2VBL0, 2017, https://www.uniprot.org/uniprot/A0A1Y2VBL0.
Database UniProt, XP055731930, (2017), (1 page).
Database UniProt, Robinson, XP055729474, (2019), (1 page).
Database Geneseq XP002796379, (2018), (2 pages).
Database UniProt XP002796380, (2014), (1 page).
Database UniProt XP002796381, (2013), (2 pages).
Database UniProt XP002796382, (2015), (2 pages).
Database UniProt XP002796383, (2015), (2 pages).

(Continued)

*Primary Examiner* — Suzanne M Noakes
(74) *Attorney, Agent, or Firm* — LOZA & LOZA, LLP; Michael Fedrick

(57) ABSTRACT

The invention relates to polypeptides having peroxygenase activity and compositions comprising such polypeptides. The invention also relates to improved methods of producing such polypeptides in yeasts.

7 Claims, 24 Drawing Sheets
Specification includes a Sequence Listing.

(56) References Cited

OTHER PUBLICATIONS

Database UniProt XP002796384, (2017), (2 pages).
Database UniProt XP002796385, (2017), (1 page).
Database UniProt XP002796386, (2008), (2 pages).
Database UniProt XP002796387, (2013), (2 pages).
Database UniProt XP002796388, (2016), (1 page).
Database UniProt XP002796389, (2017), (1 page).
Database UniProt XP002796390, (2016), (1 page).
International Search Report for corresponding International Patent Application No. PCT/EP2020/069020, dated Sep. 24, 2020.
International Written Opinion for corresponding International Patent Application No. PCT/EP2020/069020, dated Sep. 24, 2020.
International Preliminary Report on Patentability for corresponding International Patent Application No. PCT/EP2020/069020, dated Oct. 8, 2021.
Office Action in corresponding European Patent Application No. 20735224.6 dated Aug. 8, 2025, 6 pages.
UniProt Database, Accession No. A0A1Y2TH07, XP093300998, Aug. 30, 2017.

Fig. 7

UPO and CPO sequences

**UPO1 mut, PaDa1 variant of *Aae*UPO 1 (SEQ ID NO:1)**

MKYFPLFPTLVYAVGVVAFPDYASLAGLSQQELDAIIPTLAREPGLPPGPLENSSAKL
VNDEAHPWKPLRPGDIRGPCPGLNTLASHGYLPRNGVATPAQIINAVQEGFNFDNQAA
IFATYAAHLVDGNLITDLLSIGRKTRLTGPDPPPPASVGGLNEHGTFEGDASMTRGDAF
FGNNHDFNETLFEQLVDYSNRFGGGKYNLTVAGELRFKRIQDSIATNPNFSFVDFRFF
TAYGETTFPANLFVDGRRDDGQLDMDAARSFFQFSRMPDDFFRAPSPRSGTGVEVVV
QAHPMQPGRNVGKINSYTVDPTSSDFSTPCLMYEKFVNITVKSLYPNPTVQLRKALNT
NLDFLFQGVAAGCTQVFPYGRD*

UPO 2 (SEQ ID NO:2)

MRGAARFAVLIALFTHAAIAFPAYGSLAGLTREQLDEILPTLEIREPGKPPGPLKDTSAK
LVNDKAHPWKPVAPADIRGPCPGLNTLASHGWLPRNGIASPSEIITAVQEGFNMDNGL
AIFVTYAAHLVDGNILTDKLSIGGKTGLTGPNPPAPAIVGGLNTHAVFEGDTSMTRGDF
FFGNNHDFNETLFDEFVDFSNRFGAGKYNLTVAGEFRWQRIQDSIATNPEFSFVSPRF
FTAYAESTFPINFFIDGRQTDGQLDLTVARGFFQNSRMPDDFHRANGTRGTEGIDLVA
EAHPIEPGSNVGGVNNYVVDPTSADFSTFCLLYENFVNKTVKGLYPNPTGALRKALNT
NLGFFFSGISDSGCTQVFPYGK*

UPO 3 (SEQ ID NO:3)

MLKLFFVQTALLALSGTTFAYPSHMSLAGLTREQLDQIVPTLTFTPPPPPPAPLNDTSA
KLVNDPAHPWQPLRAGDIRGVCPGLNTLASHGYLPRNGIVTPNQIIEAAQDGFNMDNT
LARFLAYGTFLVDGNVVTNEMSIGSKSAATGPDPPAPAIVGGLDTHAVFEGDASMTRQ
DFFGNNHDFNETLFDQFVEFSNRFGAGKYNLTVAGELRHQRIQQSIATNPNFTFVAP
RYFTAFAESAFPVDFFIDGRDSNGQLEMDVARSFFQNSRFPDGFFRPNHSVTGEGSDV
VFAAHPIEPGRNVGGVNNYVLDPTSADFTTPCLLYTNFVNETIVGLYPSPTGDLRTALN
FYLNLFFEAFDNSEGSGCTQLFPYGQD*

UPO 4 (SEQ ID NO:4)

MFSLLNFVTLALACTWSALAFPSSYTSLGGLPREELDRILPSLQYRSPGAPPGPLKFNG
TKLVNDDQHPWKPLKHGDMRGPCPGLNTLASHGYLPRNGIATPVQIINAVQEGFNME
NSVARLVTYAAHLVDGNLVTDKLSIGGKSPLTGPSPPAPANAAGLNTHALFEGDVSMT

RADAFFGDNHSFNETLFDEFTAFSNQFGAGKYNLTVAAEYRFHRIQESIATNPNFSFVS
PRFFTAYAESVFPINFFIDGRQGDGQLDLDVARGFFQNMRMPDGFHRASIPTGLEGLA
EIASVHPISPGANVNGVNTYTFDPSSADFTTFCLLYVNFVNQTVRSLYPEPTGNLKKAL
KKNLEFLYGPFSDQCSQVFPYGKDN*

UPO 5 (SEQ ID NO:5)

MARLTFLVAVALALSSTTVAFPSYGSLAGLSEAELDRIIPLLEARDACPPPGPLKNTSTK
LVNDKDHPWKPLRDGDIRGPCPGLNTLASHGWLPRNGVATPAQIINAVQEGFNMGN
DLAVFVTYAAHLVDGNQVTDLLSIGGKTPQTGPDPPQPAIVGGLDTHAVFEGDASMTR
GDAFFGDNHSFNETQFDEFSAFSNKFGGGYYNLSVAAEFRWQRIQESIATNPNFSFISP
RYFTAYAESVFPLVFFVDGRVSDGRLSLPNARGFFQNSQMPTDFFRPNQSIGLDVIGD
GISAIASAHPIAPGKNEGVGNYVLDPTSADFDHFCLLYINFVNQTVKSLYPNPTGVLRD
ALKRNLDNFYSPLNGSDCVQIFPYGK*

UPO 6 (SEQ ID NO:6)

MVQFTVILSLLLATGKALAFPQYGSLAGLSERELEDILPRLHAVKPPPPPGPLNDTSTK
LVNNPAHPFLPQRNGDMRGPCPGLNTLASHGYLPRNGIATPAQIINAVQEGFNMGND
LAVFVTYAAFLVDGNQVTNLLSIGGKSSLTGPDPPKPAIVGGLDTHAVFEGDASMTRG
DAFFGDNHSFKENQFDEFIAFSNKFGGGKYNLTVASEFRWQRIQESTATNPNFSFISPR
YFTAYAESTFPITFFVDGRNEDGALSLDVARGFFQDSRMPNGFFRANQSIGLDIIGSLID
FIFEPHPIQPGGNQGRVNSYTVDPNSANFSQFCQLYQDFVNNTVKGLYPNPQGVLRD
NLNTNLGFFFSPLQGSGCPQVFPFGQ*

UPO 7 (SEQ ID NO:7)

MRFFSHLSIIPLLSLHGVLAFPSYGTLAGLSRSELEAILPTLKPGVPESPPGPLNDTSAK
LVNDKKHPWKPAGKKDIRGPCPGLNTLASHGWLPRDGVATPAQIVNAVQEGFNMGN
DLAVFVTYAAHLVDGNLITNLLSIGGKTDRTGPNPPPPAIVGGLNTHAVFEGDASTTRA
DFFFGDNHSFNETLFDELTAFSNKFGGGFYNLSVAAEFRFQRIQDSIATNPQFDFISPR
YFTAYAESIFPLTFFIDGRDKSLHLDMNVARGFFQNSRFPDGFFRSNTSITLDVIGGGID
YIFSKHPVPPGSNNGTVNSYTPNPNSADFTQFCKLYTDFVNITIRGLYPNAKGALLTAL
NKNLEYFYSPLVGSGCPQVPPFV*

Fig. 7 continued

UPO 8 (SEQ ID NO:8)

MARVFFAIAALLLAAKDVVSFPNYASLAGLSERELDEIIPQLTVRTLEKPPGQMKNTLT
KLVNDPAHPWIAPAPDDQRDPCPGLNTLANHGYLPRDGIATPAQIVNAVQEGFNMAN
DIAVFVTYAAHLVDGNLLTDLLSIGGKSAKTGPNPPSPAIVGGLDTHAVFEGDASTTRG
DAFFGDNHSFNESLFDELTAFSNKFGAGFYNLSVATEFRFQRIQDSIATNPQFSLISPR
YYTAYAESVFPVAFFVDGRETNGSLNMTVARGFFQDGRMPNDFFRSNISWGLDLIGE
GIGFIFTPHPIEPGTNNGTLNSYTLDPNSADFSDFCKLYTDFVNVTVRGLYPNATGPLL
NALNQNLDFFFGPLGDQGCTQVPAFV*

UPO 9 (SEQ ID NO:9)

MKLNIFSTTLAIGLVSAGAHYHQQDVVANGTEGVWIAPTDTDYRGPCPMMNTLANHG
FLPRDGKNLTEYNVVKGLNDGLNFNKSLATIMFQQAIPASPAYPNATFFTLNDLNRHN
VLEHDGSISRSDAYYGNNYIFNQTIFDTTKAYWPSETLTAQHLIDGKMFRQIVSRSTNP
NYTFSATTQQFSLGEMAAPIVAFGDKYVVTANRTLVESWIENERLPTELGWRKPVEEIL
LSDITYVTEVLGNLTSLYSTVIITPNPDSLAKRQMGHWGQSI*

UPO 10 (SEQ ID NO:10)

MKTTTLLLCLAAALTQTYAFPQQGAPHPLPWSPPGPNDVRAPCPMLNTLANHGYLPH
NGKDITERHTINALYNALGIEEELAIYLHQEAVTTNPAPNATTFSLNDLSRHDILEHDAS
LSRQDAYFGDNHDFNQTIFDETRSYWTSPIIDVKQAAVSRQARVNTSMATNPNYTMS
ELGDSFSYGETAAYIIVLGDKEKGLVNRSRVEYLFENERLPLDLGWSRAKENITFDDLS
TMLQRIINATGGEMDFRATIALPRLVYIYYEEA*

UPO 11 (SEQ ID NO:11)

MKTTTLLFLVGALTQTHAFPQQGVPHPLPWSPPGPNDVRAPCPMLNTLANHGFLPH
NGKNITQQHTINALYNALGIDAELATYLHQEAVTTNPVPNATTFSLNDLSRHDILEHDA
SLSRQDAFFGDNHDFNQTIFNQTRSYWTSPIIDVKQAALARQARVNTSMATNPNYTM
SELGDAFSYGETAAYIIVLGDKEAGLVNRSRVEYLFENERLPVELGWSRARENITFDDLS
TMLNKIINATGGESEFERELAKRGGVHVGWR*

Fig. 7 continued

UPO 12 (SEQ ID NO:12)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGDTRCPYGYH*

UPO 13 (SEQ ID NO:13)

MKTLFLLTLAAFTPVFAGFDTWAPPGPYDVRAPCPMLNTLANHGFLPHDGHEITREQ
TENALFDALHIDKMLGSSLFDFAMTTNPVANSTTFSLNDLGNHNVLEHDASLSRSDA
YFGNTLTFNQTVFDETKSYWTDETVTIEMASNARLARIKTSNATNPTYSMSELGNGFT
KGESAAYVVIFGDKISGTVPRAWVEWLFEIALKTQPSTPSIKPTQTPSSPTRLLLKRLGR
QLMLIVPRPIRLRVLRNTPPLRLITKNKPREMAPNLLILAVHKRATSMQKR*

UPO 14 (SEQ ID NO:14)

MRTSLLPALAAVSPVLAGFDTWAPPGPYDVRGPCPMLNTLTNHGFFPHDGQDIDRET
TENALFDALHVNKTLASFLRADAYHGSVLAFNHTIFEETKSYWTDETVTLKMAADARY
YRIKSSQATNPTYQMSELGDAFTYGESAAYVVLFGDKESQTVPRSWVEWLFEKEQLP
QHLGWKRPATSFELNDLDKFMALIQNYTQEIEEPSCESRKQRRKPRGPSHFGF*

UPO 15 (SEQ ID NO:15)

MAKFSTLFAFSALAIQAIALPQYRSLAGLSERELEGILPRLNVVTPPPSPPGPPNDTSVK
LVNDAAHPFMPLQDGDIRGPCPGLNTLASHGYLPRNGIATPAQIINAVQDGFSMDNGL
ATLLAYATMLVDGNPLTNLMSIGGKSPLTGMDPPQPAIVGGLDTHAVFEGDASMTRA
DFFFGDNHSFNQTLFNQFANFSNQFGDGNYNLTTAEEYRFFRIQQSIAENPQFSFISPR
FFTAYFESAFPLVFFVDGRQADGQLSVENATSFFRDMQFPDDFHRADGSQTADLVNN
AATAIFSAHPMQPGGNNGTVNSYTFDPNSANFTEGCKLYTDFVNNVVVPLYPTPQGA
LKVNLNANLGFLFSTFSNCTQVFPYGQ*

Fig. 7 continued

UPO 16 (SEQ ID NO:16)

MAKFSTLLALSVLAIQAVAFPQHQPLAGLTERELEDLLPRFKPVVPPPPPGPPKDTSVK
LVNDKDHPYEPLRKGDIRGPCPGLNTLASHGYLPRNGVVTPAQIINAVQDGFGMDNEL
AILLAYSTMLTDGNVVTNLMSIGQKTPLTGPDPPAPAIVGGLNTHGTFEGDAGLTRAD
FFFGDNHSFNQTLFNEFVEFSNKFGGGVYNQTVAAEYRFFRIQQSTAENPTFTFVTPR
FVTAYRESVFPFIFFVDGRKADGQLSMKDAFGFFNESRMPDGFHRADGSKTADLVGN
ASDAIFAAHPVQPGANAGKVNTYTPDPNSPTDDCGLYETFVNLMVKQYPNPQGVLRT
NLNLNLGFFFQGFPGCTQLFPFGQ*

UPO 17 (SEQ ID NO:17)

MLGIRLVSLLAFTGSALAELDFSKWKTRQPGELRAPCPAMNSLANHGFIQRDGKNITV
EGLTPVLKEVFHLSHELAFTVSQLGLFTALDPSKGVFTLQDLTDRHNVFEHDASLSRE
DAKFGGDQSVLHKGQFQKFMDHFKGEKYISFEAAAKARYAMVQDSRKRNPDFTYDV
THRITSYGETIKYLRTIVEPSTGKCPVDWIKILFEQERLPYNEGWRPPTNELSGFSLASE
VLELALITPEKLPVDECLGKGKGKGNCKRRRSYLGI*

UPO 18 (SEQ ID NO:18)

MNPFLKLAVLALVTAPLAGAFPSHRSLGGLSSEQLDRIFPTLKVAPPEGPPPPQDDTS
TRLVDDADHPFMPAGPNDMRGPCPGLNTLASHGYLPRNGIATPAQVINATMQGFNM
EFSLAKFVTYAAFLVDGNPITNLMSIGGKSDLTGEDPPDPATVGGLNTHAVFEGDASM
TRADAFFGDNHSFNQTLWDGFVDFSNRFGAGKYNLTVATELRIQRIQDSIATNPQFSF
VSPRFITAYAESTFPINFFIDGRQQDGQLDLDAAISFFRDMRYPSGFFRAPKPMGVEGIE
TIIAAHPIPAGANNGAVNTYTPDPHSGDFNSFCTVYTNFVNETIRGLYPSPTGILKDSLN
RNLDFLHDFVSGCPQIFPWGR*

CPO 19 (SEQ ID NO:19)

MFSKVLPFVGAVAALPHSVRQEPGSGIGYPYDNNTLPYVAPGPTDSRAPCPALNALAN
HGYIPHDGRAISRETLQNAFLNHMGIANSVIELALTNAFVVCEYVTGSDCGDSLVNLTL
LAEPHAFEHDHSFSRKDYKQGVANSNDFIDNRNFDAETFQTSLDVVAGKTHFDYADM
NEIRLQRESLSNELDFPGWFTESKPIQNVESGFIFALVSDFNLPDNDENPLVRIDWWKY
WFTNESFPYHLGWHPPSPAREIEFVTSASSAVLAASVTSTPSSLPSGAIGPGAEAVPLS
FASTMTPFLLATNAPYYAQDPTLRPQRQA*

Fig. 7 continued

CPO 20 (SEQ ID NO:20)

MFSKILPLVGVAAALPHWLQLRQEPNSGIGYPYDNHTKPYVHPGPHDSRAPCPALNA
LANHGYIPHNGRAITKENLQNAFLEHMGIGNSVIALALTNAFVVCEYVTGQDCGDTLVN
LTLLSEPHAFEHDHSFSRKDYKQGVSNFNEIVDNRNFDLSTFETSLDVVAGQTHFGYA
EMNQIRLQRESLSNEADFPGWFTESKPIQEVEAGFIFALVSDFNLPDNDENPLVRVDW
WKYWFINESFPYHLGWHPPTPAREIEFVTSASSAILAAAVTSTPSSLPSGAIGPGAEAVP
LSFASTMTPFLLATDIPYFAHPTLGPNDKREAAPAPAATTSTATFKNPYLEPIGTQDIK
NQQAYVSSKAAAMSSAMAVNKARSL*

UPO 21 (SEQ ID NO:21)

MKYFPLFPTLVFAARVVAFPAYASLAGLSQQELDAIIPTLEAREPGLPPGPLENSSAKLV
NDEAHPWKPLRPGDIRGPCPGLNTLASHGYLPRNGVATPVQIINAVQEGLNFDNQAAV
FATYAAHLVDGNLITDLLSIGRKTRLTGPDPPPPASVGGLNEHGTFEGDASMTRGDAF
FGNNHDFNETLFEQLVDYSNRFGGGKYNLTVAGELRFKRIQDSIATNPNFSFVDFRFF
TAYGETTFPANLFVDGRRDDGQLDMDAARSFFQFSRMPDDFFRAPSPRSGTGVEVVI
QAHPMQPGRNVGKINSYTVDPTSSDFSTPCLMYEKFVNITVKSLYPNPTVHVRKALNT
NLDFFFQGVAAGCTQVFPYGRD

UPO22 (SEQ ID NO:22)

MKLVYLSSAVAFGSAIADTAPWEGPGPNDVRGPCPMLNTLANHGFLPHDGKNIHVNK
TVDALSSALNIDPELGSFLHSFAVTANPQPNATWWNLDHLSRHNILEHDASLSRQDAY
FGAPDVFNEAVFNQTKSYWTGDVITLQMAANARLARLMTSNLTNPEYSMSDLGSSFS
IGESVAYVAILGSKETRTVPKAYVEYLFEKERLPYELGFKKAETPMTETDLGNLMDELIS
LQHFPQSPGKIAKRSERPSEKRAEKRCPFH

UPO23 (SEQ ID NO:23)

MKTATLLFLAAGLTQTQAFPSQGAAPHPLPWSPPGPNDVRAPCPMLNTLANHGYLP
HNGKNITEQHTINALYNALGIDAELSAFLHQEAVTTNPTPNATTFSLNDLSRHDILEHD
ASLSRQDAYFGDNHDFNQTIFDETRSYWTSPIIDVKQAALSRQARVNTSMATNPNYT
MSELGASFSYGETAAYIIVLGDKENGLVNRSRVEYLFENERLPLDLGWTRAKENITFDD
LRTMLNRIVNATGGESEFDRELAKRGGVHVGRWRGY

Fig. 7 continued

UPO24 (SEQ ID NO:24)

MKTTTLLCLAAALTQTYAFPQQGAPHPLPWSPPGPNDVRAPCPMLNTLANHGYLPH
NGKDITERHTINALYNALGIEEELAIYLHQEAVTTNPAPNATTFSLNDLSRHDILEHDAS
LSRQDAYFGDNHDFNQTIFDETRSYWTSPIIDVKQAAVSRQARVNTSMATNPNYTMS
ELGDSFSYGETAAYIIVLGDKEKGLVNRSRVEYLFENERLPLDLGWSRAKENITFDDLS
TMLQRIINATGGESEFDRELAKRGGVHVGSWRG

UPO25 (SEQ ID NO:25)

MKTTPLLFFAAGLAQTHAFPSQGGAPHPLPWSPPGPNDVRAPCPMLNTLANHGYLP
HNGKDITEQHTINALYNALGIDAELATYLHQEAVTTNPAPNATTFSLNDLSRHDILEHD
ASLSRQDAFFGDNHDFNQTIFDETRSYWTSPIIDVMQAALSRQARVDTSMATNPNYT
MSELGASFSYGETAAYIIVLGDKENGLVNRSRVEYLFENERLPLDLGWTRAKENITFDD
LSTMLNRIVNATGGESEFDRELAKRGGVHVGKWRGY

UPO12_23E12 (SEQ ID NO:30)

MKSLSFSLALGFGSTLVYSAPSP<u>F</u>SGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGDTRCPYGYH

UPO12_11G3 (SEQ ID NO:31)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDII<u>Y</u>VQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGDTRCPYGYH

Fig. 7 continued

UPO12_8G3 (SEQ ID NO:32)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGDTRSPYGYH

UPO12_11H12 (SEQ ID NO:33)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGDTR

UPO12_13A2 (SEQ ID NO:34)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGNTRCPYGYH

UPO12_18G3 (SEQ ID NO:35)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKVEKRGITRCPYGYH

Fig. 7 continued

UPO12_20H11 (SEQ ID NO:36)

MKSLSFSLALGFGSTLVYSAPSPSSGWQAPGPNDVRAPCPMLNTLANHGFLPHDGK
GITVNKTIDALGSALNIDANLSTLLFGFAATTNPQPNATFFDLDHLSRHNILEHDASLSR
QDSYFGPADVFNEAVFNQTKSFWTGDIIDVQMAANARIVRLLTSNLTNPEYSLSDLGS
AFSIGESAAYIGILGDKKSATVPKSWVEYLFENERLPYELGFKRPNDPFTTDDLGDLST
QIINAQHFPQSPGKV

POX27_OTB02684.1 [Hypoxylon sp. CI-4A] (SEQ ID NO:37)

MKSVQLSALIAFGAKAVYSFPSANAPWSGPGTDDVRGPCPMLNTLANHGFLPHSGKG
ITVNKTIDALNAGLNMEADLAALLFDFAVTTNPTPNASYFDLDHLTRHNILEHDASISR
QDSYFGRADILNEAVFNQTKSYWTGELVDIQMAANARVARLMTSNLTNPEYSLSDTG
SVFSIGESAAYVGILGDKVSGTVPKTWLIYLFEQERLPYELGFKRPVDPFTEDDLFNMS
EAIRDAQHFPQDIGKVTKRGNKARCPHGYCIEVL

POX30_GAP92448.1 [Rosellinia necatrix] (SEQ ID NO:38)

MKLTTLLFPAVVLGAACPYGTFKPEEPTDTRGVCPMLNALANHGFLPRDGRNINENQ
TVTALNNALNLTPDFGRFLFTAGRLSNPKPNSTTFDLNHLDRHNLFEHDGSLSRQDA
HFGQWSRFNQTVWNWTMQYWTGDILDVQMVANGRAQRHTRSNLTNPDYALSVVGY
DFSVAENAALLSIIGDKVTQTCPKKFVDYLFVNEELPYSVGWKKSELPIALEDLIRTFRDI
ELATAFPAPPPPDNSGEIFA

POX32_OTB09996.1 [Daldinia sp. EC12] (SEQ ID NO:39)

MKLTFMSSVVTLGSAVAAYPTSWEAPGPNDVRGPCPMLNTLANHGFLPHDGKNINV
NNTAEALSKGLNLAWELGVDLHDFAVMANPQPNATTFDLDHLSRHNVLEHDGSLSR
QDAHFGPPDVFNEAVFNQTVSYWTGDVVTMQMAANARLARLMTSNLTNPEYSLSDL
GSGFSIGESVVYLLVLGNKDTAEAPKNYLEYWFRNERLPYELGWERPNVIMTGDDLG
NAMDKLVTLQHFPQSPGKITSDPEKASAKLAGKRHLFH

POX34_RYP66388.1 [Monosporascus sp. CRB-8-3] (SEQ ID NO:40)

MKFELAATILAAGTASAFRLKARDTYDWHPPAYGDVRGPCPMLNTLANHGYLPRNGK
DITENRTIEALGTALSIDSELAQLLFEQAITTNPAPNATTFSLNDLVRHNILEHDASLSRV
DFYFGNPQPFNQTVFAQTRSYWTTPIIDVQQAANARWARVETSNATNPNFTLSTLGER
FSYGESAAYIVILGNKITGTVPRDWVEYLFENERLPLEIGWTRRTGSITRNDLEDVMQQI
YAATPNNATTNSWRGNPRALHMAVRASA

Fig. 7 continued

POX39 XP_020060613.1 [Aspergillus aculeatus ATCC 16872] (SEQ ID NO:41)
MRYFVLACAPLLYAVTLAFPRADYVSEGKLPAGHPPLDWKPAGLGDARAPCPMLNTL
ANHGYLPHDGKDITKAHTIAALHSALNIDRELAQYLFQEALTTNPAANATTFSLNDLSR
HNILEHDASLSRLDYYFGDNHDFNQAIFDQTRQHWPDPIITVQAAANAREARVRTSNA
TNPTFTLSELGTAFGYGETAAYIIILGNKTSGLVDRSWVEYLFENERLPVELGWTRHEE
AVSMDDLEGMMQEVINATGHAEEVKRELVRRGDLHVGRRA

|  |  | Peroxygenase | Peroxidase | Peroxygenase : Peroxidase |
|---|---|---|---|---|
|  |  | Naphthalene -Fast Blue Assay | ABTS Assay |  |
| Construct | Clone | ΔABS(520nm)/min/μl | ΔABS(405nm)/min/μl | Ratio between Activities |
| UPO 12 | 12-C0 | 2,07 | 4,43 | 0,47 |
| UPO 12 | 12-A0 | 2,05 | 4,59 | 0,45 |
| UPO 11 | 11-A0 | 1,98 | 4,35 | 0,45 |
| UPO 11 | 11-C0 | 1,97 | 4,14 | 0,48 |
| UPO 11 | 11-B0 | 1,85 | 4,27 | 0,43 |
| PaDa1 | 1-B0 | 1,05 | 3,86 | 0,27 |
| PaDa1 | 1-C0 | 0,94 | 3,84 | 0,24 |
| PaDa1 | 1-A0 | 0,81 | 4,45 | 0,18 |
| UPO 5 | 5-A0 | 0,63 | 0,04 | 15,83 |
| UPO 2 | 2-A0 | 0,3 | 0,05 | 6,36 |
| UPO 2 | 2-B0 | 0,28 | 0,03 | 10,63 |
| UPO 4 | 4-B0 | 0,09 | 0,01 | 7 |
| UPO 4 | 4-A0 | 0,08 | 0,03 | 3,13 |
| UPO 16 | 16-A0 | 0,03 | 0,01 | 2,25 |
| UPO 15 | 15-A0 | 0,02 | 0,05 | 0,43 |
| UPO 17 | 17-A0 | 0,01 | 23,29 | 0 |
| UPO 17 | 17-B0 | 0,01 | 19,45 | 0 |
| UPO 17 | 17-C0 | 0,01 | 19,01 | 0 |

Fig. 12

Alignment UPO12 variants to UPO12 wild type ("POX12")

```
POX12_23E12      MKSLSFSLALGFGSTLVYSAPSPFSGWQAPGPNDVRAPCPMLNTLANHGFLPHDGKGITV    60
POX12_11G3       MKSLSFSLALGFGSTLVYSAPSPSSGWQAPGPNDVRAPCPMLNTLANHGFLPHDGKGITV    60
POX12_20H11      MKSLSFSLALGFGSTLVYSAPSPSSGWQAPGPNDVRAPCPMLNTLANHGFLPHDGKGITV    60
POX12_18G3       MKSLSFSLALGFGSTLVYSAPSPSSGWQAPGPNDVRAPCPMLNTLANHGFLPHDGKGITV    60
POX12_13A2       MKSLSFSLALGFGSTLVYSAPSPSSGWQAPGPNDVRAPCPMLNTLANHGFLPHDGKGITV    60
POX12            MKSLSFSLALGFGSTLVYSAPSPSSGWQAPGPNDVRAPCPMLNTLANHGFLPHDGKGITV    60
POX12_8G3        MKSLSFSLALGFGSTLVYSAPSPSSGWQAPGPNDVRAPCPMLNTLANHGFLPHDGKGITV    60
POX12_11H12      MKSLSFSLALGFGSTLVYSAPSPSSGWQAPGPNDVRAPCPMLNTLANHGFLPHDGKGITV    60
                 ********************** * ***********************************

POX12_23E12      NKTIDALGSALNIDANLSTLLFGFAATTNPQPNATFFDLDHLSRHNILEHDASLSRQDSY   120
POX12_11G3       NKTIDALGSALNIDANLSTLLFGFAATTNPQPNATFFDLDHLSRHNILEHDASLSRQDSY   120
POX12_20H11      NKTIDALGSALNIDANLSTLLFGFAATTNPQPNATFFDLDHLSRHNILEHDASLSRQDSY   120
POX12_18G3       NKTIDALGSALNIDANLSTLLFGFAATTNPQPNATFFDLDHLSRHNILEHDASLSRQDSY   120
POX12_13A2       NKTIDALGSALNIDANLSTLLFGFAATTNPQPNATFFDLDHLSRHNILEHDASLSRQDSY   120
POX12            NKTIDALGSALNIDANLSTLLFGFAATTNPQPNATFFDLDHLSRHNILEHDASLSRQDSY   120
POX12_8G3        NKTIDALGSALNIDANLSTLLFGFAATTNPQPNATFFDLDHLSRHNILEHDASLSRQDSY   120
POX12_11H12      NKTIDALGSALNIDANLSTLLFGFAATTNPQPNATFFDLDHLSRHNILEHDASLSRQDSY   120
                 ***************************** ******************************

POX12_23E12      FGPADVFNEAVFNQTKSFWTGDIIDVQMAANARIVRLLTSNLTNPEYSLSDLGSAFSIGE   180
POX12_11G3       FGPADVFNEAVFNQTKSFWTGDIIYVQMAANARIVRLLTSNLTNPEYSLSDLGSAFSIGE   180
POX12_20H11      FGPADVFNEAVFNQTKSFWTGDIIDVQMAANARIVRLLTSNLTNPEYSLSDLGSAFSIGE   180
POX12_18G3       FGPADVFNEAVFNQTKSFWTGDIIDVQMAANARIVRLLTSNLTNPEYSLSDLGSAFSIGE   180
POX12_13A2       FGPADVFNEAVFNQTKSFWTGDIIDVQMAANARIVRLLTSNLTNPEYSLSDLGSAFSIGE   180
POX12            FGPADVFNEAVFNQTKSFWTGDIIDVQMAANARIVRLLTSNLTNPEYSLSDLGSAFSIGE   180
POX12_8G3        FGPADVFNEAVFNQTKSFWTGDIIDVQMAANARIVRLLTSNLTNPEYSLSDLGSAFSIGE   180
POX12_11H12      FGPADVFNEAVFNQTKSFWTGDIIDVQMAANARIVRLLTSNLTNPEYSLSDLGSAFSIGE   180
                 *********************** ************************************

POX12_23E12      SAAYIGILGDKKSATVPKSWVEYLFENERLPYELGFKRPNDPFTTDDLGDLSTQIINAQH   240
POX12_11G3       SAAYIGILGDKKSATVPKSWVEYLFENERLPYELGFKRPNDPFTTDDLGDLSTQIINAQH   240
POX12_20H11      SAAYIGILGDKKSATVPKSWVEYLFENERLPYELGFKRPNDPFTTDDLGDLSTQIINAQH   240
POX12_18G3       SAAYIGILGDKKSATVPKSWVEYLFENERLPYELGFKRPNDPFTTDDLGDLSTQIINAQH   240
POX12_13A2       SAAYIGILGDKKSATVPKSWVEYLFENERLPYELGFKRPNDPFTTDDLGDLSTQIINAQH   240
POX12            SAAYIGILGDKKSATVPKSWVEYLFENERLPYELGFKRPNDPFTTDDLGDLSTQIINAQH   240
POX12_8G3        SAAYIGILGDKKSATVPKSWVEYLFENERLPYELGFKRPNDPFTTDDLGDLSTQIINAQH   240
POX12_11H12      SAAYIGILGDKKSATVPKSWVEYLFENERLPYELGFKRPNDPFTTDDLGDLSTQIINAQH   240
                 ************************************************************

POX12_23E12      FPQSPGKVEKRGDTRCPYGYH   261
POX12_11G3       FPQSPGKVEKRGDTRCPYGYH   261
POX12_20H11      FPQSPGKVXKRGDTRCPYGYH   261
POX12_18G3       FPQSPGKVEKRGITRCPYGYH   261
POX12_13A2       FPQSPGKVEKRGNTRCPYGYH   261
POX12            FPQSPGKVEKRGDTRCPYGYH   261
POX12_8G3        FPQSPGKVEKRGDTRSPYGYH   261
POX12_11H12      FPQSPGKVEKRGDTRXPYGYH   261
                 ******** *** ** *** *

POX 23E12   = SEQ ID NO:30
POX12 11G3  = SEQ ID NO:31
POX12 20H11 = SEQ ID NO:36
POX12 18G3  = SEQ ID NO:35
POX12 13A2  = SEQ ID NO:34
POX12       = SEQ ID NO:12
POX12 8G3   = SEQ ID NO:32
POX12 11H12 = SEQ ID NO:33
```

Fig. 13

Clustalw Alignment (UPO12 (SEQ ID NO:12) and UPO27 (SEQ ID NO:37), full length protein sequence)

```
UPO12_(SEQ      MKSLSFSLALGFGSTLVYSAPSPSSGWQAPGPNDVRAPCPMLNTLANHGFLPHDGKGITV     60
UPO27_(SEQ      MKSVQLSALIAFGAKAVYSFPSANAPWSGPGTDDVRGPCPMLNTLANHGFLPHSGKGITV     60
                ***:..*   :.**:. *** **  .: *..** :***.******************.******

UPO12_(SEQ      NKTIDALGSALNIDANLSTLLFGFAATTNPQPNATFFDLDHLSRHNILEHDASLSRQDSY    120
UPO27_(SEQ      NKTIDALNAGLNMEADLAALLFDFAVTTNPTPNASYFDLDHLTRHNILEHDASISRQDSY    120
                *******.:..**::*:*::***.**.**** ***.:*****.*************.:******

UPO12_(SEQ      FGPADVFNEAVFNQTKSFWTGDIIDVQMAANARIVRLLTSNLTNPEYSLSDLGSAFSIGE    180
UPO27_(SEQ      FGRADILNEAVFNQTKSYWTGELVDIQMAANARVARLMTSNLTNPEYSLSDTGSVFSIGE    180
                ** **:.:*********:***:::*:*******:.**:*************.**.*****

UPO12_(SEQ      SAAYIGILGDKKSATVPKSWVEYLFENERLPYELGFKRPNDPFTTDDLGDLSTQIINAQH    240
UPO27_(SEQ      SAAYVGILGDKVSGTVPKTWLIYLFEQERLPYELGFKRPVDPFTEDDLFNMSEAIRDAQH    240
                ****:****** *.****:* ****:************ *** ***  ::*   * :***

UPO12_(SEQ      FPQSPGKVEKRGD-TRCPYGYH*---    261
UPO27_(SEQ      FPQDIGKVTKRGNKARCPHGYCIEVL    266
                ***. *** ***:  :***:**
```

Percent Identity Matrix - created by Clustal2.1

```
    1: UPO12__SEQ   100.00    72.41
    2: UPO27__SEQ    72.41   100.00
```

Clustalw Alignment (UPO12 (SEQ I DNO:12) and UPO27 (SEQ ID NO:37), without predicted signal sequence)

```
UPO12      APSPSSGWQAPGPNDVRAPCPMLNTLANHGFLPHDGKGITVNKTIDALGSALNIDANLST     60
UPO27      FPSANAPWSGPGTDDVRGPCPMLNTLANHGFLPHSGKGITVNKTIDALNAGLNMEADLAA     60
           **  .:  *..**  :***.******************.***********.:..**::*::

UPO12      LLFGFAATTNPQPNATFFDLDHLSRHNILEHDASLSRQDSYFGPADVFNEAVFNQTKSFW    120
UPO27      LLFDFAVTTNPTPNASYFDLDHLTRHNILEHDASISRQDSYFGRADILNEAVFNQTKSYW    120
           ***.**.**** ***.:******.*********:******** **:.:*********.*

UPO12      TGDIIDVQMAANARIVRLLTSNLTNPEYSLSDLGSAFSIGESAAYIGILGDKKSATVPKS    180
UPO27      TGELVDIQMAANARVARLMTSNLTNPEYSLSDTGSVFSIGESAAYVGILGDKVSGTVPKT    180
           **::.:*:*******:.**:************ **.*********:****** *.****:

UPO12      WVEYLFENERLPYELGFKRPNDPFTTDDLGDLSTQIINAQHFPQSPGKVEKRGD-TRCPY    239
UPO27      WLIYLFEQERLPYELGFKRPVDPFTEDDLFNMSEAIRDAQHFPQDIGKVTKRGNKARCPH    240
           *: ****:************ *** ***  ::*   * :******. *** ***:  :***

UPO12      GYH*---    242
UPO27      GYCIEVL    247
           **
```

Percent Identity Matrix - created by Clustal2.1

```
    1: UPO12     100.00    74.38
    2: UPO27      74.38   100.00
```

RECOMBINANT HEME THIOLATE OXYGENASES

CROSS-REFERENCE TO RELATED APPLICATIONS

This application is the U.S. national stage of International Patent Application No. PCT/EP2020/069020, filed on Jul. 6, 2020 and entitled RECOMBINANT HEME THIOLATE OXYGENASES, which claims the benefit of priority under 35 U.S.C. § 119 from European Patent Application No. 19184720.1, filed Jul. 5, 2019. The disclosures of the foregoing applications are incorporated herein by reference in their entirety.

SEQUENCE LISTING

The entire content of a Sequence Listing titled "Sequence_ Listing.txt," created on Jan. 3, 2022 and having a size of 97 kilobytes, which has been submitted in electronic form in connection with the present application, is hereby incorporated by reference herein in its entirety.

FIELD OF THE INVENTION

The present invention relates to recombinant polypeptides having peroxygenase activity, their encoding polynucleotides, expression vectors and recombinant host cells comprising such polynucleotides or vectors. The present invention also relates to the use of the recombinant polypeptides as catalysts.

BACKGROUND ART

In the field of synthetic chemistry is oxygenation of organic molecules one of the major tasks. Oxygen-transferring enzymes can be used to solve this task through biocatalysis. In addition to cytochrome P450 enzymes, flavin dependent monooxygenases or di-iron dioxygenases, unspecific peroxygenases, called UPOs, or also POX due to their peroxidase activity, have the ability to transfer oxygen selectively to a wide range of substrates, such as polycyclic aromatic hydrocarbons, heterocycles, benzene derivatives, alkenes as well as linear and cyclic alkanes. Other reactions catalyzed by UPOs include double bond epoxidations, dealkylations, oxidation of inorganic halides as well as organic hetero atoms and also typical peroxidase reactions including radical based polymerization. Further they can even use pesticides or complex drug molecules as substrate. As such, applications of UPOs can be numerous; they reach from pharmaceutical production to environmental applications, including environmental problems caused by industry. For example, transformation of pollutants through peroxidases can result in reduction of toxicity or bioavailability. Also, removal of pollutants from water can be achieved.

UPOs belong to the peroxidase-peroxygenase group with haloperoxidases such as the *Caldariomyces fumago* chloroperoxidase (CfuCPO) as first and long known representative. Recombinant production of CfuCPO is also possible in suitable hosts such as *Aspergillus* spp., but no successful recombinant CfuCPO expression in yeast was published so far. CfuCPO has been the only heme-thiolate peroxidase characterized on the protein level for almost 50 years, before more versatile heme thiolate peroxidases were discovered. In the past decade a new subgroup of enzymes accepting especially aromatic substrates was described. One typical example for aromatic substrate conversion is the formation of 1- and 2-naphthol with naphthalene as substrate. 1-naphthol plays an important role in the production of pharmaceuticals, herbicides, and others. The first aromatic peroxygenase (AaeUPO) described was derived from the mushroom *Agrocybe aegerita* oxidizing similar substrates as CfuCPO, typical peroxidase substrates and aromatic alcohols and aldehydes. AaeUPO has the unique ability to epoxidize and hydroxylate aromatic rings efficiently by using hydrogen peroxide as oxygen donor.

In spite of the high technological potential and interest in these new secreted heme thiolate enzymes, their recombinant expression showed to be challenging and largely unsolved. Bormann et al. (2015) reported that attempts to express CfuCPO in *Escherichia coli*, *S. cerevisiae*, or *Pichia pastoris* (*Komagataella phaffi*) did not yield active enzyme. Although recombinant expression was successful in *Aspergillus niger*, the enzyme levels of few mg/L were significantly lower than with the native host. Molina-Espeja and M. Alcalde (2014) for the first time reported recombinant expression and engineering of AaeUPO in *S. cerevisiae*, still with very low enzyme yields of less than 0.01 mg/L but the first successful overexpression of a fungal heme thiolate peroxygenase by a yeast species. Employing the native signal sequence of AaeUPO1 resulted in 2-times higher secretion efficiency than the signal sequence of the *S. cerevisiae* mating factor alpha. No other UPOs could be functionally expressed as secreted enzymes by any yeast species and in general very few recombinant UPOs (expressed by filamentous fungi) were known so far. Directed evolution of AaeUPO1 (also named UPO1) in *S. cerevisiae* resulted in a mutant enzyme with increased activity and higher recombinant production yields (up to 217 mg/L in *P. pastoris*). This mutated sequence was also the first UPO which was successfully expressed by *P. pastoris* (Molina et al (2015)) using a methanol inducible AOX1 promoter and secreted to the culture supernatant. The AOX1 promoter is not a derepressed promoter and relies on methanol to obtain significant expression levels. Without the addition of methanol, the AOX1 promoter shows far less than 1% activity. No other UPO had been overexpressed by *P. pastoris* before and no natural heme thiolate peroxygenase with UPO or CPO activity had been successfully expressed by *P. pastoris*.

WO2008/119780 discloses polypeptides having peroxygenase activity. The polypeptides may be produced recombinantly in *Aspergillus oryzae*.

Thus, there is still the need for an effective expression system for producing novel unspecific peroxygenase enzymes (UPOs) in high yields and high enzyme activity.

SUMMARY OF INVENTION

It is the objective of the present invention, to provide novel recombinant polypeptides with peroxygenase activity, showing at least complementary activities and properties to known native UPOs and the UPO1 variants developed by Molina et al (2015).

It is further a specific objective of the present invention to provide polypeptides and polypeptide preparations having increased peroxygenase activity compared to the respective native UPOs, and to provide means and methods of their production in yeast cells.

The problem is solved by the present invention.

According to the invention, there is provided a method for producing a polypeptide having peroxygenase activity, comprising:
  a. cultivating a yeast cell in a medium conducive for the production of said polypeptide, wherein the yeast cell comprises a polynucleotide comprising a nucleic acid sequence encoding said polypeptide operably linked to a derepressed promoter sequence which is functional in methylotrophic yeasts, and b. isolating said polypeptide from the cultivation medium.

Specifically, the derepressed promoter sequence is a methanol-independent promoter.

A further embodiment relates to the method as described herein, wherein said promoter is an engineered or synthetic promoter variant.

A further embodiment relates to the method as described herein, wherein the promoter is a CTA1 (PDC) or FMD promoter.

A further embodiment relates to the method as described herein, wherein the expression and/or secretion is increased by co-expression of helper proteins.

A further embodiment relates to the method as described herein, wherein the helper protein is PDI.

A further embodiment relates to the method as described herein, wherein said yeast cell is a Pichia pastoris (Komagataella phaffii) cell.

A further embodiment relates to the method as described herein, wherein said polypeptide is obtained in a yield of about 1 mg/L, 10 mg/L, 50 mg/L, or of about 100 mg/L, or of about 250 mg/L.

Specifically, employing the method described herein, said polypeptide having peroxygenase activity, specifically a heme thiolate peroxygenase such as any of the unspecific peroxygenases (UPOs) described herein, is expressed at a yield of at least 250 mg/L.

A further embodiment relates to the method as described herein, wherein said polypeptide is obtained in the culture supernatant in a titer of about 300 mg/L, or of about 0.5 g/L, or of about 1 g/L.

A further embodiment relates to the method as described herein, wherein the polypeptide having peroxygenase activity comprises an MF-alpha signal sequence ("mating factor alpha" signal sequence).

Further provided herein is a method of producing a polypeptide having peroxygenase activity, comprising:
  a. cultivating a methylotrophic yeast cell, preferably Pichia pastoris, in a medium conducive for the production of said polypeptide, wherein the yeast cell comprises a polynucleotide comprising a nucleic acid sequence encoding said polypeptide operably linked to a promoter sequence which is functional in methylotrophic yeasts, and
  b. isolating said polypeptide from the cultivation medium.

Specifically, said promoter is an engineered or synthetic promoter variant. Specifically, said promoter is a CTA1 (PDC), FMD or AOX1 promoter.

Specifically, expression and/or secretion of the polypeptide having peroxygenase activity is increased by co-expression of helper proteins, preferably PDI.

Specifically, the polypeptide having peroxygenase activity comprises a MF-alpha signal sequence ("mating factor alpha" signal sequence).

Specifically, the yeast cell is a Pichia pastoris (Komagataella phaffii) cell.

One embodiment of the invention relates to a polypeptide which has a peroxygenase activity which is obtained by a method as described herein.

One embodiment of the invention relates to a polypeptide having peroxygenase activity selected from the group consisting of a polypeptide comprising an amino acid sequence having at least 70% sequence identity to the polypeptide of SEQ ID NO:1 (UPO1 mut), SEQ ID NO:2 (UPO2), SEQ ID NO:4 (UPO4), SEQ ID NO:5 (UPO5), SEQ ID NO:7 (UPO7), SEQ ID NO:11 (UPO11), SEQ ID NO:12 (UPO12), SEQ ID NO:17 (UPO17), SEQ ID NO:18 (UPO18), SEQ ID NO:19 (UPO19), SEQ ID NO:22 (UPO22), SEQ ID NO:23 (UPO23), SEQ ID NO:24 (UPO24), or SEQ ID NO:25 (UPO25).

One embodiment of the invention relates to a polypeptide having peroxygenase activity comprising an amino acid sequence having at least 75%, 80%, 85%, 90%, 95%, 97%, 98%, or 99% identity to the polypeptide of SEQ ID NO:1 (UPO1 mut), SEQ ID NO:2 (UPO2), SEQ ID NO:4 (UPO4), SEQ ID NO:5 (UPO5), SEQ ID NO:7 (UPO7), SEQ ID NO:11 (UPO11), SEQ ID NO:12 (UPO12), SEQ ID NO:17 (UPO17), SEQ ID NO:18 (UPO18), SEQ ID NO:19 (UPO19), SEQ ID NO:22 (UPO22), SEQ ID NO:23 (UPO23), SEQ ID NO:24 (UPO24), or SEQ ID NO:25 (UPO25).

One embodiment of the invention relates to a polypeptide having peroxygenase activity comprising or consisting of the amino acid sequence of SEQ ID NO:1 (UPO1 mut), SEQ ID NO:2 (UPO2), SEQ ID NO:4 (UPO4), SEQ ID NO:5 (UPO5), SEQ ID NO:7 (UPO7), SEQ ID NO:11 (UPO11), SEQ ID NO:12 (UPO12), SEQ ID NO:17 (UPO17), SEQ ID NO:18 (UPO18), SEQ ID NO:19 (UPO19), SEQ ID NO:22 (UPO22), SEQ ID NO:23 (UPO23), SEQ ID NO:24 (UPO24), or SEQ ID NO:25 (UPO25).

One embodiment of the invention relates to a polypeptide comprising an amino acid sequence having at least 70% sequence identity to the polypeptide of SEQ ID NO:12 (UPO12).

One embodiment of the invention relates to a polypeptide as described herein having increased peroxygenase activity when compared to a control peroxygenase (SEQ ID NO:1 (UPO1)), wherein the activity is about 10-fold, 20-fold, or 50-fold when measured in an ABTS assay.

One embodiment of the invention relates to the use of a polypeptide having peroxygenase activity as defined herein as peroxygenase, specifically as a catalyst in organic synthesis processes, polymerization processes, drug metabolite production, environmental application, application in consumer products, One embodiment of the invention relates to a recombinant polypeptide heaving peroxygenase activity and peroxidase activity, wherein the ratio between peroxidase activity and peroxygenase activity is about 1:1, 1:2, 1:3, 1:4, or 1:5 when peroxidase activity is expressed as ABTS units and peroxygenase activity is expressed as naphthalene units.

One embodiment of the invention relates to a recombinant polypeptide heaving peroxidase activity, with said peroxidase is active in a broad range of pH activity as determined by an ABTS assay.

One embodiment of the invention relates to a recombinant polypeptide heaving peroxygenase activity and peroxidase activity, wherein the KM value for hydrogen peroxide is about 1 mM or lower.

One embodiment of the invention relates to a polypeptide having peroxygenase activity and comprising an amino acid sequence having at least 70%, 75%, 80%, 85%, 90%, 95%, 97%, 98%, or 99% sequence identity to the polypeptide of SEQ ID NO:12 and comprising at least one amino acid modification, and wherein the polypeptide has increased peroxygenase activity when compared to UPO12 (SEQ ID NO:12). Preferably, said modification is at least one amino acid substitution in the sequence of SEQ ID NO:12. Specifically, the peroxygenase activity is about 1.0-fold, 1.1-fold, 1.2-fold, 1.3-fold, 1.4-fold, 1.5-fold, 1.6-fold, 1.7-fold, 1.8-fold, 1.9-fold, or 2.0-fold or more increased when measured in an ABTS assay and/or 2,6-DMP assay.

A specific embodiment of the invention relates to a polypeptide having peroxygenase activity and comprising an amino acid sequence having at least 70% sequence identity to the polypeptide of SEQ ID NO:12 and comprising one or more amino acid substitutions in the C-terminal region of SEQ ID NO:12 ranging from positions 130 to 261, preferably positions 145 to 261, of SEQ ID NO:12, wherein the polypeptide has increased peroxygenase activity when compared to UPO12 (SEQ ID NO:12).

Specifically, provided herein is a modified unspecific peroxygenase (UPO) comprising an amino acid sequence having at least 70% sequence identity to the polypeptide of SEQ ID NO:12 and having increased peroxygenase activity as compared to the unmodified wild-type UPO12, wherein the modification is a modification of at least one amino acid corresponding to any one of amino acids 145-261 of the unspecific peroxygenase of SEQ ID NO:12.

Specifically, the modified unspecific peroxygenase comprises a sequence having at least about 70%, 75%, 80%, 85%, 90%, 95%, 97%, 98%, or 99% identity to SEQ ID NO:12.

According to a specific embodiment, the modification is a modification of at least one amino acid corresponding to any one or more of amino acids C256, D253, E249, and/or D145 of the unspecific peroxygenase of SEQ ID NO:12. Specifically, the modified UPO comprises at least a mutation corresponding to C256S, D253N, D253I, and/or D145Y.

According to a further specific embodiment, the modification comprises introduction of a stop codon, preferably by an amino acid substitution, and/or comprises deletion of one or more amino acids, preferably at the C-terminus. Specifically, introduction of a stop codon is at a position corresponding to C256 or E249 of SEQ ID NO:12, in other words a modification corresponding to C256X or E249X, see for example SEQ ID NO:33 and SEQ ID NO:36.

According to a further specific embodiment, the modification comprises fusion to one or more N-terminal and/or C-terminal tags. Specific examples of such tags include but are not limited to fluorescent tags, such as a GFP tag or m-Cherry tag, and/or His-tags.

Specifically, the modified UPO comprises SEQ ID NO:31, SEQ ID NO:32, SEQ ID NO:33, SEQ ID NO:34, SEQ ID NO:35, or SEQ ID NO:36, or an amino acid sequence having at least 70%, 75%, 80%, 85%, 90%, 95%, 97%, 98%, or 99% identity to SEQ ID NO:31, SEQ ID NO:32, SEQ ID NO:33, SEQ ID NO:34, SEQ ID NO:35, or SEQ ID NO:36.

A further specific embodiment of the invention relates to a modified unspecific peroxygenase (UPO) having increased peroxygenase activity as compared to the unmodified wild-type UPO12, wherein the modified UPO comprises SEQ ID NO:30, or an amino acid sequence having at least 70%, 75%, 80%, 85%, 90% or 95% sequence identity to SEQ ID NO:30. Specifically, said UPO comprises a modification of at least one amino acid corresponding to the amino acid at position S24 of the UPO of SEQ ID NO:12. Specifically, said modification is an amino acid substitution corresponding to S24F.

According to a specific embodiment, the modified UPO comprising SEQ ID NO:30, or an amino acid sequence having at least 70% sequence identity to SEQ ID NO:30, comprises an additional modification of at least one amino acid corresponding to any one or more of amino acids at positions C256, D253, E249, and/or D145 of the UPO of SEQ ID NO:12. More specifically, said UPO further comprises one or more mutations corresponding to C256S, C256X, E249X, D253N, D253I, and/or D145Y.

Specifically, the peroxygenase activity of the modified UPO described herein is about 1.0-fold, 1.1-fold, 1.2-fold, 1.3-fold, 1.4-fold, 1.5-fold, 1.6-fold, 1.7-fold, 1.8-fold, 1.9-fold, or 2.0-fold or more increased when measured in an ABTS assay and/or in a DMP assay as described herein.

One embodiment of the invention relates to an isolated polypeptide having peroxygenase activity, wherein the polypeptide comprises SEQ ID NO:37 (POX27 or UPO27), SEQ ID NO:38 (POX30 or UPO30), SEQ ID NO:39 (POX32 or UPO32), SEQ ID NO:40 (POX34 or UPO34) or SEQ ID NO:41 (POX39 or UPO39), or an amino acid sequence having at least 70%, 75%, 80%, 85%, 90%, 95%, 97%, 98%, or 99% identity to comprises SEQ ID NO:37 (POX27), SEQ ID NO:38 (POX30), SEQ ID NO:39 (POX32), SEQ ID NO:40 (POX34) or SEQ ID NO:41 (POX39).

Further provided herein is the use of the polypeptides having peroxidase activity described herein as peroxygenase, specifically they are used in a method employing a biocatalyst having peroxygenase activity, which is the polypeptide having peroxidase activity as described herein.

Specifically, the isolated polypeptide having peroxygenase activity, wherein the polypeptide comprises SEQ ID NO:37 (POX27 or UPO27), SEQ ID NO:38 (POX30 or UPO30), SEQ ID NO:39 (POX32 or UPO32), SEQ ID NO:40 (POX34 or UPO34) or SEQ ID NO:41 (POX39 or UPO39), or an amino acid sequence having at least 70%, 75%, 80%, 85%, 90%, 95%, 97%, 98%, or 99% identity to comprises SEQ ID NO:37 (POX27), SEQ ID NO:38 (POX30), SEQ ID NO:39 (POX32), SEQ ID NO:40 (POX34) or SEQ ID NO:41 (POX39) is used as peroxygenase.

Specifically, the polypeptides described herein comprising or consisting of the amino acid sequence of SEQ ID NO:1 (UPO1 mut), SEQ ID NO:2 (UPO2), SEQ ID NO:4 (UPO4), SEQ ID NO:5 (UPO5), SEQ ID NO:7 (UPO7), SEQ ID NO:11 (UPO11), SEQ ID NO:12 (UPO12), SEQ ID NO:17 (UPO17), SEQ ID NO:18 (UPO18), SEQ ID NO:19 (UPO19), SEQ ID NO:22 (UPO22), SEQ ID NO:23 (UPO23), SEQ ID NO:24 (UPO24), or SEQ ID NO:25 (UPO25) or the polypeptides described herein comprising an amino acid sequence having at least 70%, 75%, 80%, 85%, 90%, 95%, 97%, 98%, or 99% identity to the polypeptide of SEQ ID NO:1 (UPO1 mut), SEQ ID NO:2 (UPO2), SEQ ID NO:4 (UPO4), SEQ ID NO:5 (UPO5), SEQ ID NO:7 (UPO7), SEQ ID NO:11 (UPO11), SEQ ID NO:12 (UPO12), SEQ ID NO:17 (UPO17), SEQ ID NO:18 (UPO18), SEQ ID NO:19 (UPO19), SEQ ID NO:22 (UPO22), SEQ ID NO:23 (UPO23), SEQ ID NO:24 (UPO24), or SEQ ID NO:25 (UPO25) are used as peroxygenase.

Specifically, the newly identified peroxygenase UPO27 (SEQ ID NO:37) has about 72% sequence identity to the peroxygenase UPO12 (SEQ ID NO:12). Without the signal sequence, UPO27 has about 74% sequence identity to UPO12.

According to a specific embodiment of the invention, the modified unspecific peroxygenases described herein, and the isolated polypeptides having peroxygenase activity described herein are produced according to the method described herein.

BRIEF DESCRIPTION OF DRAWINGS

FIG. 7: Sequence of selected constructs

FIG. 8: Comparison of peroxygenase and peroxidase activities of selected constructs in the Naphthalene—Fast Blue assay and ABTS assay.

FIG. 12: ClustalW Alignment of wildtype UPO12 and UPO12 variants.

FIG. 13: ClustalW Alignment of newly identified peroxygenase UPO27(POX27) and wildtype UPO12.

DESCRIPTION OF EMBODIMENTS

Figure 1:
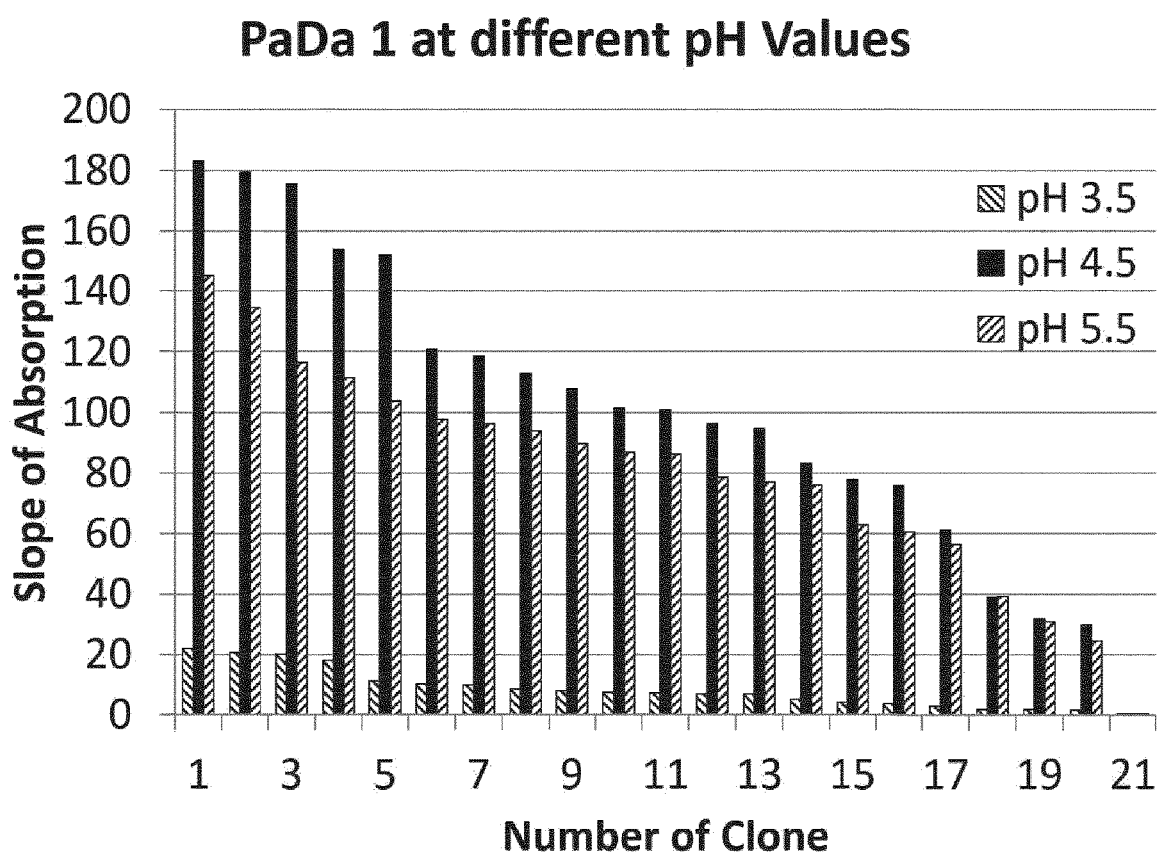
FIG. 1: Activity landscapes of 21 different PaDa1 mutant transformants at different pH values. While the mutant samples converted ABTS only really slow at pH 3.5, the conversion was more than 10 times faster at pH 4.5 for several clones.

Unless indicated or defined otherwise, all terms used herein have their usual meaning in the art, which will be clear to the skilled person.

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

As used herein and in the claims, the singular form, for example "a", "an" and "the" includes the plural, unless the context clearly dictates otherwise.

Peroxidases are divided in four superfamilies, the peroxidase catalase superfamily, the peroxidase-cyclooxygenase superfamily, the peroxidase-chlorite dismutase superfamily and the peroxidase-peroxygenase superfamily (Zámocký et al. 2015).

Peroxidases carry iron (III) protoporphyrin IX as prosthetic group and in general catalyze the oxidation of various organic and inorganic compounds and the reduction of peroxides as $H_2O_2$.

According to Zámocký et al. (2015) peroxidases catalyze four different reactions:

$$H_2O_2 + 2AH_2 \rightarrow H_2O + 2 \cdot AH \quad \text{Reaction 1:}$$

$$H_2O_2 + X^- + H^+ \rightarrow H_2O + HOX \quad \text{Reaction 2:}$$

$$H_2O_2 + H_2O_2 \rightarrow 2H_2O + O_2 \quad \text{Reaction 3:}$$

$$H_2O_2 + RH \rightarrow H_2O + ROH \quad \text{Reaction 4:}$$

In Reaction 1 electron donors ($AH_2$) are oxidized to radicals (AH) while $H_2O_2$ is reduced to water. Reaction 2 shows halides as two-electron donors ($X^-$). These are oxidized to hypohalous acids (HOX). The third reaction shows the release of oxygen when a second hydrogen peroxide is used as electron donor. The fourth reaction shows the introduction of oxygen functionalities into organic molecules. Reactions 1 and 2 are common peroxidation reactions, Reaction 3 can be observed only in few heme peroxidases and Reaction 4 is a peroxygenation like reaction, additionally to their peroxidative activity, found in UPOs. The peroxygenase activity reaction mechanism of UPOs is similar to the peroxide shunt pathway of cytochrome P450 enzymes (Zámocký et al. 2015) and bacterial intracellular P450 peroxygenases such as OleT.

According to phylogenetic analyses UPO sequences consist of the motifs (PCP---EGD---R----E) required for the enzyme activity. Both, UPO and CPO have the PCP motif which is required for catalytic activity. The distal cavity of both enzymes consists of a negatively charged glutamic acid residue, which is stabilized by histidine in case of CPO and arginine in case of AaeUPO. In LfuCPO (=CfuCPO) this H105 is involved in the mechanism of its peroxidase function, participating in the cleavage of hydrogen peroxide. The third required motif for catalytic activity in AaeUPO is EGD, which is EHD in CPO. The extended conserved motif for AaeUPO is -PCP-EGD-R--E, and for MroUPO and CPO is -PGP-EHD-E. According to Faiza et al. 2019, most of the putative fungal UPOs reside in Basidiomycota phylum of fungal kingdom. Interestingly MroUPO was placed along with the LfuCPO and some other CPO sequences in the phylogenetic tree. Two new motifs were identified namely, the S [IL] G motif located between the PCP and the EGD motifs and SXXRXD motif present after the EGD motif, except in MroUPO. According to their analysis a II UPOs consist Ile in S [IL] G motif except three species: *Jaapia argillacea* mucI33604, *Mixia osmundae* iam14324, and *Sphaeru-lina musiva* so2202, which contain Leu in place of Ile. This motif was predicted to be relevant for specific substrate selectivity. Thr55 in AaeUPO was predicted to be a critical amino acid residue possibly responsible for driving the functional divergence of UPOs from the CPOs.

Only few wild-type UPOs, including isolated enzymes from *Coprinellus radians, Marasmius rotula* and *A. aegerita* have been characterized biochemically. Although more UPOs have been identified based on sequence similarities, these proteins were not isolated and biochemically characterized in detail yet.

So far UPOs were excluded from different possible industrial applications due to missing suitable heterologous expression system. Attempts to functionally express native UPOs in *P. pastoris* failed or showed nearly undetectable levels of expression (Molina-Espeja et al., 2015) and isolation of such recombinant enzyme from the culture supernatant was not feasible (Molina-Espeja et al. 2015 A wild-type peroxygenase of *C. cinera* was expressed heterologously in *A. oryzae* (Babot et al., 2013). In one case expression of stable, soluble AaeUPOs in *S. cerevisiae* and *P. pastoris* was brought to an acceptable level through directed evolution over several generations. The activity was measured mainly through ABTS assays with 0.3 mM ABTS and 2 mM hydrogen peroxide (Molina-Espeja et al., 2015).

Further studies showed that there is a similarity of around 30% identity from the sequences of the unspecific peroxygenases AaP and CrP to the sequence of the chloroperoxidase of *C. fumago* (CfuCPO or LfuCPO). This similarity is located at the N-terminus and comprises the proximal heme-binding region, while the C-terminus is differing completely (Pecyna et al., 2009).

A Blast search of selected sequences of possible unspecific peroxygenases against the sequence of this chloroperoxidase showed similar results with a maximum identity of 25%, but all sequences contained the conserved cysteine residue of the PCP motif that is found in the peroxygenases AaP and CrP as well as in the chloroperoxidase where it serves as fifth heme ligand and has the position Cys29 (Pecyna et al. 2009).

The following alignment, created with Clustal Omega, shows the conserved sequence motifs described above:

also showed improved technical properties compared to previously described recombinant UPOs and they can be expressed by secretion by yeast.

The present invention also relates to nucleic acid constructs comprising an isolated polynucleotide of the present invention operably linked to one or more (several) control sequences that direct the expression of the coding sequence in a suitable host cell under conditions compatible with the control sequences. An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art. The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

There are several methods to determine the activity of peroxygenases based on different hydrogen donors, such as guaiacol, pyrogallol, ABTS (2,2'-Azino-bis(3-ethylbenzothiazoline-6-sulfonic acid) diammonium salt), 4-methoxyl-α-naphthol and phenol plus amino-antipyrine, or 2,6-DMP (Yuan & Jiang, 2002). Among them, ABTS is a widely used substrate in the spectrophotometric determination of peroxidase and peroxygenase activity because the method is sensitive and the chromogenic products are stable (Pütter & Becker, 1983; Yuan & Jiang, 2002).

The peroxygenase activity of the polypeptides having peroxygenase activity described herein, specifically the

```
                                                      (SEQ ID NO: 26)
31   YDNNTLPYVAPGPT DSRAPCPALNALANHGYIPHDG RAISRETLQNAFLNHMGIANSVIE    90

(SEQ ID NO: 27)
     VNDKDHPWKPLRPG DIRGPCPGLNTLASHGYLPRNG VATPAQIIN-AVQEGFNMDNSVAL   118
                    proximal heme binding (SEQ ID NO: 28)
91   LALTNAFVVC-EY------------VTGSDCGDSLVNLTLLA EPHAFEHDHSFSRKDYKQG   138

(SEQ ID NO: 29)
119  FATYEAHLMVGNLLTDLLSIGRKTPLTGPDLP-PPANIGGLS EHGLFEGDASMTRGDAFFG   177
                                               heme propionates environment
```

Alignment of the AaP and the CrP peroxygenase with the chloroperoxidase of *C. fumago* (CfuCPO) demonstrated that the substrate binding is different. Although some epoxidation activity was described for LfuCPO in comparison to UPOs, CPOs are usually not able to epoxidize aromatic rings or to hydroxylate alkanes with the same efficiency.

Thus, it was an object of the invention to evaluate the *Pichia* system for achieving high yields and titers of new UPOs. The present invention therefore relates to reproducible expression of novel UPOs by the robust and efficient expression system *P. pastoris* as folded and functional enzymes. The recombinant UPOs of the present invention UPOs described herein, is preferably determined using an ABTS assay or a 2,6-DMP assay.

The ABTS Assay (2,2'-Azino-bis(3-Ethylbenzothiazoline-6-Sulfonic Acid) (ABTS) Enzymatic Assay) is a colorimetric assay based on the ABTS cation radical formation and is well-known in the art, described for example in Pütter & Becker, 1983. The radical formation is catalyzed by the reduction of HRP in the presence of hydrogen peroxide.

According to a specific example, the ABTS assay is carried out analogously as described by Morawski et al. (2000) for horse radish peroxidase (HRP). The ABTS assay may be performed with variable parameters, including varying concentration of the buffer at different pH values. As ABTS assay solution 440 mg 2,2'-azino-bis(3-ethylbenzothiazoline-6-sulfonic acid) in NaOAc may be mixed with buffer and 30% $H_2O_2$. The cell culture supernatant is mixed with the assay solution and the increase in absorption at 405 nm is measured to determine the peroxidase and/or peroxygenase activity.

The 2,6-DMP assay, or DMP assay in short, is another preferred activity assay that is used to detect and measure peroxygenase activity of the polypeptides described herein. In this method, 2,6-dimethoxyphenol and hydrogen peroxide are used as co-substrates in a nonspecific peroxygenase-catalyzed reaction leading to the formation of a colored product.

To determine an increased activity, a benchmark is also measured in the activity assay. The benchmark may for example be the wild-type polypeptide, not comprising any of the modifications described herein, or the PaDa1 mutant (of AaeUPO1). The benchmark is measured under the same conditions as the polypeptide of interest for which an increased activity shall be determined.

Surprisingly, the modified unspecific peroxygenases described herein comprise an increased peroxygenase activity of about at least 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5 or 10-fold increased activity as determined by ABTS assay and/or by DMP assay. Surprisingly, the largest group of the UPO12 variants described herein comprising improved peroxygenase activity were found to have a mutation at the C-terminus of the POX12 (UPO12) protein sequence.

The term "C-terminus" (also known as the carboxyl-terminus, carboxy-terminus, C-terminal tail, C-terminal end, or COOH-terminus) as used herein refers to the end of an amino acid chain (protein or polypeptide) comprising a free carboxyl group (—COOH). The C-terminus may comprise any of 5, 10, 15, 20, 25, 50, 100, 150, or 200 amino acids, or any number in between.

Specifically, the term C-terminus as used herein with reference to the modified UPOs described herein, refers to a sequence of amino acids corresponding to amino acids 145-261 of UPO12, preferably amino acids 230 to 261, or even more preferably to the amino acids from position 240 or 250 to 261, of the UPO of SEQ ID NO:12. Specifically, the sequence corresponding to the C-terminus of SEQ ID NO:12 is not necessarily identical to the C-terminus of SEQ ID NO:12 but shares at least about 70, 75, 80, 85, 90, or 95% sequence identity.

Specifically, the modified UPOs described herein comprise one or more amino acid modifications at positions corresponding to S24, C256, D253, E249, and/or D145 of SEQ ID NO:12. The position of the amino acid modification may not be identical to positions S24, C256, D253, E249, and/or D145 of SEQ ID NO:12, but it is functionally equivalent to said positions. Identification of functionally equivalent positions is readily available to a person skilled in the art, for example by employing structural alignments.

The polypeptides having peroxygenase activity described herein, specifically the UPOs described herein, including the modified UPOs described herein, can be used in various applications. Specifically, the polypeptides described herein are employed in oxyfunctionalization reactions, oxidative defunctionalization reactions and/or oxidative polymerization reactions. Industrial applications of the UPOs described herein and isolated polypeptides comprising peroxygenase activity are numerous; they reach from pharmaceutical production to environmental applications, including environmental problems caused by industry. For example, transformation of pollutants using the UPOs described herein can result in reduction of toxicity or bioavailability. Also, removal of pollutants from water can be achieved.

The polypeptides having peroxygenase activity described herein, specifically the UPOs described herein, including the modified UPOs described herein, may be further modified, such modifications including for example insertion or deletion of post-translational modification sites, insertion or deletion of targeting signals (e.g.: leader peptides), fusion to tags, linker peptides, proteins or protein fragments facilitating their processing such as purification or detection or enhancing their stability.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, linker peptides causing ribosomal skipping, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the present invention and is operably linked to additional nucleotides that provide for its expression.

The term "functional variant" or "functionally active variant" also includes naturally occurring allelic variants, as well as mutants or any other non-naturally occurring variants of the UPOs described herein. As is known in the art, an allelic variant is an alternate form of a nucleic acid or peptide that is characterized as having a substitution, deletion, or addition of one or nucleotides or more amino acids that does essentially not alter the biological function of the nucleic acid or polypeptide.

Functional variants may be obtained by sequence alterations in the polypeptide or the nucleotide sequence, e.g. by one or more point mutations, wherein the sequence alterations retains or improves a function of the unaltered polypeptide or the nucleotide sequence, when used in combination of the invention. Such sequence alterations can include, but are not limited to, (conservative) substitutions, additions, deletions, mutations and insertions.

A point mutation is particularly understood as the engineering of a polynucleotide that results in the expression of an amino acid sequence that differs from the non-engineered amino acid sequence in the substitution or exchange, deletion or 5 insertion of one or more single (non-consecutive) or doublets of amino acids for different amino acids.

The term "heterologous" as used herein with respect to a nucleotide or amino acid sequence or protein, specifically the UPOs and promoters described herein, refers to a compound which is foreign, i.e. "exogenous", such as not found in nature, to a given host cell. The heterologous nucleotide sequence may also be expressed in an unnatural, e.g., greater than expected or greater than naturally found, amount in the cell. Specifically, heterologous nucleotide sequences are those not found in the same relationship to a host cell in nature (i.e., "not natively associated"). Any recombinant or artificial nucleotide sequence is understood to be heterologous. An example of a heterologous polynucleotide or nucleic acid molecule comprises a nucleotide sequence not natively associated with a promoter, e.g., to obtain a hybrid promoter, or operably linked to a coding sequence, as described herein. As a result, a hybrid or chimeric polynucleotide may be obtained. A further example of a heterologous compound is a UPO-encoding polynucleotide or gene operably linked to a transcriptional control element, e.g., a promoter, to which an endogenous, naturally-occurring POI coding sequence is not normally operably linked.

"Sequence identity" as described herein is defined as the percentage of nucleotides or amino acid residues in a candidate sequence that are identical with the nucleotides or amino acid residues in the specific nucleotide or polypeptide sequence to be compared (the "parent sequence"), after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "operably linked" as used herein refers to the association of nucleotide sequences on a single nucleic acid molecule, e.g. the vector, plasmid or chromosome, in a way such that the function of one or more nucleotide sequences is affected by at least one other nucleotide sequence present on said nucleic acid molecule. For example, a promoter is operably linked with a coding sequence encoding a UPO described herein, when it is capable of effecting the expression of that coding sequence. Specifically, such nucleic acids operably linked to each other may be immediately linked, i.e. without further elements or nucleic acid sequences in between or may be indirectly linked with spacer sequences or other sequences in between.

The term "host cell", as used herein, includes any cell type that is susceptible to transformation, transfection, transduction, and the like with a nucleic acid construct or expression vector comprising a polynucleotide of the present invention.

Specifically, the host yeast cells are maintained under conditions allowing expression and/or secretion of the peroxygenases described herein.

In one aspect the host cell is a yeast cell. "Yeast" as used herein includes *ascosporogenous* yeast (*Endomycetales*), *basidiosporogenous* yeast, and yeast belonging to the Fungi Imperfecti (*Blastomycetes*). In one aspect, the yeast host cell is a *Candida, Hansenula, Kluyveromyces, Pichia, Saccharomyces, chizosaccharomyces*, or *Yarrowia* cell. In a further aspect, the yeast host cell is a *Pichia pastoris* cell.

Specifically, the methylotrophic yeasts *Komagataella* (*Pichia*) *pastoris*, *Komagataella* (*Pichia*) *phaffii* (Pp), *Komagataella kurtzmanii*, *Ogataea* (*Hansenula*) *polymorpha* (Hp), *Candida boidinii* (Cb) and *Ogataea* (*Pichia*) *methanolica* (Pm) have been established as efficient alternative production strains. These strains make it possible to achieve high expression rates for heterologous proteins with a high cell density. Of the aforementioned four yeast species, *P. pastoris* (*Komagataella phaffii*) has in the meantime been used most commonly for heterologous protein production.

The term "methylotrophic yeast cells", as used herein, includes yeast cells capable of growing on culture media containing as carbon source substances with only one carbon atom, for example methanol.

The term "promoter" as used herein refers to an expression control element that permits binding of RNA or DNA polymerase and the initiation of transcription.

"Derepressing conditions", as used in culturing the yeast cells according to one aspect, means that the yeast cells are first cultured in the presence of a repressing carbon source (e.g. glucose) until this carbon source has been mostly or entirely consumed. After reducing the concentration of the repressing carbon source (e.g. glucose), the cells are in derepressing conditions with respect to the repressing carbon source and glucose, respectively. The strength of the repression effects may depend on the type of carbon source and on specific growth rates.

Derepressed promoter sequences are activated by derepression upon carbon source limitation and depletion and not upon induction by methanol.

The derepressed and methanol-independent promoters used according to the present invention display at least 10% activity in a suitable environment that does not comprise methanol. Preferably, such promoters comprise at least 10%, 15%, 20%, 25%, 30%, 35%, 40%, 45%, 50%, 55%, 60%, 65%, or 70% under derepressing conditions and without the addition of methanol.

In contrast, methanol-dependent promoter sequences, such as the AOX1 promoter, display less than 1% activity, typically less than 0.1% or even less, without the addition of methanol to the cell culture.

In a yeast host, useful promoters are for example, AOX1, PDC, and PDF, FMD and FDH or FLD promoters and peroxisomal catalase gene promoters of different methylotrophic yeast as well as for example promoters of genes, coding for peroxisomal proteins. According to a preferred embodiment, the PDC or FMD promoter is used in the method described herein.

The term "signal peptide", as used herein, refers to a peptide linked to the C-terminus or N-terminus of the polypeptide, which controls the secretion of the polypeptide. The signal sequence used may be a polynucleotide which codes for an amino acid sequence which initiates the transport of a protein through the membrane of the endoplasmic reticulum (ER). The nucleic acid sequence of these signal sequences may correspond to the natural sequence of the original host cell or may be codon-optimized. The non-limited examples of the signal sequence include native fungal plant or animal protein signal sequences, MF-alpha ("mating factor alpha" signal sequence), the OST1 signal peptide, the signal sequence of the CBH2 protein from *Trichoderma reesei*, the signal sequence of the xylanase A from *Thermomyces lanuginosus*, Kl killer toxin signal, the signal peptide for invertase secretion, the signal sequence of the killer toxin from *Kluyveromyces lactis*, the signal sequence of the killer toxin from *Pichia acaciae*, the signal sequence of the killer toxin from *Hanseniaspora uvarum* and from *Pichia (Hansenula) anomala* or variants thereof and signal sequences of proteins exposed at the surface of *P. pastoris*. In one aspect, the preferred signal sequence is MF-alpha ("mating factor alpha" signal sequence). According to a further preferred aspect, the signal sequence is a signal sequence from *Podospora anserine*.

A suitable expression system is for example disclosed in WO2017/109082.

On aspects related to the selection and codon optimization of sequences, expression system and confirmation of the activity of the enzymes. Different new enzyme sequences showing a clear difference to so far known enzymes were identified and provided.

The term "cell culture" or "cultivation" ("culturing" is herein synonymously used), also termed "fermentation", with respect to a host cell line is meant to be the maintenance of yeast cells in an artificial, e.g., an in vitro environment, under conditions favoring growth, differentiation or continued viability, in an active or quiescent state, of the cells, specifically in a controlled bioreactor according to methods known in the industry. When cultivating, a cell culture is brought into contact with the cell culture media in a culture vessel or with substrate under conditions suitable to support cultivation of the cell culture and expression and/or secretion of the peroxygenases described herein. Specifically, a culture medium is used to culture cells according to standard cell culture techniques that are well-known in the art for cultivating or growing yeast cells.

Cell culture may be a batch process or a fed-batch process. A batch process is a cultivation mode in which all the nutrients necessary for cultivation of the cells, and optionally including the substrates necessary for production of the carbonyl compounds described herein, are contained in the initial culture medium, without additional supply of further nutrients during fermentation. In a fed-batch process, a feeding phase takes place after the batch phase. In the feeding phase one or more nutrients, such as the substrate described herein, are supplied to the culture by feeding. In certain embodiments, the method described herein is a fed-batch process. Specifically, a host cell transformed with a nucleic acid construct encoding the polypeptides described herein, specifically the UPOs as described herein, is cultured in a growth phase medium and transitioned to an induction phase medium in order to produce the polypeptides described herein.

In another embodiment, host cells described herein are cultivated in continuous mode, e.g. a chemostat. A continuous fermentation process is characterized by a defined, constant and continuous rate of feeding of fresh culture medium into the bioreactor, whereby culture broth is at the same time removed from the bioreactor at the same defined, constant and continuous removal rate. By keeping culture medium, feeding rate and removal rate at the same constant level, the cultivation parameters and conditions in the bioreactor remain constant.

Suitable cultivation techniques may encompass cultivation in a bioreactor starting with a batch phase, followed by a short exponential fed batch phase at high specific growth rate, further followed by a fed batch phase at a low specific growth rate. Another suitable cultivation technique may encompass a batch phase followed by a continuous cultivation phase at a low dilution rate.

It is preferred to cultivate the host cell line as described herein in a bioreactor under growth conditions to obtain a cell density of at least about 1 g/L, 5 g/L or 10 g/L cell dry weight, more preferably at least 20 g/L cell dry weight, preferably at least 50 g/L cell dry weight. It is advantageous to provide for such yields of biomass production on a pilot or industrial scale.

The term "mutation" as used herein has its ordinary meaning in the art. A mutation may comprise a point mutation, or refer to areas of sequences, in particular changing contiguous or non-contiguous amino acid sequences. Specifically, a mutation is a point mutation, which is herein understood as a mutation to alter one or more (but only a few) contiguous amino acids, e.g. 1, or 2, or 3 amino acids, which are substituted, inserted or deleted at one position in an amino acid sequence. Amino acid substitutions may be conservative amino acid substitutions or non-conservative amino acid substitutions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

The term "functional variant" or "functionally active variant" also includes naturally occurring allelic variants, as well as mutants or any other non-naturally occurring variants. As is known in the art, an allelic variant is an alternate form of a nucleic acid or peptide that is characterized as having a substitution, deletion, or addition of one or nucleotides or more amino acids that does essentially not alter the biological function of the nucleic acid or polypeptide. Functional variants may be obtained by sequence alterations in the polypeptide or the nucleotide sequence, e.g. by one or more point mutations, wherein the sequence alterations retain or improve a function of the unaltered polypeptide or the nucleotide sequence, when used in combination of the invention. Such sequence alterations can include, but are not limited to, (conservative) substitutions, additions, deletions, mutations and insertions.

In one aspect as described herein, several UPOs from basidiomycetes and ascomycetes were identified and studied. In Table 1 the constructs that have been tested are listed with their associated accession numbers.

TABLE 1

Tested UPO and CPO candidates

| Candidate | Accession number | Notes |
| --- | --- | --- |
| UPO 1mut | B9W4V6 | PaDa I mutant |
| UPO 2 | KDR72024.1 | Unspecific peroxygenase |
| UPO 3 | KJA13294.1 | Unspecific peroxygenase |
| UPO 4 | XP_006458802 | Unspecific peroxygenase |
| UPO 5 | KIK06072.1 | Unspecific peroxygenase |
| UPO 6 | KIJ31387.1 | Unspecific peroxygenase |
| UPO 7 | KIM43689.1 | Unspecific peroxygenase |
| UPO 8 | KJA24696.1 | Unspecific peroxygenase |
| UPO 9 | ESZ93716.1 | Unspecific peroxygenase |
| UPO 10 | CAK39169.1 | Unspecific peroxygenase |
| UPO 11 | OJJ73116.1 | Unspecific peroxygenase |
| UPO 12 | OTA57433.1 | Unspecific peroxygenase |
| UPO 13 | XP_001225194.1 | Unspecific peroxygenase |
| UPO 14 | XP_001219540.1 | Unspecific peroxygenase |
| UPO 15 | KIJ30163.1 | Unspecific peroxygenase |

TABLE 1-continued

Tested UPO and CPO candidates

| Candidate | Accession number | Notes |
|---|---|---|
| UPO 16 | KIJ46203.1 | Unspecific peroxygenase |
| UPO 17 | XP_001911526.1 | Unspecific peroxygenase |
| UPO 18 | XP_006459044.1 | Unspecific peroxygenase |
| CPO 19 | CAA28172 | Chloroperoxidase |
| CPO 20 | AJA36817 | Chloroperoxidase |
| UPO21* | CAV28569.1 | Unspecific peroxygenase |
| UPO22 | OTB17553.1 | Unspecific peroxygenase |
| UPO23 | GAQ45152.1 | Unspecific peroxygenase |
| UPO24 | XP_001390900.2 | Unspecific peroxygenase |
| UPO25 | GAA88053.1 | Unspecific peroxygenase |

In one aspect, the polypeptide comprises an amino acid sequence having at least 70%, 75%, 80%, 85%, 90%, 95%, 97%, 98%, or 99% identity to the polypeptide of SEQ ID NO:11 (UPO11).

In one aspect, the polypeptide comprises an amino acid sequence having at least 70%, 75%, 80%, 85%, 90%, 95%, 97%, 98%, or 99% identity to the polypeptide of SEQ ID NO:12 (UPO12).

In one aspect, the polypeptide comprises an amino acid sequence having at least 80%, 85%, 90%, 95%, 97%, 98% or 99% identity to the polypeptide of SEQ ID NO:17 (UPO17).

In one aspect, the polypeptide comprises an amino acid sequence having at least 95% identity to the polypeptide of and SEQ ID NO:23 (UPO23).

In one embodiment as described herein, using *Pichia pastoris* as expression system with a methanol-independent PDC promoter and the engineered gene/protein sequence as described herein more than 200 mg/L secreted enzyme were obtained. One aspect provides for yields of 0.5 g/L or even 1 g/L of the desired enzyme. This yield came close to secreted UPO concentrations observed in native hosts.

EXAMPLES

The Examples which follow are set forth to aid in the understanding of the invention but are not intended to, and should not be construed to limit the scope of the invention in any way. The Examples do not include detailed descriptions of conventional methods, e.g., cloning, transfection, and basic aspects of methods for expressing proteins in microbial host cells. Such methods are well known to those of ordinary skill in the art.

Materials and Methods

Sequence Selection Procedure

Sequences described in databases were analyzed or potential peroxygenase activity using various free available sequence databases, e.g. genbank at NCBI with the data sets nonredundant or patdb Google Patent search, Canadian Patents Database, Patentscope, Espacenet, and DPMA.

Searches were done based by blast searches using previously published sequences with known or claimed activities as input.

Signal BLAST and SignalP were used for analyzing all those sequences individually in order to find out if a hypothetical protein is potentially secreted and to identify predictable signal sequence cleavage sites, enabling the replacement of native signal peptides by others such as the signal sequence of the *S. cerevisiae* mating factor alpha.

A Multiple Sequence Alignment as well as a phylogenetic tree were obtained by Clustal Omega analysis, which uses the neighbor-joining method for the phylogenetic tree.

Out of this huge amount of data a matrix for choosing sequences was generated. Two big groups were identified depending on the similarity, with each of them having several hotspots containing notably high similarities as it showed up, in the heatmap, which supported the final decision process.

Final sequence selections were made based on the sequence comparisons in order to stay in distance from previously known and/or characterized UPOs, for reflecting a broad coverage of sequence diversity in the phylogenetic tree and to cover a broad sequence diversity which also might reflect functional diversity. However also known heme thiolate peroxygenases such as the AaeUPO1 variant PaDa1 and the CfuCPO were included in the performed expression studies. The evolved AaeUPO1 variant served as a positive control for expression and activity tests, while the CPO was used as one of the negative controls, since functional secretory expression by *Pichia pastoris* was reported to have failed in other labs before.

Sequencing Genes of Interest

Single colonies that (due to the colony PCR) were likely to contain the cloned peroxygenase reading frames, cloned into the expression vector, inter alia, were streaked out on LB Zeocin plates and incubated at 37° C. overnight to amplificate the recombinant plasmid.

A minipreparation of plasmid DNA was done with Promega's "Wizard® Plus SV Minipreps DNA Purification System" as described herein.

For sequence verification and analysis of potential errors produced by DNA synthesis or PCR amplification/cloning, isolated plasmid DNA was sent for Sanger sequencing of the DNA. Therefore at least 1,200 ng of DNA plus 3 µL of 10 µM forward or reverse primer, respectively, were brought to a total volume of 15 µL with dH$_2$O.

*P. pastoris* Transformation

For the transformation of electrocompetent cells and for genomic integration of the expression cassettes the vectors were linearized by a single cut using SwaI. Deviating from standard protocols only 0.5 µL of enzyme were used and the incubation time was increased to three hours after checking in the enzyme manufacturers description that the used restriction enzyme has no star activity.

The linearized expression cassettes were desalted by dialysis using filter discs floating on water, before the DNA was used for *Pichia* transformation.

For one transformation 40 µL of ready to use electrocompetent *Pichia pastoris* BSYBG11 cells (Table 6, Bisy GmbH, Austria) and around 1 µg of linearized plasmid DNA were used.

First of all the competent cells were defrosted on ice and the cuvettes were cooled. Then the competent cells and the plasmid DNA were pooled in the cooled cuvettes and kept on ice for at least 10 minutes. Afterwards electroporation was carried out with a voltage of 1.5 kV, followed by the addition of regeneration medium (YPD/1 M Sorbitol, 1:1 (v/v)).

The mixture containing transformants and regeneration medium was transferred to Eppendorf tubes (0) and regenerated for 2 hours at 30° C. and 700 rpm, followed by a centrifugation step (1 min, full speed). The supernatant was reduced to 100 µL, the cell pellet was resuspended therein and plated on LB-Zeocin plates. The plates were incubated at 30° C. for two days.

Cultivation

Cultivation was carried out in deep well plates either as one or as two-day(s) induction.

Two-Day Induction:

Single colonies of the transformed *Pichia pastoris* cells (from 0) were picked with sterile toothpicks. Then they were transferred to the wells of the deep-well-plates, containing 300 µL BMD1 per well, and incubated at 28° C. with 320 rpm for 36-60 hours.

After this incubation they were induced by methanol adding 250 µL of BMM2 per well and incubated again. 12, 24 and 36 hours later 50 µL of BMM10 were added per well.

12 hours after the last addition of BMM10 the deep-well plates were centrifuged for 10 minutes at high speed. The supernatant containing the secreted enzyme was used for the assays described herein.

One Day Induction

The one-day induction protocol was following the same procedure as the two-day induction protocol but the cells were only induced for the first two times, followed by the harvest already on the next day.

Flask Cultivation

The Flask cultivation was carried out as follows:

450 mL of BMD1% were inoculated with the transformed *Pichia pastoris* as described above in a 2.5 L Ultra Yield Flask (UYF).

The flasks were incubated for 3 days at 28° C. and 100 rpm.

After incubation the induction was started with 50 mL of BMM1). Every 12 hours 5 mL of 100% methanol were added for three times.

The day after the last induction the culture was harvested by centrifugation in 500 mL tubes for 15 minutes at 8,000 rpm. The enzyme was in the supernatant. Cells were removed by centrifugation. The supernatants were filtered through a membrane with a pore size of 0.45 µm and stored at 4° C.

The concentration of the enzyme in the supernatant was evaluated by centrifugation with Vivaspin columns with a 10 kD cutoff.

Bioreactor Cultivation

To scale up enzyme production Sartorius 5 L bioreactors were used for cultivations.

The bioreactor cultivations were based on Invitrogen's™ "*Pichia* Fermentation Process Guidelines". In detail the cultivation was done as follows:

The pre-culture I, consisting of 50 mL BMGY in 250 mL baffled flask with some cell material of transformants grown on an agar plate, was incubated at 110 rpm, 28° C. and about 50% humidity for about 60 hours.

After the incubation an aliquot of preculture I was used to inoculate the pre-culture II (200 mL BMGY in 1 L baffled flask) to an OD600 of 3.0. After about four hours the 3.5 L BSM medium in the 5 L bioreactor was inoculated to an OD600 of about 1.0 (as measured with the same photometer). The glycerol batch phase lasted for 22 hours until the entire carbon source was consumed.

The standard conditions in a non-optimized bioreactor cultivation was: 28° C., pH 6.0, min. stirring at 500 rpm, min. dO2 of 30% (cascade setting) and 4 L/min airflow.

During the glycerol fed-batch phase the culture was fed constantly with 26 mL/h/L (L . . . liter of start volume; 3.5 L:91 mL/h) 50% glycerol with PTM1 and biotin (both 12 mL/L fed-batch medium) for 6 hours. During night the culture was fed with 2.6 mL/h/L fed-batch medium.

On the next morning the glycerol-feed was turned off and after 30 minutes 100% methanol was added to the bioreactor culture to a final methanol concentration of 1%. After consumption a constant methanol feed was set to 3 mL/h/L (L . . . liter of start volume; 3.5 L:10.5 mL/h) pure methanol (without PTM1 or biotin). This flow rate was kept for 30 hours.

Finally, the culture was harvested in 1 L centrifuge tubes at 8,000 rpm and the supernatant was transferred into clean bottles and stored at 4° C. until future use.

Activity Assays

Well described standard assays for measuring the activity of unspecific peroxygenases were applied for proving the peroxidase and/or peroxygenase activities of the supernatants of the performed cultivations.

ABTS Assay

The ABTS assay was carried out analogously as described by Morawski et al. (2000) for horse radish peroxidase (HRP). The ABTS assay was performed with variable parameters, including varying concentration of the buffer at different pH values.

TABLE 2

| Assay Solution | |
|---|---|
| Variable parameters | Range used |
| supernatant | 2-15 µL |
| buffer | NaOAc or citrate-phosphate-buffer |
| pH value of buffer | 2.5-7.0 |
| molarity of buffer | 100-200 mM |

For one 96-well plate 20 mL assay solution were prepared. Therefore 1 mL 20×ABTS stock solution (440 mg 2,2'-azino-bis(3-ethylbenzothiazoline-6-sulfonic acid) in 50 mL 50 mM NaOAc) was mixed with 19 mL buffer and 1.75 µL 30% $H_2O_2$. The assay solution was kept on ice.

15 µL of the supernatant was mixed with 140 µL of the assay solution and the increase in absorption at 405 nm was measured with the plate reader.

The first screening was carried out with a buffer concentration of 50 mM and pH values of 3.5, 4.5 and 5.5 respectively. As benchmark the PaDa1 mutant (of AaeUPO1) was measured under the same conditions as the new constructs. The new UPO constructs were measured after secretion employing their natural signal peptide as well as the alternative mating factor alpha signal peptide. The measurement was carried out for 15 minutes.

2,6-DMP Assay

The 2,6-DMP (2,6-dimethoxyphenol) assay was done similar to the assay described by E. Breslmayr et al. (2018) for lytic polysaccharide monooxygenases and by P. Molina-Espeja et al. (2016). The 2,6-DMP assay was performed with potassium phosphate (KPi) buffer pH 7.0.

For one 96-well plate 20 mL assay solution were prepared. Therefore 2 mL 2,6-DMP stock solution (100 mM, 154 mg in 10 mL dd$H_2O$, heated to 60° C. for better solubility) was mixed with 2 mL KPi buffer (1.0 M, pH 7.0), 16 mL dd$H_2O$ and 0.5 µL 33% $H_2O_2$. The assay solution was kept on ice.

15 µL of the supernatant was mixed with 185 µL of the assay solution and the increase in absorption at 469 nm was measured with the plate reader. The measurement was carried out for 9 minutes.

Naphthalene Assay

This assay for aromatic peroxygenases was done similar to the Naphthalene-Fast Blue-Assay described by Gröbe et al. (2011). For one 96-well plate 20 mL of assay solution were prepared.

TABLE 3

| Assay Solution | |
| --- | --- |
| Variable parameters | Range used |
| supernatant | 2-15 µL |
| buffer | NaOAc or citrate-phosphate-buffer |
| pH value of buffer | 4.5-5.5 |
| molarity of buffer | 100-200 mM |
| Naphthalene stock solution | 1-2 mL |
| Fast Blue stock solution | 1-2 mL |

4 mM naphthalene stock solution: 5 mg naphthalene, in 10 mL acetone 2 mM Fast Blue stock solution: 9.5 mg Fast Blue B salt/10 mL dH$_2$O For one 96-well plate 20 mL assay solution were prepared, containing 10 mL citrate-phosphate-buffer, 1-2 mL 4 mM naphthalene stock solution and the same amount of 2 mM Fast Blue stock, 2 µL 30% H$_2$O$_2$. Then dH$_2$O was added to obtain a final volume of 20 mL.

30 µL of the supernatant was mixed with 150 µL of assay solution and the increase in absorption at 520 nm was measured with plate reader.

Filter Assay

The filter assay was done similar to the ABTS assay described above. For proof of concept, HRP secreting *Pichia pastoris* BSYBG11 strains were used as positive control and wild type BSYBG11 strains as negative control.

The positive and negative controls were streaked out on agar plates containing Zeocin to get single colonies. The plates also contained methanol for induction. A filter paper was laid on the plate, so that the colonies stick to it. This filter was transferred to an empty petri dish with the colonies looking down. This should help to keep the colonies where they are, not washing them off. Then 100 µL of assay solution, as described above, where carefully pipetted onto the filter. The assay was incubated at room temperature and controlled every five minutes.

After the concept was proven by seeing green color development due to ABTS oxidation on agar plates by HRP producing cells, the same assay was conducted with UPO 1, 12 and 17 secreting *P. pastoris* BSYBG11 as positive control and wild type *P. pastoris* BSYBG11 as negative control.

Plate Assay

It was assumed that a colony secreting an active UPO would be surrounded by a greenish halo, similar to the filter paper assay. To have a proof of concept the plate assay was carried out with an HRP (horse radish peroxidase) secreting *P. pastoris* BSYBG11 transformant as positive control and a *P. pastoris* BSYBG11 wild type as negative control.

The plates where made with buffered minimal medium containing 1% of methanol, sorbitol or glucose respectively. H$_2$O$_2$, 30% (Table 5) was added to final concentrations of 43.3 µL*L-1, 87.5 µL*L-1 and 175 µL*L-1, respectively.

The positive and negative controls were streaked out and the plates where incubated at 28° C. for two days. After that time single colonies should be formed. The plates were evaluated by visual inspection.

Volumetric Peroxidase Activity

Peroxidase activity measurements were performed in plate readers, normalizing by respective assay volumes in the plates. For the calculation of units, the layer thickness was calculated according to Formula 1. In Formula 1 the "h" value corresponds to the layer thickness "d".

Formula 1: The layer thickness was calculated depending on the total volume per well.

$$\pi * [(h^3 * \tan^2 \varphi)/3 * h^2 * r * \tan \varphi * r^2] - V = 0$$

After determining the layer thickness, the units were calculated with Formula 2.

Formula 2: Calculation of volumetric peroxidase activity.

$$U = (\Delta A \Delta t^{-1} * V_{tot} * D)/(v_{sample} * \varepsilon_{405} * d)$$

U Units per mL [µmol*ml-1*min-1]
Vtot total assay volume [mL]
$\Delta A \Delta t^{-1}$ change in absorption per time [$\Delta A(405) * \text{min}^{-1}$]
D dilution factor of the sample
d layer thickness [cm]
vsample sample volume [mL]
ε405 extinction coefficient at 405 nm [36,000 mL *µmol-1*cm-1]

Bioconversions

As there are many known substrates that are converted by UPOs just a few exemplifying substrates were tested to proof that the new UPOs are active and able to convert those model substrates. To verify possible bio-conversions HPLC measurements were carried out.

To be able to carry out HPLC measurement including control samples also supernatants from *P. pastoris* BSYBG11 cultures, grown as negative control and even pure substrate in assay buffer (without enzymes) were applied on the 96-well plate. Furthermore, transformed strains expressing two other intracellular enzymes, human Cytochrome P4502C9 and 3A4, were used as benchmark and control.

The following substrates of interest have been tested: Chlorzoxazone, testosterone, clopidogrel, diclofenac, dextromethorphan, estriol, ethionamide, ibuprofen, lidocaine, and moclobemide.

Bioconversions were carried out in 96-well deep well plates. The assay buffer consisted of 20 mL of 200 mM citrate-phosphate buffer at pH 4.7 containing 2 µL of 30% (w/w) H$_2$O$_2$.

The refreshing buffer consisted of 20 mL of 200 mM citrate-phosphate buffer at pH 4.7 containing 200 µL of 30% (w/w) H$_2$O$_2$.

Each well contained 100 µL of supernatant, 100 µL of assay buffer and 4 µL of stock substrate solution (100 mM). The deep well plates were incubated at 28° C. and 320 rpm for 15 hours. 0.5 µL of refreshing buffer were added per well. The deep well plates were re-incubated for another 6 hours. To stop the conversion 150 µL of an acetonitrile/methanol (1:1) mixture was added.

For sample preparation, the polypropylene microtiter plates were centrifuged for 20 minutes at 4000 rpm and 4° C. 100 µL of reaction supernatant was transferred into a fresh polypropylene microtiter plate. The new plate was used for measurements by HPLC.

The applied HPLC parameters are listed in Table 4.

The analyses were done on an Agilent 1200 series HPLC system (Agilent technologies, Santa Clara, California, USA) coupled with a mass spectrometer detector (MSD) containing an electron spray ionization unit.

TABLE 4

| | HPLC-MS parameters | |
| --- | --- | --- |
| | Parameters | Column (Kinetex ® 2.6 µm C18 100 Å, LC Column 50 × 4.6 mm) |
| LC | Injection volume (µL) | 10 |
| | Flow rate (ml min$^{-1}$) | 1 |
| | Column temp. (° C.) | 25 |
| | Solvent A1 | H$_2$O-0.1% acetic acid |
| | Solvent B2 | ACN |
| API-ES | Gas temp. (° C.) | 350 |
| | Gas flow (L min$^{-1}$) | 12 |
| | Nebulizer (psi) | 35 |
| | Quad temp. (° C.) | 350 |
| | Polarity | Positive |

Materials
Chemicals

TABLE 5

List of used chemicals.

| Name | Provider |
|---|---|
| LB-Medium | Carl Roth, GmbH, Karlsruhe, Germany |
| 10x FastDigest Buffer | Thermo Scientific Inc., Massachusetts, USA |
| 5x Q5 ® Reaction Buffer | New England Biolabs, Ipswich, MA, United States |
| ABTS | Sigma-Aldrich Chemie GmbH, Missouri, USA |
| Agar-Agar | Carl Roth, GmbH, Karlsruhe, Germany |
| BD Bacto ™ yeast extract | Becton, Dickinson and Company, Sparks, MD, USA |
| Biotin | Sigma-Aldrich Chemie GmbH, Missouri, USA |
| Biozym LE agarose | Biozym Scientific, Hessisch Oldendorf, Germany |
| dATP, dGTP (10 mM) | Thermo Scientific Inc., Massachusetts, USA |
| dCTP, dTTP (20 mM) | Thermo Scientific Inc., Massachusetts, USA |
| D-Glucose-monohydrate | Carl Roth, GmbH, Karlsruhe, Germany |
| dNTPs | Thermo Scientific Inc., Massachusetts, USA |
| D-Sorbit | Carl Roth, GmbH, Karlsruhe, Germany |
| FastBlue B | Sigma-Aldrich Chemie GmbH, Missouri, USA |
| FastDigest Green Buffer | Thermo Scientific Inc., Massachusetts, USA |
| Hydrogen peroxide | Carl Roth, GmbH, Karlsruhe, Germany |
| $K_2HPO_4$ | Carl Roth, GmbH, Karlsruhe, Germany |
| $KH_2PO_4$ | Carl Roth, GmbH, Karlsruhe, Germany |
| Methanol | Sigma-Aldrich Chemie GmbH, Missouri, USA |
| $MgCl_2$ (25 mM) | Thermo Scientific Inc., Massachusetts, USA |
| Naphthalene | Sigma-Aldrich Chemie GmbH, Missouri, USA |
| Trichloroacetic acid (TCA) | Sigma-Aldrich Chemie GmbH, Missouri, USA |

Host Strains

For the transformation with linearized integrative plasmid DNA vectors containing putative new UPO gene sequences the *Pichia pastoris* platform strain BSYBG11 was used. Compared to the wild type strain BSYBg10, this strain has an AOX1 gene knock out leading to a slow growth phenotype, when methanol is used as carbon source.

TABLE 6

Information on the origin strains used to generate Pichia pastoris biocatalysts.

| | Species/Host strain: | |
|---|---|---|
| | *Komagataella phaffii* BSYBG10 (Syn.: *Pichia pastoris*) | *Komagataella phaffii* BSYBG11 (Syn.: *Pichia pastoris*) |
| BT Culture collection number of IMBT at TU Graz | 7287 | 7288 |

Media, Buffers and Solutions

Media used during the thesis are conventional media. If not mentioned else the amounts are given for 1 L of media and the media is autoclaved.

Plasmids

Plasmids were kindly provided by Bisy GmbH (Austria) and are listed in Table 7.

TABLE 7

Plasmids.

| Plasmid | Promoter | Additional Information |
|---|---|---|
| pBSY3Z | PDC | Contains *P. pastoris* is CTA1 promoter |
| pBSY3S1Z | PDC | contains additional coding region for short variant of mating factor alpha signal |
| pBSY5Z | PDF | Contains *Hansenula polymorpha* FMD promoter variant |
| PBSY5S1Z | PDF | contains additional coding region for short variant of mating factor alpha signal |

Results and Discussion

Evaluation of Synthetic Heme Thiolate Peroxygenase Genes

After vector digestion with LguI (SapI) the stuffer of the vectors pBSY3Z and pBSY3S1Z was cut out. For the vector pBSY3Z also a control digest was performed with EcoRI. Inserts coding for the peroxygenases were inserted into the vector backbones by recombination cloning and transformation of *E. coli* by electroporation. After plasmid isolation sequences were evaluated by Sanger sequencing. Table 8 shows the results of the sequence evaluation of cloned UPO and CPO genes synthesized by TWIST. In total 24 genes were sequenced, 19 of them proved to be correct. This corresponds to a validity of 79.17%.

The table 8 shows how many genes of each ordered construct were sequenced and how many of them where confirmed.

TABLE 8

Evaluation of synthetic genes.

| Ordered Gene | Correct genes | Genes sequenced |
|---|---|---|
| UPO 2 | 1 | 1 |
| UPO 4 | 1 | 1 |
| UPO 5 | 1 | 3 |
| UPO 6 | 2 | 2 |
| UPO 7 | 2 | 2 |
| UPO 8 | 1 | 2 |
| UPO 9 | 2 | 3 |
| UPO 10 | 2 | 2 |
| UPO 11 | 1 | 2 |
| UPO 13 | 1 | 1 |
| UPO 14 | 1 | 1 |
| UPO 16 | 1 | 1 |
| UPO 17 | 1 | 1 |
| UPO 18 | 1 | 1 |
| CPO 20 | 1 | 1 |
| Total | 19 | 24 |

The pairwise alignments show the identity of the selected new putative UPO candidates to previously known sequences. The alignment was made with Clustal Omega using the full available sequence length. The identity shows the percentage of amino acid sequence identity as given by the "percent identity matrix" created by clustal2.1. An overview of the identities can be found in Table 9 and Table 10.

Due to very low sequence identity the analysis performed with the CPO sequence (CPO19 & 20) is not included in this table.

TABLE 9

Identities of the new sequences with some previously described sequences in the NCBI patent sequence database "pat".

|  | Agrocybe aegerita GM831938 | Agrocybe aegerita GM831940 | laccaria bicolor GM831942 | Coprinopsis cinerea okayama7#130_ GM831944 | Coprinopsis cinerea okayama7#130 GM831946 | Coprinopsis cinerea okayama7#130 GM831948 | Coprinopsis cinerea okayama7#130 GM831950 | Coprinellus radians GM831952 |
|---|---|---|---|---|---|---|---|---|
| UPO 2 | 66.58 | 69.73 | 69.09 | 63.27 | 60.40 | 60.22 | 59.64 | 64.32 |
| UPO 3 | 59.79 | 61.46 | 62.63 | 58.11 | 55.91 | 56.12 | 57.14 | 62.11 |
| UPO 4 | 63.41 | 62.6 | 67.74 | 58.33 | 56.2 | 56.18 | 62.35 | 63.44 |
| UPO 5 | 63.51 | 63.69 | 94.41 | 59.68 | 56.69 | 57.95 | 60.12 | 67.84 |
| UPO 6 | 59.57 | 61.35 | 71.73 | 59.68 | 57.68 | 57.68 | 60.24 | 63.44 |
| UPO 7 | 60.27 | 60.16 | 69.33 | 57.8 | 58.6 | 54.72 | 57.1 | 63.88 |
| UPO 8 | 57.84 | 59.62 | 68.00 | 54.84 | 56.81 | 55.80 | 57.40 | 62.11 |
| UPO 9 | 26.02 | 27.31 | 28.78 | 27.68 | 27.52 | 27.04 | 25.19 | 27.67 |
| UPO 10 | 28.79 | 29.12 | 31.42 | 27.59 | 28.79 | 30.27 | 31.01 | 32.20 |
| UPO 11 | 33.33 | 32.05 | 28.96 | 29.89 | 29.25 | 30.74 | 31.52 | 30.88 |
| UPO 12 | 30.95 | 29.88 | 30.20 | 29.88 | 32.74 | 31.10 | 30.31 | 28.78 |
| UPO 13 | 27.99 | 26.67 | 28.21 | 25.38 | 29.96 | 27.90 | 29.24 | 29.47 |
| UPO 14 | 28.38 | 28.96 | 28.05 | 28.64 | 29.63 | 26.85 | 26.39 | 29.59 |
| UPO 15 | 57.72 | 57.18 | 59.25 | 56.91 | 58.02 | 56.37 | 59.39 | 64.76 |
| UPO 16 | 58.74 | 58.47 | 57.84 | 56.13 | 54.12 | 59.29 | 62.39 | 64.32 |
| UPO 17 | 28.63 | 25.68 | 26.46 | 26.06 | 24.89 | 25.68 | 27.86 | 24.64 |
| UPO 18 | 57.18 | 59.35 | 59.19 | 57.14 | 58.43 | 55.68 | 58.79 | 63.00 |

TABLE 10

Identities of the new sequences with some previously described patent sequences

|  | Coprinellus radians GM831954 | Sclerotinia sclerotiorum | Aspergillus carbonarius | Humicola insolens | Myceliophthora hinnulea | Pestalotiopsis virgatula | Chaetomium yirescens | Daldinia caldariorum |
|---|---|---|---|---|---|---|---|---|
| UPO 2 | 45.19 | 28.21 | 30.35 | 29.57 | 30.56 | 30.80 | 22.88 | 25.67 |
| UPO 3 | 41.35 | 28.15 | 30.59 | 29.41 | 30.35 | 28.93 | 25.38 | 27.80 |
| UPO 4 | 44.66 | 27.10 | 28.02 | 31.13 | 29.96 | 29.25 | 23.33 | 29.02 |
| UPO 5 | 45.19 | 29.92 | 30.59 | 32.12 | 30.35 | 28.23 | 26.22 | 26.25 |
| UPO 6 | 43.81 | 26.15 | 27.85 | 30.71 | 29.07 | 29.88 | 26.48 | 25.10 |
| UPO 7 | 36.63 | 29.01 | 31.37 | 32.12 | 29.30 | 30.28 | 27.56 | 29.57 |
| UPO 8 | 37.86 | 28.24 | 30.47 | 31.18 | 29.48 | 27.71 | 25.91 | 27.41 |
| UPO 9 | 26.67 | 79.93 | 42.08 | 42.19 | 40.31 | 42.86 | 28.74 | 39.84 |
| UPO 10 | 21.57 | 41.57 | 60.87 | 53.12 | 53.97 | 56.47 | 29.96 | 50.98 |
| UPO 11 | 23.08 | 41.83 | 60.47 | 53.39 | 54.76 | 57.65 | 31.47 | 52.55 |
| UPO 12 | 19.59 | 39.62 | 50.98 | 50.39 | 51.18 | 54.80 | 31.62 | 63.39 |
| UPO 13 | 27.94 | 42.58 | 49.80 | 48.87 | 61.30 | 52.78 | 31.06 | 48.85 |
| UPO 14 | 23.53 | 37.33 | 46.95 | 50.91 | 72.00 | 52.27 | 28.44 | 44.14 |
| UPO 15 | 44.12 | 23.48 | 26.56 | 28.35 | 28.29 | 27.69 | 23.40 | 24.31 |
| UPO 16 | 44.00 | 25.58 | 30.59 | 30.20 | 27.52 | 27.67 | 27.07 | 25.97 |
| UPO 17 | 21.69 | 28.14 | 35.42 | 34.25 | 30.65 | 30.04 | 71.97 | 32.03 |
| UPO 18 | 45.10 | 27.69 | 27.52 | 30.80 | 28.40 | 26.59 | 24.07 | 24.61 |

ABTS Assays
Activity Landscapes in 100 mM Buffer

All activity landscapes formed by measured activities of individual transformants were directly done with samples (culture supernatants) from deep well plate cultivation. The slope of absorption was in all cases calculated with Microsoft Excel's "slope( )" function and is equivalent to $1.4*\Delta ABS*min^{-1}$. The measurement was done with the plate reader.

In FIG. 1 the landscapes of the PaDa1 mutant transformants (mutant of AaeUPO1) at pH 3.5, 4.5 and 5.5 were compared and showed a maximum of conversion at pH 4.5.

Figure 2:
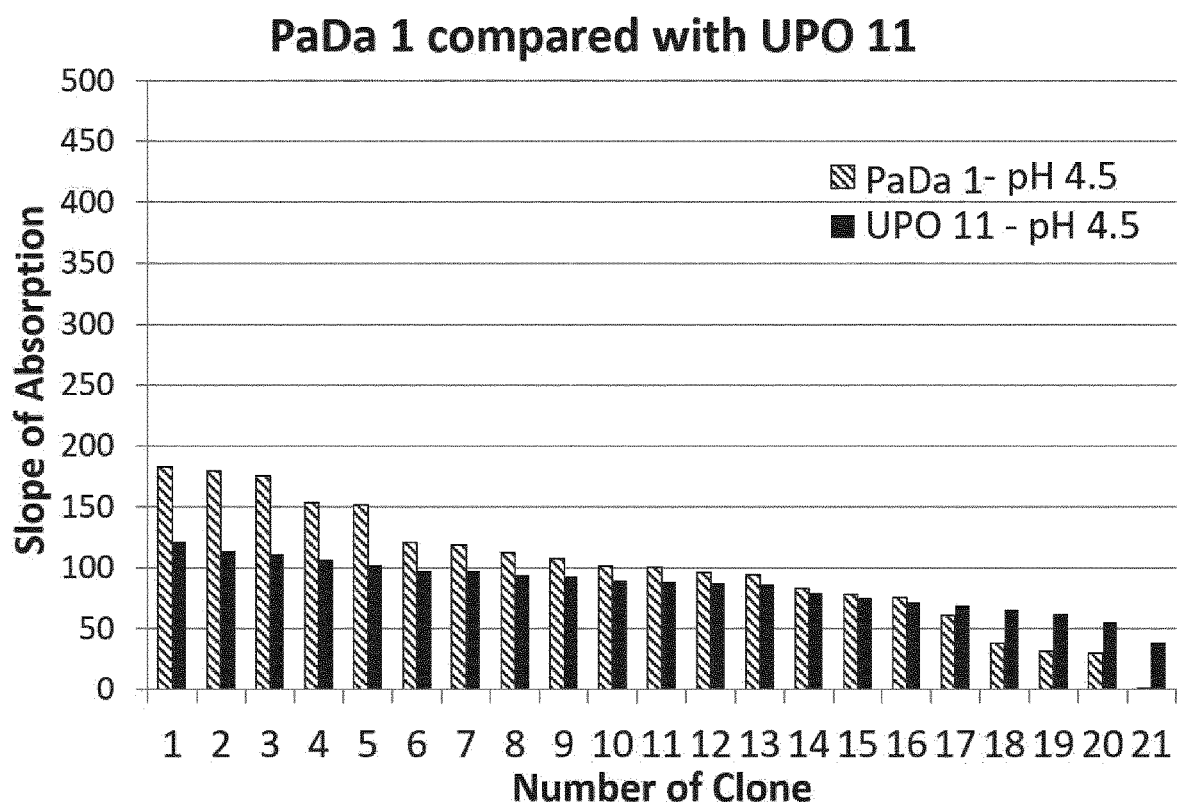
FIG. 2: Comparison of the slope of absorption of the PaDaI mutant of AaeUPO1 variant PaDa1 (UPO1) and UPO 11 both at pH 4.5.

FIG. 2 shows the measurement results of AaeUPO 1 mutant PaDa1 (indicated as UPO1 mut) as well as UPO 11 at pH 4.5. Supernatants of UPO 1 clones converted ABTS faster than UPO 11, nonetheless also the new wt enzyme UPO 11 converted ABTS very well, indicating good expression of the recombinant protein.

Figure 3:
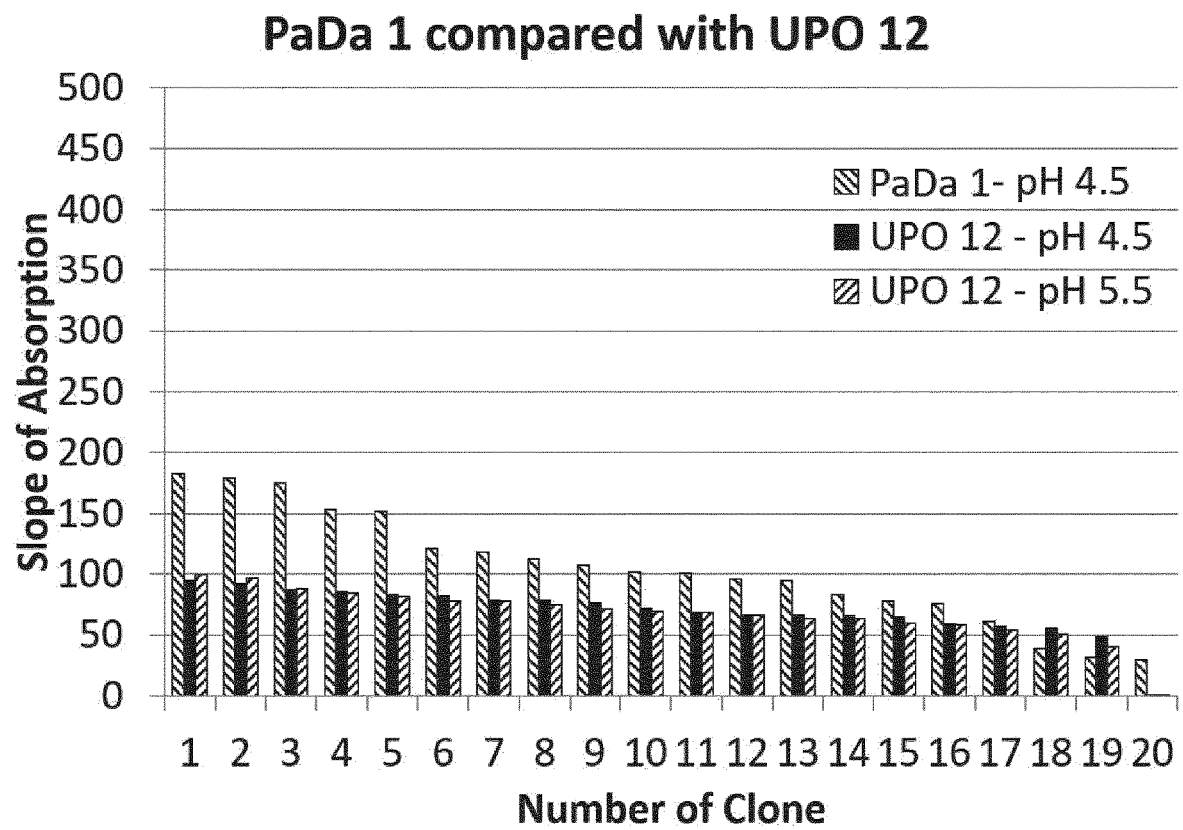
FIG. 3: Comparison of the slope of absorption of the PaDaI mutant of AaeUPO1 variant PaDa1 (UPO1) and UPO 12, both at pH 4.5. Also, UPO 12 at pH 5.5 is compared and shown.

UPO 12 behaved similar to UPO 11 in ABTS peroxidase assays as shown in FIG. 3. In primary screenings UPO 11 showed a maximum conversion at pH 4.5 when tested at pH values 3.5, 4.5 and 5.5, UPO 12 in comparison showed similar behavior at pH 4.5 and 5.5, indicating a higher robustness of activity at different pH than the AaeUPO1 variant.

Figure 4:
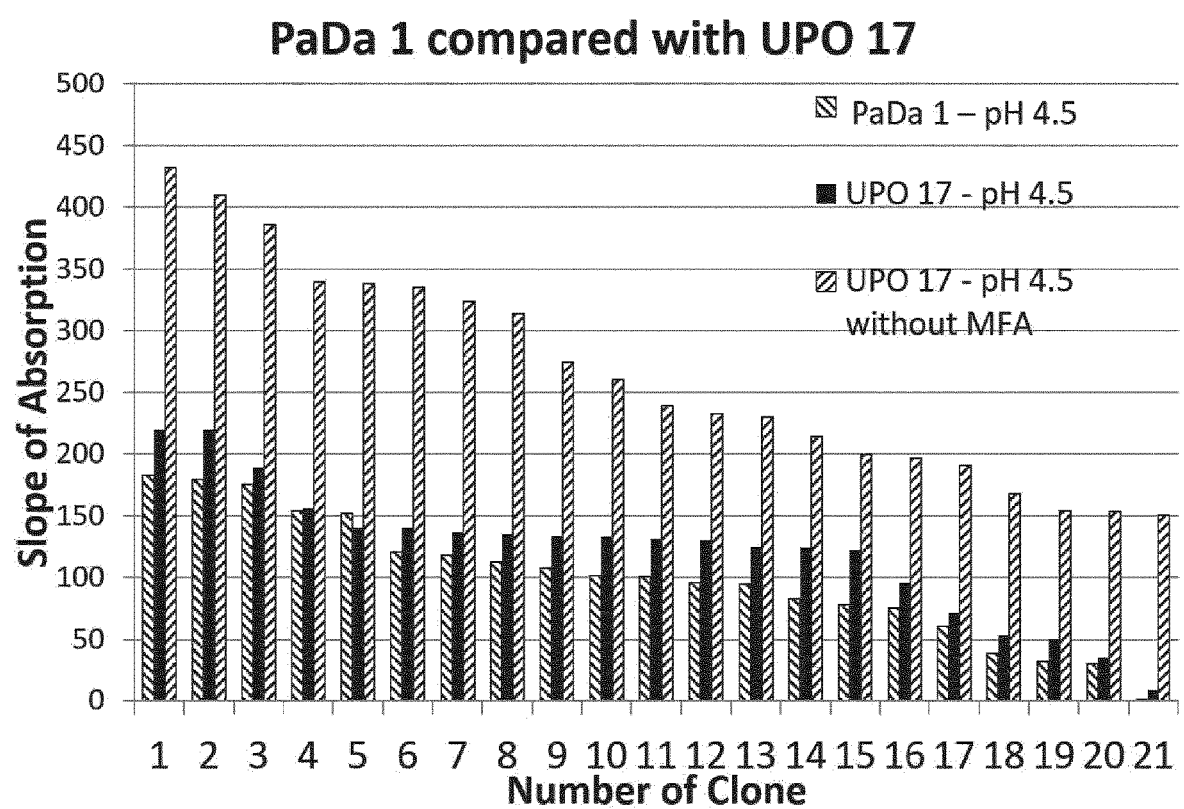
FIG. 4: Comparison of the slope of absorption of the PaDaI mutant, UPO 17 and UPO 17 without mating factor alpha but with the native signal. All constructs were measured at pH 4.5.

FIG. 4 shows the comparison of UPO 1, UPO 17 and UPO 17 without additional mating factor alpha—but the given native signal sequence. This given signal sequence is from *Podospora anserina* and increased the conversion of ABTS around 2-fold compared to the construct containing the short *Saccharomyces cerevisiae*'s mating factor alpha signal.

Figure 5:
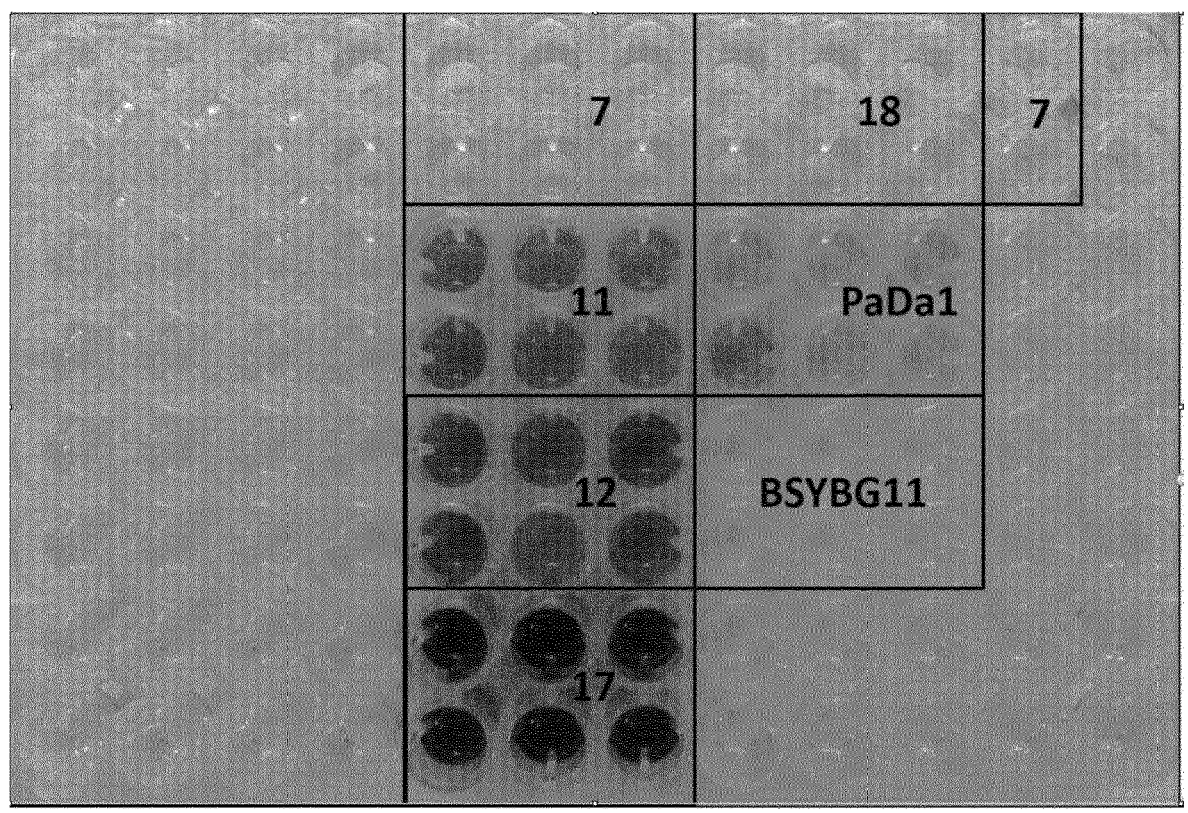
FIG. 5: ABTS peroxidase assay to compare PaDaI mutant of AaeUPO1 containing the evolved signal peptide for secretion with the PaDaI mutant of AaeUPO1 containing a native signal as well as with the UPOs 7, 8, 11, 12 (linked to the short mating factor alpha signal) and UPO17 with its native signal peptide. As a control BSYBG11 was applied on the same microtiter plate. A dark color can be observed for UPO 17, a little less dark for UPO 12 and 11, indicating either high specific peroxidase activity and/or high expression especially for UPO17, but also for other UPOs. The PaDaI mutant of AaeUPO1 with evolved signal showed low intensity coloring (indicating low expression in this specific experiment), the PaDaI mutant of AaeUPO1 with the native signal sequence showed no coloring that could be observed with the eye. UPOs 7 and 18 as well as empty control strain BSYBG11 also showed no coloring in the peroxidase assay. The assay solution was performed in 200 mM citrate buffer at pH 4.5.

To confirm that the AaeUPO 1 with short mating factor alpha signal is converting ABTS better than with the native signal peptide was tested with given settings and the described expression system. As shown in FIG. 5 there was no mentionable activity measured for UPO 1 with the native signal peptide.

Furthermore, in this specific experiment the constructs containing PaDa 1 with mating factor alpha signal were converting ABTS poorly. Nonetheless, at least the mating factor alpha signal containing constructs were active and behaved better than the ones with native signal peptides.

Constructs with Measurable Activity in the Rescreening

TABLE 11

Results of the rescreening at pH 4.5 using the ABTS based peroxidase assay, indicating functional expression.

| Construct | Clone | ΔABS(405 nm)/min |
|---|---|---|
| UPO 17 | 17-A0 | 349.3 |
| UPO 17 | 17-B0 | 291.7 |
| UPO 17 | 17-C0 | 285.2 |
| UPO 12 | 12-A0 | 68.8 |
| UPO 12 | 12-B0 | 68.5 |
| PaDa 1 | 1-A0 | 66.8 |
| UPO 12 | 12-C0 | 66.5 |
| UPO 11 | 11-A0 | 65.2 |
| UPO 11 | 11-B0 | 64.1 |
| UPO 11 | 11-C0 | 62.1 |
| PaDa 1 | 1-B0 | 57.9 |
| PaDa 1 | 1-C0 | 57.6 |
| CPO 19* | | 1.2 |
| CPO 19* | | 1.2 |
| CPO 19* | | 1.0 |
| UPO 3 | 3-A0 | 0.9 |
| UPO 2 | 2-A0 | 0.7 |
| UPO 15 | 15-A0 | 0.7 |
| UPO 15 | 15-B0 | 0.6 |
| UPO 5 | 5-A0 | 0.6 |
| UPO 3 | 3-B0 | 0.6 |
| UPO 15 | 15-C0 | 0.5 |
| UPO 4 | 4-A0 | 0.4 |
| UPO 2 | 2-B0 | 0.4 |
| UPO 3 | 3-C0 | 0.3 |
| UPO 4 | 4-B0 | 0.2 |
| UPO 16 | 16-A0 | 0.2 |
| Negative control/BSYBG 11 without integrated expression vector | | 0.1 |

*Data from the primary screening

The Table shows the transformants that where most active in the rescreening with their medium change in absorption per minute, measured over 13 minutes.

As can be seen in Table 11 the rescreening of the most promising clones with the ABTS assay was successful and indicated peroxidase activity and functional expression for all tested genes. UPO17 showed higher activity than the evolved AaeUPO1 variant. Surprisingly also CPO transformants showed activity, indicating functional expression of CfuCPO by *P. pastoris*.

Assays after Bioreactor Cultivation

ABTS Assay

Constructs under the PDC Promoter showed increased activity after the bioreactor cultivation compared to 96-deepwell plate cultivation, as shown in Table 12. Surprisingly the activity of UPO 17 was far lower than the activities of the UPOs 11 and 12, indicating possible enzyme instabilities caused by long term cultivation. Compared to the benchmark, AaeUPO 1 variant PaDa1, activities up to 355-fold higher were seen.

TABLE 12

The table lists the constructs cultivated in the bioreactor and the units per milliliter unconcentrated supernatant, measured with the ABTS assay. Furthermore, a comparison of the new UPOs compared to the benchmark, AaeUPO1 variant PaDa1 is listed.

| Construct | U * ml$^{-1}$ | Peroxidase activity compared to PaDa1 |
|---|---|---|
| PaDa 1 | 0.13 | 1 |
| UPO 11 | 21.55 | 166-fold |
| UPO 12 | 46.12 | 355-fold |
| UPO 17 | 6.61 | 51-fold |

Determined by the Bradford Assay the protein concentrations of the supernatant are as listed in Table 13. Protein concentrations in the supernatant from non-optimized bioreactor cultivations were equal or mostly higher than for the benchmark clone, which was also made with the new expression vectors based on the PDC promoter.

TABLE 13

Protein concentrations of the supernatant of the bioreactor cultivations as a result of Bradford Assays. The amount of enzyme found in the supernatant of the cultivation of the PaDa1 expression clone confirmed previous data of Molina et al (2015)

| Construct | mg * mL$^{-1}$ |
|---|---|
| PaDa 1 | 0.1769 |
| UPO 11 | 0.2455 |
| UPO 12 | 0.2031 |
| UPO 17 | 0.1651 |

Naphthalene—Fast-Blue Assays

Figure 6:
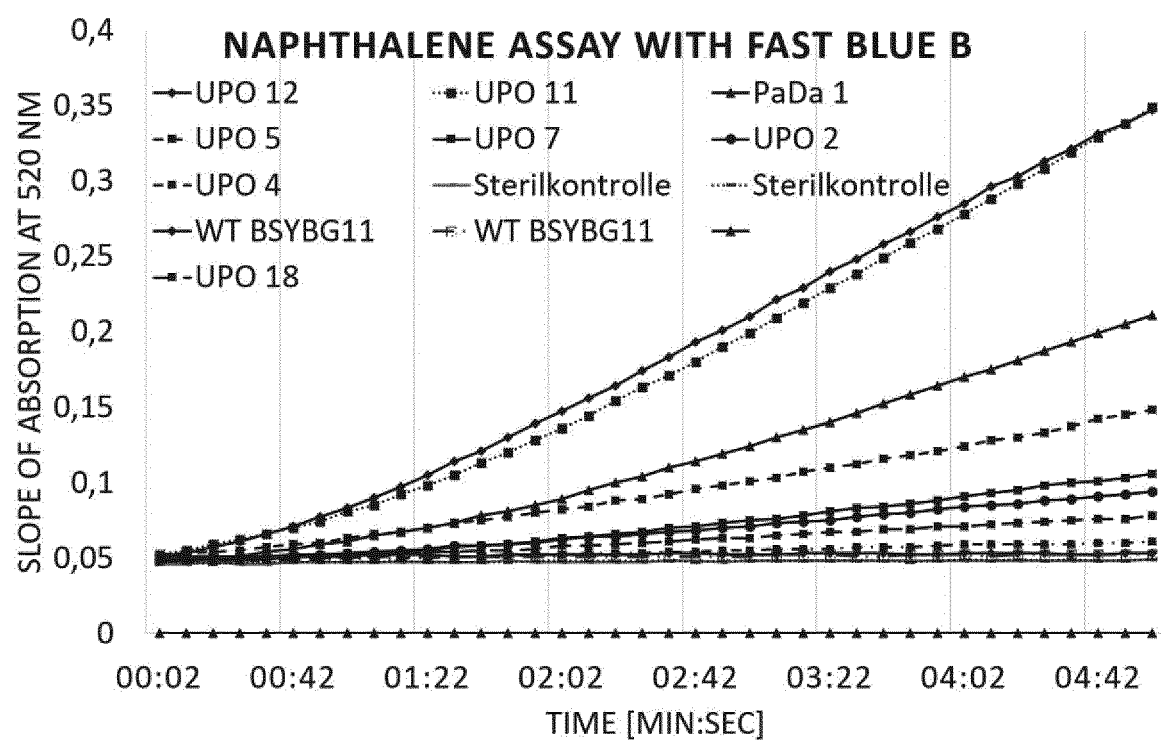
FIG. 6: Diagram of different UPOs converting naphthalene by oxygenation, followed by hydroxy naphthol detection with fast blue, measured photometrically by absorption at 520 nm over 5 minutes.

The naphthalene assay is suitable to measure peroxygenase activity. As shown in FIG. 6, there are, beneath UPO 1, six UPOs that clearly showed activity in this assay. Two of the new constructs, UPO 12 and UPO 11, converted the substrate nearly twice as fast as the known benchmark. UPO 1.

The rescreened clones that showed activity in the Naphthalene-Fast Blue-Assay are listed in Table 14, including ΔABS/min values at 520 nm.

TABLE 14

The table lists the clones that were active at the rescreening at the naphthalene-fast blue Assay and their average change in absorption per minute at a measurement over 13 minutes.

| Construct | Clone | ΔABS(520 nm)/min |
|---|---|---|
| UPO 12 | 12-B0 | 62.7 |
| UPO 12 | 12-C0 | 62.0 |
| UPO 12 | 12-A0 | 61.6 |
| UPO 11 | 11-A0 | 59.3 |
| UPO 11 | 11-C0 | 59.2 |
| UPO 11 | 11-B0 | 55.5 |
| PaDa 1 | 1-B0 | 31.6 |
| PaDa 1 | 1-C0 | 28.2 |
| PaDa 1 | 1-A0 | 24.2 |
| UPO 5 | 5-A0 | 19.0 |
| UPO 5 | 5-C0 | 18.2 |
| UPO 5 | 5-B0 | 15.1 |
| UPO 7 | 7-A0 | 11.2 |
| UPO 2 | 2-A0 | 8.9 |
| UPO 2 | 2-B0 | 8.5 |
| UPO 7 | 7-B0 | 8.5 |
| UPO 7 | 7-C0 | 8.0 |
| UPO 2 | 2-C0 | 7.1 |
| UPO 18 | 18-A0 | 6.4 |
| UPO 18 | 18-B0 | 5.5 |

TABLE 14-continued

The table lists the clones that were active at the rescreening at the naphthalene-fast blue Assay and their average change in absorption per minute at a measurement over 13 minutes.

| Construct | Clone | ΔABS(520 nm)/min |
|---|---|---|
| UPO 18 | 18-C0 | 5.0 |
| UPO 4 | 4-B0 | 2.8 |
| UPO 4 | 4-C0 | 2.8 |
| UPO 4 | 4-A0 | 2.5 |
| UPO 9 | 9-1 | 1.5 |
| UPO 16 | 16-A0 | 0.9 |
| UPO 16 | 16-C0 | 0.8 |
| UPO 8 | 8-1 | 0.7 |
| UPO 9 | 9-2 | 0.7 |
| UPO 9 | 9-3 | 0.7 |
| UPO 10 | 10-1 | 0.7 |
| UPO 14 | 14-1 | 0.7 |
| UPO 15 | 15-A0 | 0.6 |
| UPO 14 | 14-2 | 0.6 |
| Negative control/BSYBG 11 | | 0.5 |

Clear naphthalene oxidation activity was found for most tested expression clones but not all of them. For UPO14 this might be explained by the fact that the used database sequence was wrongly annotated and the used was not correct according to Kiebist et al. (2017). Surprisingly new recombinant UPOs with a higher peroxygenase/peroxidase activity ration were identified by these rescreening experiments using the ABTS and naphthalene assay, indicating the high potential of the new recombinant heme thiolate peroxygenases and the diversity of catalytic properties with diverse substrates and chemical reactions.

Filter Assay

In the filter assay with horse radish peroxidase the promising results were obtained. A greenish zone was visible around every active colony.

Peroxidase Plate Assay

After incubation the plates were visually inspected. The plate assay is working with HRP as positive control. All positive controls showed green zones of converted ABTS, while none of the negative controls shows any visible conversion.

For the tested UPOs the plate assays did not show changes after one day. Therefore, the plates were stored for more than a week in the fridge. Surprisingly the color of the plate with the pH 4.5 buffer turned green at those plates, while the plate with the pH 6.0 buffer showed no changes. Color changes were expected for pH 4.5, because most UPOs are active at this pH value.

UPO12 Variants with Increased Peroxygenase Activity

In this Example, a UPO12 mutant library was screened for superior variants of UPO12 using ABTS, naphthalene and 2,6-DMP as substrates. Surprisingly, the largest group of improved variants were found to have a mutation at the C-terminus of the POX12 (UPO12) protein sequence (see FIG. 12).

Figure 9:
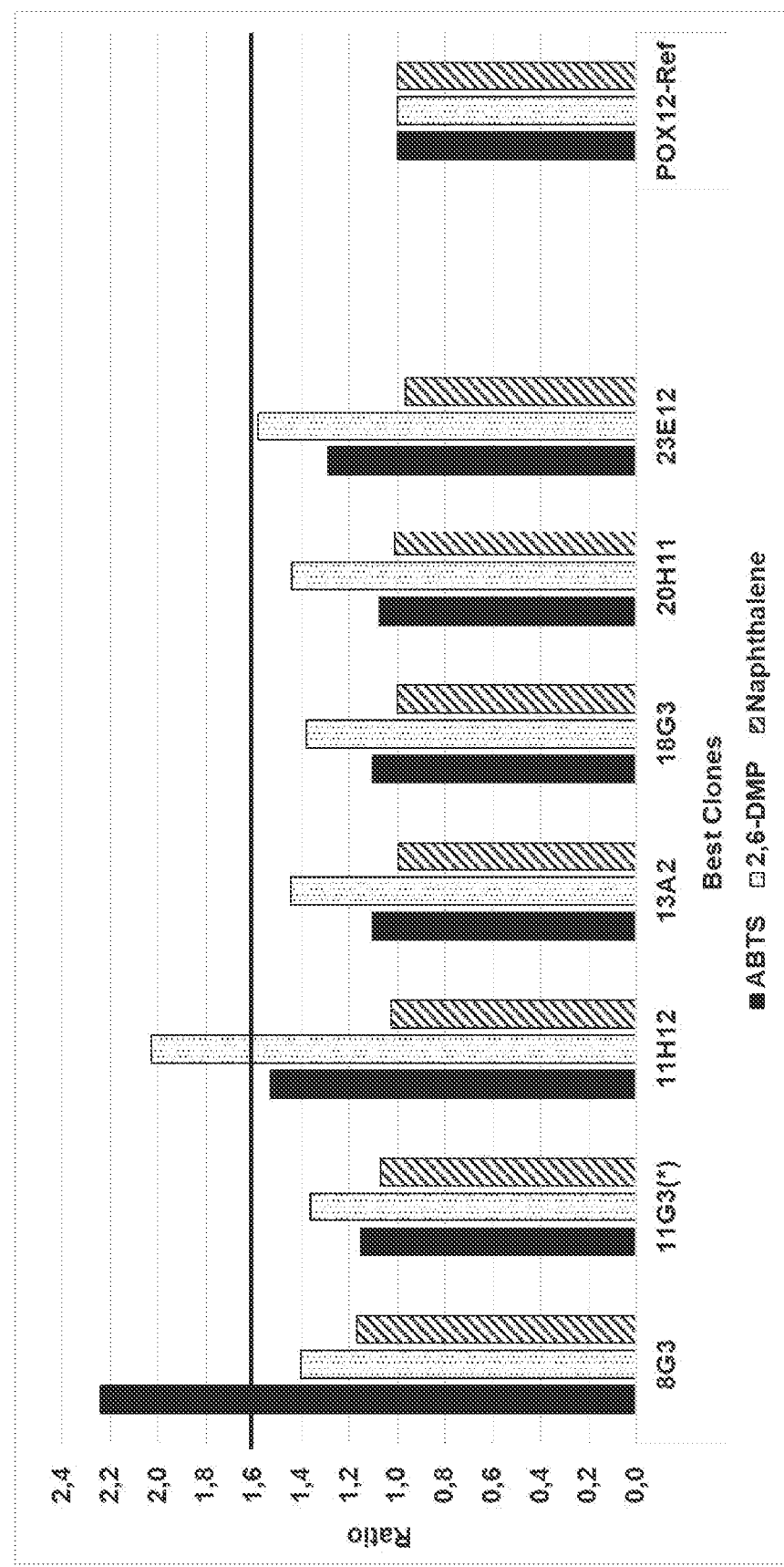
FIG. 9: Activity of selected UPO12 variants in relation to wild type UPO12 (clone 1G). Substrates: ABTS, 2,6-DMP, naphthalene; Cultivation: 96 hours in shake flask (48 hours growth/derepression, 48 hours MeOH induction).

Multiple variants of UPO12 (SEQ ID NO:12) were identified, also referred to herein as POX12, that showed improved activity on one or more of the tested substrates (ABTS, 2,6-DMP, naphthalene) or altered substrate profiles compared to UPO12 wild type (i.e. variants 23E12 (SEQ ID NO:30), 11G3 (SEQ ID NO:31), 8G3 (SEQ ID NO:32), 11H12 (SEQ ID NO:33), 13A2 (SEQ ID NO:34), 18G3 (SEQ ID NO:35) and 20H11 (SEQ ID NO:36)) (see FIG. 9).

As for UPO12, the corresponding genes of the 11 variants were cloned into the pBSY5S1Z integrative expression vector (containing a FMD promoter fragment of *Hansenula polymorpha*) via BioXP™ after codon optimization and replacement of their native secretion signals by the alpha factor secretion signal variant (MataD, a deletion variant of the *S. cerevisiae* mating factor aslpha signal sequence). The expression vector was introduced in *P. pastoris* for secretion of the variants.

Best results were obtained for variants 8G3 and 11H12. Variant 8G3 (C256S) had an amino acid exchange from cysteine (C) to serine (S) at position 256 which is just 5 amino acids prior the end of the protein. This exchange resulted in a doubling of peroxidase activity, i.e., twice as high activity on ABTS. Variant 8G3 also showed a 1.4-fold improvement on 2,6-DMP and 1.2-fold improvement on naphthalene. Also clone 11H12 showed twice as high activity on 2,6-DMP and a 1.5-fold higher activity on ABTS compared to the UPO12 reference clone. In agreement with the results from clone 8G3 and very surprising, also clone 11H12, showed a mutation at the very same position (C256X); however, a stop codon instead of cysteine.

Similarly, variants 20H11 (E249X), 13A2 (D253N), 18G3 (D253I), showed a C-terminal modification associated with higher activity, and showed an increase of at least 1.4-fold on 2,6-DMP.

Interestingly, variant 23E12 (524F) also had an amino acid exchange from polar serine to large hydrophobic phenylalanine just two amino acids further resulting in 1.3-fold and 1.6-fold higher activity on ABTS and 2,6-DMP, respectively.

Activities of UPO12 variants and their corresponding amino acid mutations compared to wild type UPO12 are summarized in FIG. 9 and Table 15.

TABLE 15

UPO12 variants amino acid sequence mutations. The variants are listed in groups related to the position of the mutation (N-terminal, middle, C-terminal or signal sequence), some clones were identified as WT for others sequencing was unambiguous ("n.s.r." = no sequencing results). (*) This clone did not show activity on any of the three substrates (ABTS, 2,6-DMP, naphthalene) in shake flask.

Mutation grouping

| N-terminal | Middle/C-terminal | C-terminal |
|---|---|---|
| 23E12 (S24F) | 11G3(D145YY)(*) | 8G3 (C256S) |
| | | 11H12 (C256X) |
| | | 13A2 (D253N) |
| | | 18G3 (D253I) |
| | | 20H11 (E249X) |

Identification of New Highly Active Peroxygenase Biocatalysts

In this Example, novel peroxygenases were identified by BLAST search using the UPO12 protein sequence (SEQ ID NO:12) as reference. Identified candidates were expressed in *P. pastoris* and screened for activity on ABTS, naphthalene and 2,6-DMP.

Using the UPO12 wild type amino acid sequence (SEQ ID NO:12) and the online BLAST tool from NCBI, 17 homologous enzymes containing the PCP-motif were identified. As for UPO12 the corresponding genes were cloned into the pBSY5S1Z integrative expression vector (containing an FMD promoter fragment of *Hansenula polymorpha*) via BioXP™ after codon optimization and replacement of their native secretion signals by the alpha factor secretion signal variant (MataD, a deletion variant of the *S. cerevisiae* mating factor alpha signal sequence).

Figure 11:
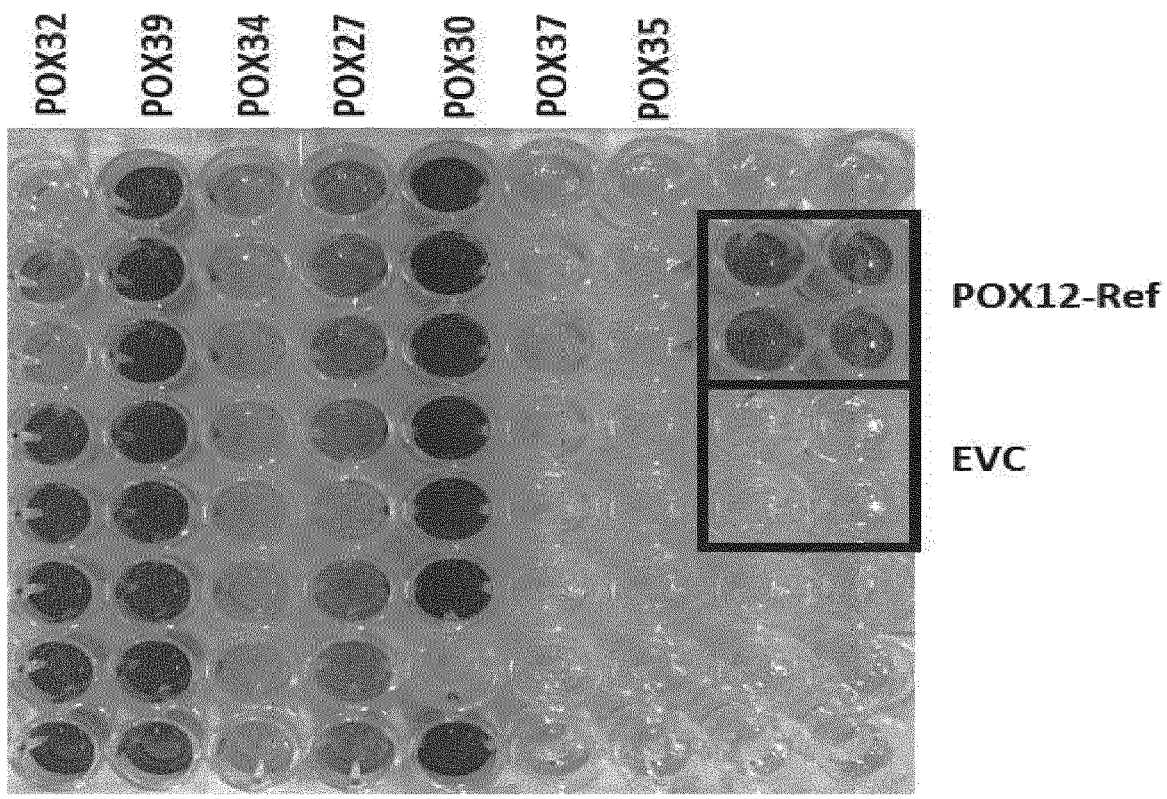
FIG. 11: ABTS-Assay (2.0 mM $H_2O_2$) results novel POXs (POX27, POX32, POX34, POX39). Eight clones of each variant studied using an 8-fold H2O2 access.

After *P. pastoris* transformation, screening of transformants identified four new UPOs with high activity on ABTS (POX27 (SEQ ID NO:37), POX32 (SEQ ID NO:39), POX34 (SEQ ID NO:40), POX39 (SEQ ID NO:41), see FIG. 11), three of them were also found active on 2,6-DMP and naphthalene (POX27, POX32, POX39). These UPOs were also studied in a reaction with ABTS using 2 mM $H_2O_2$ (8-fold concentration).

Figure 10:
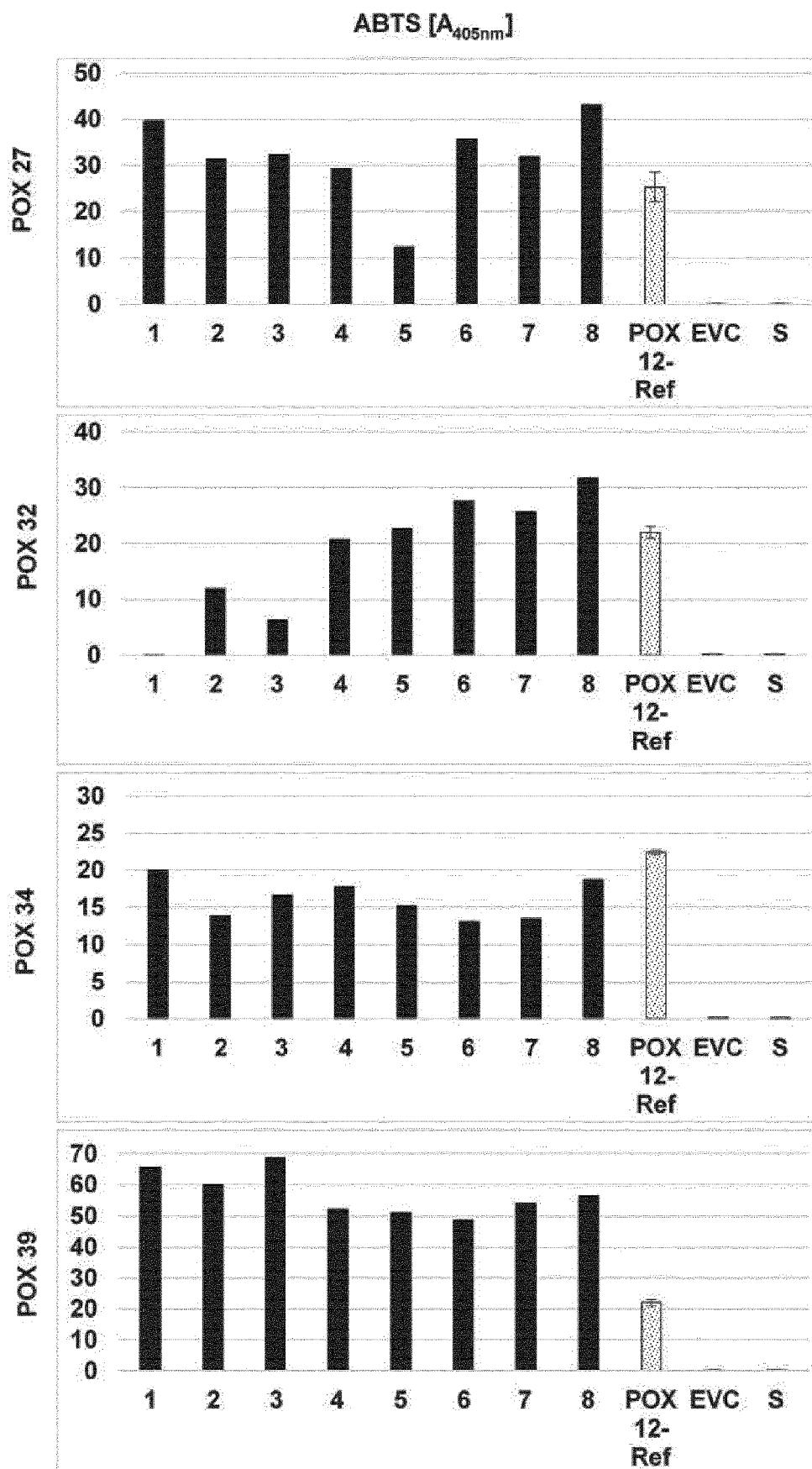
FIG. 10: Novel POXs (POX27, POX32, POX34, POX39). Screening results of 8 clones per enzyme. Substrates: ABTS, 2,6-DMP, naphthalene; Cultivation: 96 hours DWP cultivation (48 hours growth/de-repression, 48 hours MeOH induction).
Figure 10:
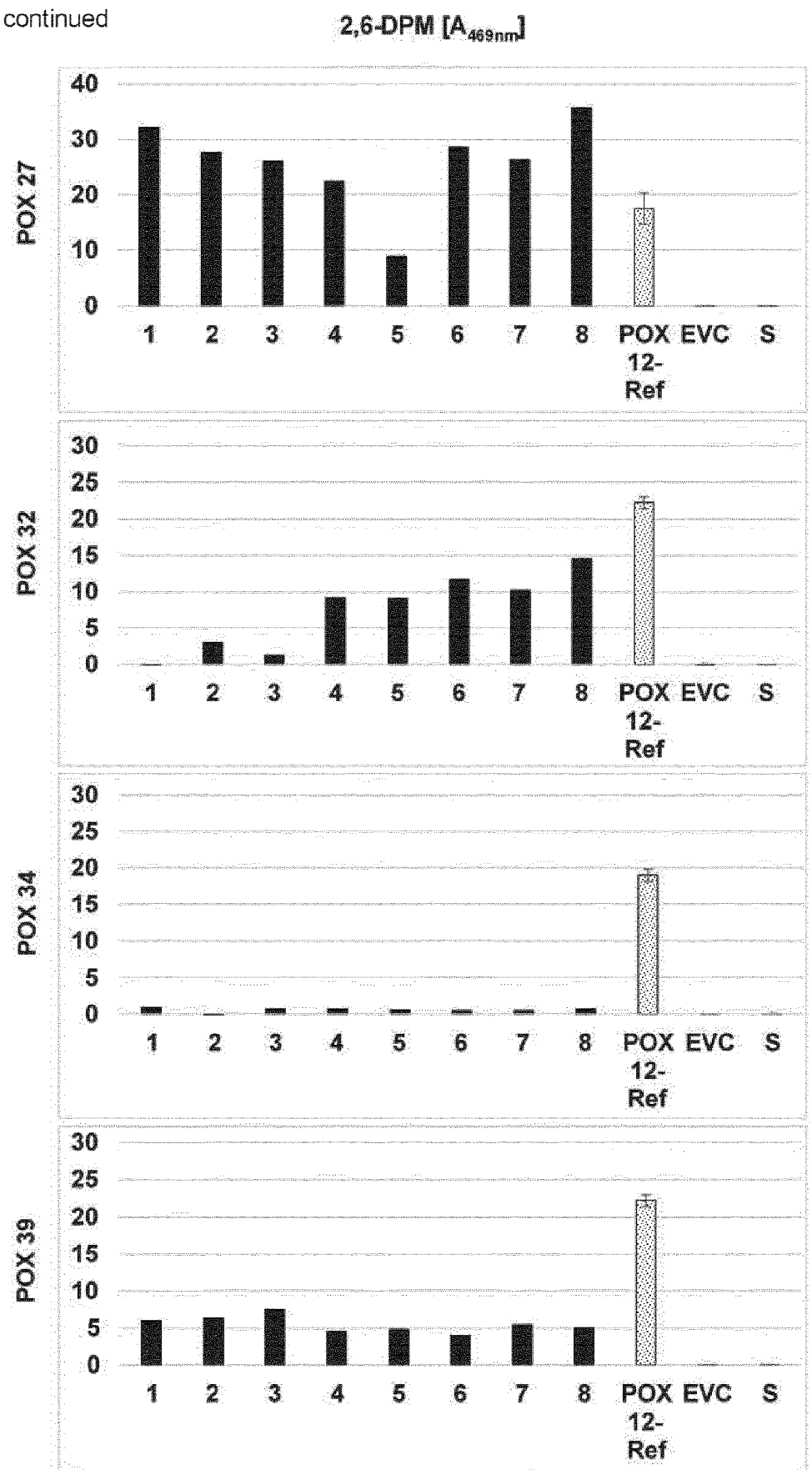
Figure 10:
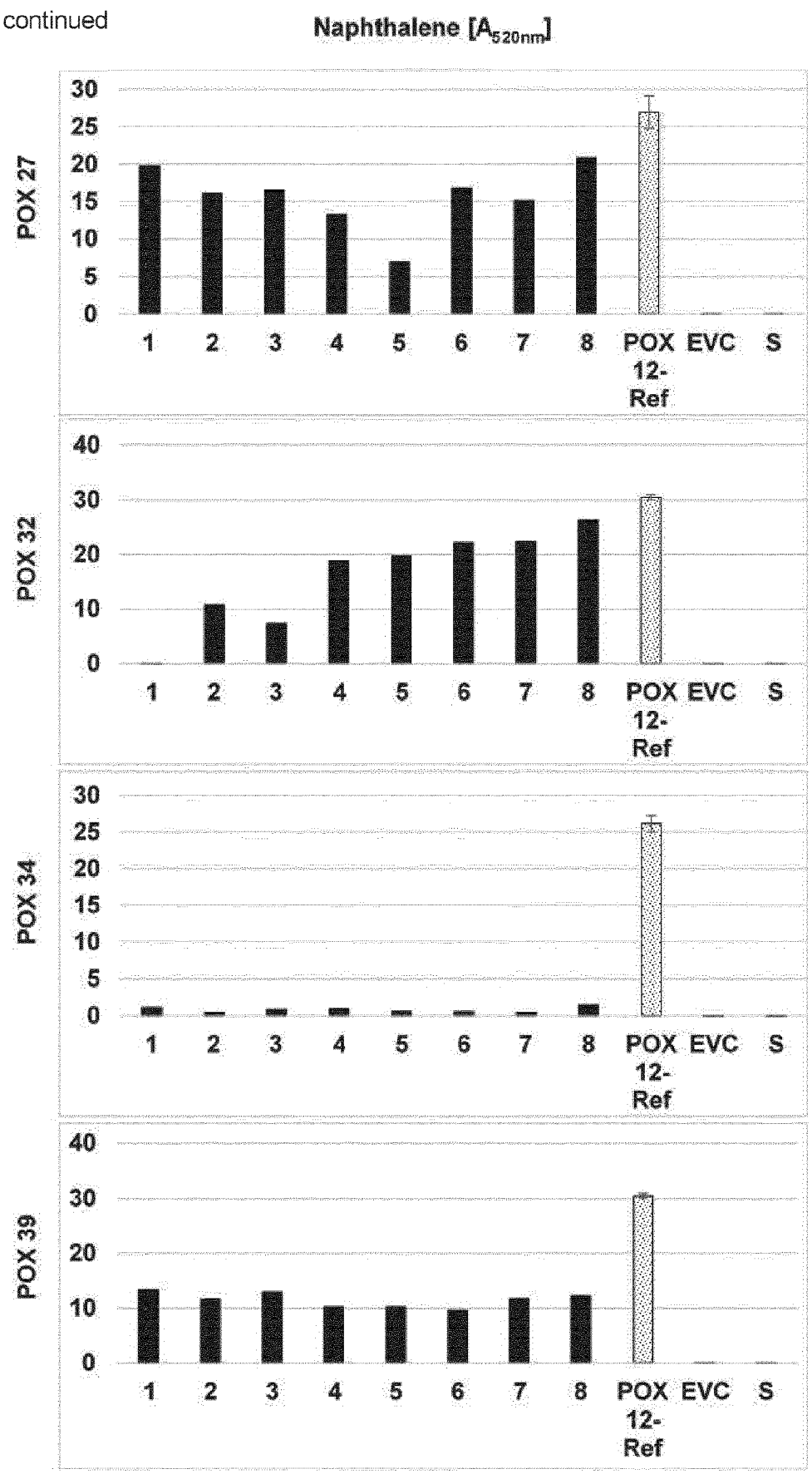

Surprisingly, another highly active UPO showing significantly higher activity on ABTS than the reference was identified (POX30 (SEQ ID NO:38), see FIG. 11). Novel peroxygenases showing significant activity on one or more of the tested substrates are summarized in FIG. 10 and FIG. 11.

REFERENCES

Babot, Esteban D. et al. 2013. "Oxyfunctionalization of Aliphatic Compounds by a Recombinant Peroxygenase from Coprinopsis Cinerea." Biotechnology and Bioengineering 110(9): 2323-32

Bormann, S. et al. "Specific oxyfunctionalisations catalysed by peroxygenases: opportunities, challenges and solutions." Catal. Sci. Technol. volume 5, issue 4, P2038-2052 2015

Faiza et al., BMC "New insights on unspecific peroxygenases: superfamily reclassification and evolution" Evol Biol. 2019 Mar. 13; 19(1):76.

Gröbe, Glenn et al. 2011. "High-Yield Production of Aromatic Peroxygenase by the Agaric Fungus Marasmius rotula." AMB Express 1(1): 1-11.

Kiebist et al. "A Peroxygenase from Chaetomium globosum Catalyzes the Selective Oxygenation of Testosterone." Chembiochem. 2017 Mar. 16; 18(6):563-569

Molina-Espeja et al., "Directed evolution of unspecific peroxygenase from Agrocybe aegerita" Appl Environ Microbiol. 2014 June; 80(11):127-143.

Molina-Espeja, Patricia et al. 2015. "Tandem-Yeast Expression System for Engineering and Producing Unspecific Peroxygenase." Enzyme Microb Technol. 2015 June; 73-74:29-33.

Morawski, Birgit et al. 2000. "Functional Expression of Horseradish Peroxidase in Saccharomyces cerevisiae and Pichia pastoris." Protein Engineering, Design and Selection 13(5): 377-84. https://academic.oup.com/peds/article-lookup/doi/10.1093/protein/13.5.377.

Pecyna, Marek J. et al. 2009. "Molecular Characterization of Aromatic Peroxygenase from Agrocybe aegerita." Applied Microbiology and Biotechnology 84(5): 885-97.

Pütter, J., & Becker, R. (1983). Peroxidase. In H. U. Bergmeyer, J. Bergmeyer, & M. Grassl (Ed.), Methods of enzymatic analysis (pp. 286-293). Weinheim: Verlag Chemie.

Yuan, Z. Y., & Jiang, T. J. (2002). Horseradish peroxidase. In J. R. Whitaker, A. G. J. Voragen, & D. W. S. Wong (Ed.), Handbook of food enzymology (pp. 403-411). New York: CRC Press.

Zámocký, Marcel et al., "Independent Evolution of Four Heme Peroxidase Superfamilies." Arch Biochem Biophys. 2015 May 15; 574:108-19.

---

The invention claimed is:

1. A modified unspecific peroxygenase (UPO) comprising an amino acid sequence having at least 75% sequence identity to the polypeptide of SEQ ID NO: 12 and having increased peroxygenase activity as compared to unmodified wild-type UPO12, which is the polypeptide of SEQ ID NO:12, wherein the modification is a modification of at least one amino acid selected from D145, E249, D253, and/or C256 of the polypeptide of SEQ ID NO:12, and wherein the peroxygenase activity is increased by 1.3-fold or more when measured in an ABTS assay or a 2,6-DMP assay.

2. The modified UPO of claim 1, comprising at least a mutation corresponding to D145Y, D253N, D253I, C256S, and/or introduction of a stop codon at a position corresponding to C256 or E249 of SEQ ID NO:12.

3. The modified UPO of claim 1, wherein the peroxygenase activity is 1.5-fold, 2.0-fold, or more increased when measured in an ABTS assay or a 2,6-DMP assay.

4. The modified UPO of claim 1, comprising SEQ ID NO: 31, SEQ ID NO:32, SEQ ID NO:33, SEQ ID NO:34, SEQ ID NO:35, or SEQ ID NO: 36, or an amino acid sequence having at least 80%, 85%, 90%, 95%, 97%, 98%, or 99% identity to SEQ ID NO:31, SEQ ID NO:32, SEQ ID NO:33, SEQ ID NO:34, SEQ ID NO: 35, or SEQ ID NO:36.

5. A modified unspecific peroxygenase (UPO) having increased peroxygenase activity as compared to the unmodified wild-type UPO12 of SEQ ID NO: 12, wherein the modified UPO comprises SEQ ID NO:30, or an amino acid sequence having at least 90% sequence identity to SEQ ID NO:30 and comprising an amino acid modification of the amino acid corresponding to S24 of SEQ ID NO:12.

6. A method of performing a chemical reaction on a substrate, comprising reacting the substrate with the modified UPO of claim 1.

7. The method of claim 6, wherein the chemical reaction is an organic synthesis process, a polymerization process, a pharmaceutical production process, an environmental application, an application in consumer products, or a surface modification.

* * * * *

SEQUENCE LISTING

```
<160> NUMBER OF SEQ ID NOS: 41

<210> SEQ ID NO 1
<211> LENGTH: 371
<212> TYPE: PRT
<213> ORGANISM: Artificial Sequence
<220> FEATURE:
<223> OTHER INFORMATION: UPO1 mut

<400> SEQUENCE: 1

Met Lys Tyr Phe Pro Leu Phe Pro Thr Leu Val Tyr Ala Val Gly Val
1               5                   10                  15

Val Ala Phe Pro Asp Tyr Ala Ser Leu Ala Gly Leu Ser Gln Gln Glu
            20                  25                  30

Leu Asp Ala Ile Ile Pro Thr Leu Glu Ala Arg Glu Pro Gly Leu Pro
        35                  40                  45

Pro Gly Pro Leu Glu Asn Ser Ser Ala Lys Leu Val Asn Asp Glu Ala
    50                  55                  60

His Pro Trp Lys Pro Leu Arg Pro Gly Asp Ile Arg Gly Pro Cys Pro
65                  70                  75                  80

Gly Leu Asn Thr Leu Ala Ser His Gly Tyr Leu Pro Arg Asn Gly Val
                85                  90                  95

Ala Thr Pro Ala Gln Ile Ile Asn Ala Val Gln Glu Gly Phe Asn Phe
            100                 105                 110

Asp Asn Gln Ala Ala Ile Phe Ala Thr Tyr Ala Ala His Leu Val Asp
        115                 120                 125

Gly Asn Leu Ile Thr Asp Leu Leu Ser Ile Gly Arg Lys Thr Arg Leu
    130                 135                 140

Thr Gly Pro Asp Pro Pro Pro Ala Ser Val Gly Gly Leu Asn Glu
145                 150                 155                 160
```

His Gly Thr Phe Glu Gly Asp Ala Ser Met Thr Arg Gly Asp Ala Phe
            165                 170                 175

Phe Gly Asn Asn His Asp Phe Asn Glu Thr Leu Phe Glu Gln Leu Val
        180                 185                 190

Asp Tyr Ser Asn Arg Phe Gly Gly Lys Tyr Asn Leu Thr Val Ala
        195                 200                 205

Gly Glu Leu Arg Phe Lys Arg Ile Gln Asp Ser Ile Ala Thr Asn Pro
    210                 215                 220

Asn Phe Ser Phe Val Asp Phe Arg Phe Phe Thr Ala Tyr Gly Glu Thr
225                 230                 235                 240

Thr Phe Pro Ala Asn Leu Phe Val Asp Gly Arg Arg Asp Asp Gly Gln
            245                 250                 255

Leu Asp Met Asp Ala Ala Arg Ser Phe Phe Gln Phe Ser Arg Met Pro
            260                 265                 270

Asp Asp Phe Phe Arg Ala Pro Ser Pro Arg Ser Gly Thr Gly Val Glu
        275                 280                 285

Val Val Val Gln Ala His Pro Met Gln Pro Gly Arg Asn Val Gly Lys
        290                 295                 300

Ile Asn Ser Tyr Thr Val Asp Pro Thr Ser Ser Asp Phe Ser Thr Pro
305                 310                 315                 320

Cys Leu Met Tyr Glu Lys Phe Val Asn Ile Thr Val Lys Ser Leu Tyr
                325                 330                 335

Pro Asn Pro Thr Val Gln Leu Arg Lys Ala Leu Asn Thr Asn Leu Asp
            340                 345                 350

Phe Leu Phe Gln Gly Val Ala Ala Gly Cys Thr Gln Val Phe Pro Tyr
        355                 360                 365

Gly Arg Asp
    370

<210> SEQ ID NO 2
<211> LENGTH: 373
<212> TYPE: PRT
<213> ORGANISM: Artificial Sequence
<220> FEATURE:
<223> OTHER INFORMATION: UPO 2

<400> SEQUENCE: 2

Met Arg Gly Ala Ala Arg Phe Ala Val Leu Ile Ala Leu Phe Thr His
1               5                   10                  15

Ala Ala Ile Ala Phe Pro Ala Tyr Gly Ser Leu Ala Gly Leu Thr Arg
            20                  25                  30

Glu Gln Leu Asp Glu Ile Leu Pro Thr Leu Glu Ile Arg Glu Pro Gly
        35                  40                  45

Lys Pro Pro Gly Pro Leu Lys Asp Thr Ser Ala Lys Leu Val Asn Asp
    50                  55                  60

Lys Ala His Pro Trp Lys Pro Val Ala Pro Asp Ile Arg Gly Pro
65                  70                  75                  80

Cys Pro Gly Leu Asn Thr Leu Ala Ser His Gly Trp Leu Pro Arg Asn
                85                  90                  95

Gly Ile Ala Ser Pro Ser Glu Ile Ile Thr Ala Val Gln Glu Gly Phe
            100                 105                 110

Asn Met Asp Asn Gly Leu Ala Ile Phe Val Thr Tyr Ala Ala His Leu
        115                 120                 125

Val Asp Gly Asn Ile Leu Thr Asp Lys Leu Ser Ile Gly Gly Lys Thr
    130                 135                 140

```
Gly Leu Thr Gly Pro Asn Pro Pro Ala Pro Ala Ile Val Gly Gly Leu
145                 150                 155                 160

Asn Thr His Ala Val Phe Glu Gly Asp Thr Ser Met Thr Arg Gly Asp
            165                 170                 175

Phe Phe Phe Gly Asn Asn His Asp Phe Asn Glu Thr Leu Phe Asp Glu
        180                 185                 190

Phe Val Asp Phe Ser Asn Arg Phe Gly Ala Gly Lys Tyr Asn Leu Thr
    195                 200                 205

Val Ala Gly Glu Phe Arg Trp Gln Arg Ile Gln Asp Ser Ile Ala Thr
210                 215                 220

Asn Pro Glu Phe Ser Phe Val Ser Pro Arg Phe Phe Thr Ala Tyr Ala
225                 230                 235                 240

Glu Ser Thr Phe Pro Ile Asn Phe Phe Ile Asp Gly Arg Gln Thr Asp
                245                 250                 255

Gly Gln Leu Asp Leu Thr Val Ala Arg Gly Phe Phe Gln Asn Ser Arg
            260                 265                 270

Met Pro Asp Asp Phe His Arg Ala Asn Gly Thr Arg Gly Thr Glu Gly
        275                 280                 285

Ile Asp Leu Val Ala Glu Ala His Pro Ile Glu Pro Gly Ser Asn Val
    290                 295                 300

Gly Gly Val Asn Asn Tyr Val Val Asp Pro Thr Ser Ala Asp Phe Ser
305                 310                 315                 320

Thr Phe Cys Leu Leu Tyr Glu Asn Phe Asn Lys Thr Val Lys Gly
                325                 330                 335

Leu Tyr Pro Asn Pro Thr Gly Ala Leu Arg Lys Ala Leu Asn Thr Asn
                340                 345                 350

Leu Gly Phe Phe Phe Ser Gly Ile Ser Asp Ser Gly Cys Thr Gln Val
            355                 360                 365

Phe Pro Tyr Gly Lys
            370

<210> SEQ ID NO 3
<211> LENGTH: 377
<212> TYPE: PRT
<213> ORGANISM: Artificial Sequence
<220> FEATURE:
<223> OTHER INFORMATION: UPO 3

<400> SEQUENCE: 3

Met Leu Lys Leu Phe Phe Val Gln Thr Ala Leu Leu Ala Leu Ser Gly
1               5                   10                  15

Thr Thr Phe Ala Tyr Pro Ser His Met Ser Leu Ala Gly Leu Thr Arg
            20                  25                  30

Glu Gln Leu Asp Gln Ile Val Pro Thr Leu Thr Phe Thr Pro Pro
        35                  40                  45

Pro Pro Pro Ala Pro Leu Asn Asp Thr Ser Ala Lys Leu Val Asn Asp
    50                  55                  60

Pro Ala His Pro Trp Gln Pro Leu Arg Ala Gly Asp Ile Arg Gly Val
65                  70                  75                  80

Cys Pro Gly Leu Asn Thr Leu Ala Ser His Gly Tyr Leu Pro Arg Asn
                85                  90                  95

Gly Ile Val Thr Pro Asn Gln Ile Ile Glu Ala Ala Gln Asp Gly Phe
            100                 105                 110

Asn Met Asp Asn Thr Leu Ala Arg Phe Leu Ala Tyr Gly Thr Phe Leu
        115                 120                 125
```

Val Asp Gly Asn Val Val Thr Asn Glu Met Ser Ile Gly Ser Lys Ser
130                 135                 140

Ala Ala Thr Gly Pro Asp Pro Ala Pro Ala Ile Val Gly Gly Leu
145                 150                 155                 160

Asp Thr His Ala Val Phe Glu Gly Asp Ala Ser Met Thr Arg Gln Asp
                165                 170                 175

Phe Phe Phe Gly Asn Asn His Asp Phe Asn Glu Thr Leu Phe Asp Gln
            180                 185                 190

Phe Val Glu Phe Ser Asn Arg Phe Gly Ala Gly Lys Tyr Asn Leu Thr
        195                 200                 205

Val Ala Gly Glu Leu Arg His Gln Arg Ile Gln Gln Ser Ile Ala Thr
210                 215                 220

Asn Pro Asn Phe Thr Phe Val Ala Pro Arg Tyr Phe Thr Ala Phe Ala
225                 230                 235                 240

Glu Ser Ala Phe Pro Val Asp Phe Phe Ile Asp Gly Arg Asp Ser Asn
                245                 250                 255

Gly Gln Leu Glu Met Asp Val Ala Arg Ser Phe Phe Gln Asn Ser Arg
            260                 265                 270

Phe Pro Asp Gly Phe Phe Arg Pro Asn His Ser Val Thr Gly Glu Gly
        275                 280                 285

Ser Asp Val Val Phe Ala Ala His Pro Ile Glu Pro Gly Arg Asn Val
290                 295                 300

Gly Gly Val Asn Asn Tyr Val Leu Asp Pro Thr Ser Ala Asp Phe Thr
305                 310                 315                 320

Thr Pro Cys Leu Leu Tyr Thr Asn Phe Val Asn Glu Thr Ile Val Gly
                325                 330                 335

Leu Tyr Pro Ser Pro Thr Gly Asp Leu Arg Thr Ala Leu Asn Phe Tyr
            340                 345                 350

Leu Asn Leu Phe Phe Glu Ala Phe Asp Asn Ser Glu Gly Ser Gly Cys
        355                 360                 365

Thr Gln Leu Phe Pro Tyr Gly Gln Asp
        370                 375

<210> SEQ ID NO 4
<211> LENGTH: 375
<212> TYPE: PRT
<213> ORGANISM: Artificial Sequence
<220> FEATURE:
<223> OTHER INFORMATION: UPO 4

<400> SEQUENCE: 4

Met Phe Ser Leu Leu Asn Phe Val Thr Leu Ala Leu Ala Cys Thr Trp
1               5                   10                  15

Ser Ala Leu Ala Phe Pro Ser Ser Tyr Thr Ser Leu Gly Gly Leu Pro
            20                  25                  30

Arg Glu Glu Leu Asp Arg Ile Leu Pro Ser Leu Gln Tyr Arg Ser Pro
        35                  40                  45

Gly Ala Pro Pro Gly Pro Leu Lys Phe Asn Gly Thr Lys Leu Val Asn
    50                  55                  60

Asp Asp Gln His Pro Trp Lys Pro Leu Lys His Gly Asp Met Arg Gly
65                  70                  75                  80

Pro Cys Pro Gly Leu Asn Thr Leu Ala Ser His Gly Tyr Leu Pro Arg
                85                  90                  95

Asn Gly Ile Ala Thr Pro Val Gln Ile Ile Asn Ala Val Gln Glu Gly
            100                 105                 110

Phe Asn Met Glu Asn Ser Val Ala Arg Leu Val Thr Tyr Ala Ala His
            115                 120                 125

Leu Val Asp Gly Asn Leu Val Thr Asp Lys Leu Ser Ile Gly Gly Lys
        130                 135                 140

Ser Pro Leu Thr Gly Pro Ser Pro Ala Pro Ala Asn Ala Ala Gly
145                 150                 155                 160

Leu Asn Thr His Ala Leu Phe Glu Gly Asp Val Ser Met Thr Arg Ala
            165                 170                 175

Asp Ala Phe Phe Gly Asp Asn His Ser Phe Asn Glu Thr Leu Phe Asp
                180                 185                 190

Glu Phe Thr Ala Phe Ser Asn Gln Phe Gly Ala Gly Lys Tyr Asn Leu
            195                 200                 205

Thr Val Ala Ala Glu Tyr Arg Phe His Arg Ile Gln Glu Ser Ile Ala
        210                 215                 220

Thr Asn Pro Asn Phe Ser Phe Val Ser Pro Arg Phe Phe Thr Ala Tyr
225                 230                 235                 240

Ala Glu Ser Val Phe Pro Ile Asn Phe Ile Asp Gly Arg Gln Gly
            245                 250                 255

Asp Gly Gln Leu Asp Leu Asp Val Ala Arg Gly Phe Phe Gln Asn Met
                260                 265                 270

Arg Met Pro Asp Gly Phe His Arg Ala Ser Ile Pro Thr Gly Leu Glu
            275                 280                 285

Gly Leu Ala Glu Ile Ala Ser Val His Pro Ile Ser Pro Gly Ala Asn
        290                 295                 300

Val Asn Gly Val Asn Thr Tyr Thr Phe Asp Pro Ser Ser Ala Asp Phe
305                 310                 315                 320

Thr Thr Phe Cys Leu Leu Tyr Val Asn Phe Val Asn Gln Thr Val Arg
            325                 330                 335

Ser Leu Tyr Pro Glu Pro Thr Gly Asn Leu Lys Lys Ala Leu Lys Lys
            340                 345                 350

Asn Leu Glu Phe Leu Tyr Gly Pro Phe Ser Asp Gln Cys Ser Gln Val
        355                 360                 365

Phe Pro Tyr Gly Lys Asp Asn
    370                 375

<210> SEQ ID NO 5
<211> LENGTH: 376
<212> TYPE: PRT
<213> ORGANISM: Artificial Sequence
<220> FEATURE:
<223> OTHER INFORMATION: UPO 5

<400> SEQUENCE: 5

Met Ala Arg Leu Thr Phe Leu Val Ala Val Ala Leu Ala Leu Ser Ser
1               5                   10                  15

Thr Thr Val Ala Phe Pro Ser Tyr Gly Ser Leu Ala Gly Leu Ser Glu
            20                  25                  30

Ala Glu Leu Asp Arg Ile Ile Pro Leu Leu Glu Ala Arg Asp Ala Cys
        35                  40                  45

Pro Pro Pro Gly Pro Leu Lys Asn Thr Ser Thr Lys Leu Val Asn Asp
50                  55                  60

Lys Asp His Pro Trp Lys Pro Leu Arg Asp Gly Asp Ile Arg Gly Pro
65                  70                  75                  80

Cys Pro Gly Leu Asn Thr Leu Ala Ser His Gly Trp Leu Pro Arg Asn
            85                  90                  95

-continued

Gly Val Ala Thr Pro Ala Gln Ile Ile Asn Ala Val Gln Glu Gly Phe
                100                 105                 110

Asn Met Gly Asn Asp Leu Ala Val Phe Val Thr Tyr Ala Ala His Leu
            115                 120                 125

Val Asp Gly Asn Gln Val Thr Asp Leu Leu Ser Ile Gly Gly Lys Thr
        130                 135                 140

Pro Gln Thr Gly Pro Asp Pro Gln Pro Ala Ile Val Gly Gly Leu
145                 150                 155                 160

Asp Thr His Ala Val Phe Glu Gly Asp Ala Ser Met Thr Arg Gly Asp
                165                 170                 175

Ala Phe Phe Gly Asp Asn His Ser Phe Asn Glu Thr Gln Phe Asp Glu
            180                 185                 190

Phe Ser Ala Phe Ser Asn Lys Phe Gly Gly Tyr Tyr Asn Leu Ser
        195                 200                 205

Val Ala Ala Glu Phe Arg Trp Gln Arg Ile Gln Glu Ser Ile Ala Thr
    210                 215                 220

Asn Pro Asn Phe Ser Phe Ile Ser Pro Arg Tyr Phe Thr Ala Tyr Ala
225                 230                 235                 240

Glu Ser Val Phe Pro Leu Val Phe Phe Val Asp Gly Arg Val Ser Asp
                245                 250                 255

Gly Arg Leu Ser Leu Pro Asn Ala Arg Gly Phe Phe Gln Asn Ser Gln
            260                 265                 270

Met Pro Thr Asp Phe Phe Arg Pro Asn Gln Ser Ile Gly Leu Asp Val
        275                 280                 285

Ile Gly Asp Gly Ile Ser Ala Ile Ala Ser Ala His Pro Ile Ala Pro
    290                 295                 300

Gly Lys Asn Glu Gly Val Gly Asn Tyr Val Leu Asp Pro Thr Ser Ala
305                 310                 315                 320

Asp Phe Asp His Phe Cys Leu Leu Tyr Ile Asn Phe Val Asn Gln Thr
                325                 330                 335

Val Lys Ser Leu Tyr Pro Asn Pro Thr Gly Val Leu Arg Asp Ala Leu
            340                 345                 350

Lys Arg Asn Leu Asp Asn Phe Tyr Ser Pro Leu Asn Gly Ser Asp Cys
        355                 360                 365

Val Gln Ile Phe Pro Tyr Gly Lys
    370                 375

<210> SEQ ID NO 6
<211> LENGTH: 376
<212> TYPE: PRT
<213> ORGANISM: Artificial Sequence
<220> FEATURE:
<223> OTHER INFORMATION: UPO 6

<400> SEQUENCE: 6

Met Val Gln Phe Thr Val Ile Leu Ser Leu Leu Leu Ala Thr Gly Lys
1               5                   10                  15

Ala Leu Ala Phe Pro Gln Tyr Gly Ser Leu Ala Gly Leu Ser Glu Arg
            20                  25                  30

Glu Leu Glu Asp Ile Leu Pro Arg Leu His Ala Val Lys Pro Pro Pro
        35                  40                  45

Pro Pro Gly Pro Leu Asn Asp Thr Ser Thr Lys Leu Val Asn Asn Pro
    50                  55                  60

Ala His Pro Phe Leu Pro Gln Arg Asn Gly Asp Met Arg Gly Pro Cys
65                  70                  75                  80

```
Pro Gly Leu Asn Thr Leu Ala Ser His Gly Tyr Leu Pro Arg Asn Gly
                85                  90                  95

Ile Ala Thr Pro Ala Gln Ile Ile Asn Ala Val Gln Glu Gly Phe Asn
            100                 105                 110

Met Gly Asn Asp Leu Ala Val Phe Val Thr Tyr Ala Ala Phe Leu Val
        115                 120                 125

Asp Gly Asn Gln Val Thr Asn Leu Leu Ser Ile Gly Gly Lys Ser Ser
    130                 135                 140

Leu Thr Gly Pro Asp Pro Lys Pro Ala Ile Val Gly Gly Leu Asp
145                 150                 155                 160

Thr His Ala Val Phe Glu Gly Asp Ala Ser Met Thr Arg Gly Asp Ala
                165                 170                 175

Phe Phe Gly Asp Asn His Ser Phe Lys Glu Asn Gln Phe Asp Glu Phe
            180                 185                 190

Ile Ala Phe Ser Asn Lys Phe Gly Gly Lys Tyr Asn Leu Thr Val
        195                 200                 205

Ala Ser Glu Phe Arg Trp Gln Arg Ile Gln Ser Thr Ala Thr Asn
    210                 215                 220

Pro Asn Phe Ser Phe Ile Ser Pro Arg Tyr Phe Thr Ala Tyr Ala Glu
225                 230                 235                 240

Ser Thr Phe Pro Ile Thr Phe Val Asp Gly Arg Asn Glu Asp Gly
                245                 250                 255

Ala Leu Ser Leu Asp Val Ala Arg Gly Phe Phe Gln Asp Ser Arg Met
            260                 265                 270

Pro Asn Gly Phe Phe Arg Ala Asn Gln Ser Ile Gly Leu Asp Ile Ile
        275                 280                 285

Gly Ser Leu Ile Asp Phe Ile Phe Glu Pro His Pro Ile Gln Pro Gly
    290                 295                 300

Gly Asn Gln Gly Arg Val Asn Ser Tyr Thr Val Asp Pro Asn Ser Ala
305                 310                 315                 320

Asn Phe Ser Gln Phe Cys Gln Leu Tyr Gln Asp Phe Val Asn Asn Thr
                325                 330                 335

Val Lys Gly Leu Tyr Pro Asn Pro Gln Gly Val Leu Arg Asp Asn Leu
            340                 345                 350

Asn Thr Asn Leu Gly Phe Phe Phe Ser Pro Leu Gln Gly Ser Gly Cys
        355                 360                 365

Pro Gln Val Phe Pro Phe Gly Gln
    370                 375

<210> SEQ ID NO 7
<211> LENGTH: 376
<212> TYPE: PRT
<213> ORGANISM: Artificial Sequence
<220> FEATURE:
<223> OTHER INFORMATION: UPO 7

<400> SEQUENCE: 7

Met Arg Phe Phe Ser His Leu Ser Ile Ile Pro Leu Leu Ser Leu His
1               5                   10                  15

Gly Val Leu Ala Phe Pro Ser Tyr Gly Thr Leu Ala Gly Leu Ser Arg
            20                  25                  30

Ser Glu Leu Glu Ala Ile Leu Pro Thr Leu Lys Pro Gly Val Pro Glu
        35                  40                  45

Ser Pro Pro Gly Pro Leu Asn Asp Thr Ser Ala Lys Leu Val Asn Asp
    50                  55                  60
```

```
Lys Lys His Pro Trp Lys Pro Ala Gly Lys Lys Asp Ile Arg Gly Pro
 65                  70                  75                  80

Cys Pro Gly Leu Asn Thr Leu Ala Ser His Gly Trp Leu Pro Arg Asp
             85                  90                  95

Gly Val Ala Thr Pro Ala Gln Ile Val Asn Ala Val Gln Glu Gly Phe
            100                 105                 110

Asn Met Gly Asn Asp Leu Ala Val Phe Val Thr Tyr Ala Ala His Leu
        115                 120                 125

Val Asp Gly Asn Leu Ile Thr Asn Leu Leu Ser Ile Gly Gly Lys Thr
    130                 135                 140

Asp Arg Thr Gly Pro Asn Pro Pro Pro Ala Ile Val Gly Gly Leu
145                 150                 155                 160

Asn Thr His Ala Val Phe Glu Gly Asp Ala Ser Thr Thr Arg Ala Asp
                165                 170                 175

Phe Phe Phe Gly Asp Asn His Ser Phe Asn Glu Thr Leu Phe Asp Glu
            180                 185                 190

Leu Thr Ala Phe Ser Asn Lys Phe Gly Gly Phe Tyr Asn Leu Ser
        195                 200                 205

Val Ala Ala Glu Phe Arg Phe Gln Arg Ile Gln Asp Ser Ile Ala Thr
    210                 215                 220

Asn Pro Gln Phe Asp Phe Ile Ser Pro Arg Tyr Phe Thr Ala Tyr Ala
225                 230                 235                 240

Glu Ser Ile Phe Pro Leu Thr Phe Phe Ile Asp Gly Arg Asp Lys Ser
                245                 250                 255

Leu His Leu Asp Met Asn Val Ala Arg Gly Phe Phe Gln Asn Ser Arg
            260                 265                 270

Phe Pro Asp Gly Phe Phe Arg Ser Asn Thr Ser Ile Thr Leu Asp Val
        275                 280                 285

Ile Gly Gly Gly Ile Asp Tyr Ile Phe Ser Lys His Pro Val Pro Pro
    290                 295                 300

Gly Ser Asn Asn Gly Thr Val Asn Ser Tyr Thr Pro Asn Pro Asn Ser
305                 310                 315                 320

Ala Asp Phe Thr Gln Phe Cys Lys Leu Tyr Thr Asp Phe Val Asn Ile
                325                 330                 335

Thr Ile Arg Gly Leu Tyr Pro Asn Ala Lys Gly Ala Leu Leu Thr Ala
            340                 345                 350

Leu Asn Lys Asn Leu Glu Tyr Phe Tyr Ser Pro Leu Val Gly Ser Gly
        355                 360                 365

Cys Pro Gln Val Pro Pro Phe Val
    370                 375

<210> SEQ ID NO 8
<211> LENGTH: 376
<212> TYPE: PRT
<213> ORGANISM: Artificial Sequence
<220> FEATURE:
<223> OTHER INFORMATION: UPO 8

<400> SEQUENCE: 8

Met Ala Arg Val Phe Phe Ala Ile Ala Ala Leu Leu Leu Ala Ala Lys
 1               5                  10                  15

Asp Val Val Ser Phe Pro Asn Tyr Ala Ser Leu Ala Gly Leu Ser Glu
                20                  25                  30

Arg Glu Leu Asp Glu Ile Ile Pro Gln Leu Thr Val Arg Thr Leu Glu
             35                  40                  45
```

```
Lys Pro Pro Gly Gln Met Lys Asn Thr Leu Thr Lys Leu Val Asn Asp
    50                  55                  60

Pro Ala His Pro Trp Ile Ala Pro Ala Pro Asp Asp Gln Arg Asp Pro
65                  70                  75                  80

Cys Pro Gly Leu Asn Thr Leu Ala Asn His Gly Tyr Leu Pro Arg Asp
                85                  90                  95

Gly Ile Ala Thr Pro Ala Gln Ile Val Asn Ala Val Gln Glu Gly Phe
            100                 105                 110

Asn Met Ala Asn Asp Ile Ala Val Phe Val Thr Tyr Ala Ala His Leu
            115                 120                 125

Val Asp Gly Asn Leu Leu Thr Asp Leu Leu Ser Ile Gly Gly Lys Ser
    130                 135                 140

Ala Lys Thr Gly Pro Asn Pro Pro Ser Pro Ala Ile Val Gly Gly Leu
145                 150                 155                 160

Asp Thr His Ala Val Phe Glu Gly Asp Ala Ser Thr Thr Arg Gly Asp
                165                 170                 175

Ala Phe Phe Gly Asp Asn His Ser Phe Asn Glu Ser Leu Phe Asp Glu
            180                 185                 190

Leu Thr Ala Phe Ser Asn Lys Phe Gly Ala Gly Phe Tyr Asn Leu Ser
    195                 200                 205

Val Ala Thr Glu Phe Arg Phe Gln Arg Ile Gln Asp Ser Ile Ala Thr
    210                 215                 220

Asn Pro Gln Phe Ser Leu Ile Ser Pro Arg Tyr Tyr Thr Ala Tyr Ala
225                 230                 235                 240

Glu Ser Val Phe Pro Val Ala Phe Phe Val Asp Gly Arg Glu Thr Asn
                245                 250                 255

Gly Ser Leu Asn Met Thr Val Ala Arg Gly Phe Phe Gln Asp Gly Arg
            260                 265                 270

Met Pro Asn Asp Phe Phe Arg Ser Asn Ile Ser Trp Gly Leu Asp Leu
            275                 280                 285

Ile Gly Glu Gly Ile Gly Phe Ile Phe Thr Pro His Pro Ile Glu Pro
    290                 295                 300

Gly Thr Asn Asn Gly Thr Leu Asn Ser Tyr Thr Leu Asp Pro Asn Ser
305                 310                 315                 320

Ala Asp Phe Ser Asp Phe Cys Lys Leu Tyr Thr Asp Phe Val Asn Val
                325                 330                 335

Thr Val Arg Gly Leu Tyr Pro Asn Ala Thr Gly Pro Leu Leu Asn Ala
            340                 345                 350

Leu Asn Gln Asn Leu Asp Phe Phe Gly Pro Leu Gly Asp Gln Gly
        355                 360                 365

Cys Thr Gln Val Pro Ala Phe Val
    370                 375

<210> SEQ ID NO 9
<211> LENGTH: 275
<212> TYPE: PRT
<213> ORGANISM: Artificial Sequence
<220> FEATURE:
<223> OTHER INFORMATION: UPO 9

<400> SEQUENCE: 9

Met Lys Leu Asn Ile Phe Ser Thr Thr Leu Ala Ile Gly Leu Val Ser
1               5                   10                  15

Ala Gly Ala His Tyr His Gln Gln Asp Val Val Ala Asn Gly Thr Glu
            20                  25                  30
```

Gly Val Trp Ile Ala Pro Thr Asp Thr Asp Tyr Arg Gly Pro Cys Pro
            35                  40                  45

Met Met Asn Thr Leu Ala Asn His Gly Phe Leu Pro Arg Asp Gly Lys
 50                  55                  60

Asn Leu Thr Glu Tyr Asn Val Val Lys Gly Leu Asn Asp Gly Leu Asn
 65                  70                  75                  80

Phe Asn Lys Ser Leu Ala Thr Ile Met Phe Gln Gln Ala Ile Pro Ala
                85                  90                  95

Ser Pro Ala Tyr Pro Asn Ala Thr Phe Phe Thr Leu Asn Asp Leu Asn
            100                 105                 110

Arg His Asn Val Leu Glu His Asp Gly Ser Ile Ser Arg Ser Asp Ala
            115                 120                 125

Tyr Tyr Gly Asn Asn Tyr Ile Phe Asn Gln Thr Ile Phe Asp Thr Thr
            130                 135                 140

Lys Ala Tyr Trp Pro Ser Glu Thr Leu Thr Ala Gln His Leu Ile Asp
145                 150                 155                 160

Gly Lys Met Phe Arg Gln Ile Val Ser Arg Ser Thr Asn Pro Asn Tyr
                165                 170                 175

Thr Phe Ser Ala Thr Gln Gln Phe Ser Leu Gly Glu Met Ala Ala
            180                 185                 190

Pro Ile Val Ala Phe Gly Asp Lys Tyr Val Val Thr Ala Asn Arg Thr
            195                 200                 205

Leu Val Glu Ser Trp Ile Glu Asn Glu Arg Leu Pro Thr Glu Leu Gly
            210                 215                 220

Trp Arg Lys Pro Val Glu Glu Ile Leu Leu Ser Asp Ile Thr Tyr Val
225                 230                 235                 240

Thr Glu Val Leu Gly Asn Leu Thr Ser Leu Tyr Ser Thr Val Ile Ile
                245                 250                 255

Thr Pro Asn Pro Asp Ser Leu Ala Lys Arg Gln Met Gly His Trp Gly
            260                 265                 270

Gln Ser Ile
        275

<210> SEQ ID NO 10
<211> LENGTH: 265
<212> TYPE: PRT
<213> ORGANISM: Artificial Sequence
<220> FEATURE:
<223> OTHER INFORMATION: UPO 10

<400> SEQUENCE: 10

Met Lys Thr Thr Thr Leu Leu Cys Leu Ala Ala Leu Thr Gln Thr
 1               5                  10                  15

Tyr Ala Phe Pro Gln Gln Gly Ala Pro His Pro Leu Trp Ser Pro
            20                  25                  30

Pro Gly Pro Asn Asp Val Arg Ala Pro Cys Pro Met Leu Asn Thr Leu
            35                  40                  45

Ala Asn His Gly Tyr Leu Pro His Asn Gly Lys Asp Ile Thr Glu Arg
            50                  55                  60

His Thr Ile Asn Ala Leu Tyr Asn Ala Leu Gly Ile Glu Glu Glu Leu
 65                  70                  75                  80

Ala Ile Tyr Leu His Gln Glu Ala Val Thr Thr Asn Pro Ala Pro Asn
                85                  90                  95

Ala Thr Thr Phe Ser Leu Asn Asp Leu Ser Arg His Asp Ile Leu Glu
            100                 105                 110

```
His Asp Ala Ser Leu Ser Arg Gln Asp Ala Tyr Phe Gly Asp Asn His
            115                 120                 125

Asp Phe Asn Gln Thr Ile Phe Asp Glu Thr Arg Ser Tyr Trp Thr Ser
130                 135                 140

Pro Ile Ile Asp Val Lys Gln Ala Ala Val Ser Arg Gln Ala Arg Val
145                 150                 155                 160

Asn Thr Ser Met Ala Thr Asn Pro Asn Tyr Thr Met Ser Glu Leu Gly
            165                 170                 175

Asp Ser Phe Ser Tyr Gly Glu Thr Ala Ala Tyr Ile Ile Val Leu Gly
            180                 185                 190

Asp Lys Glu Lys Gly Leu Val Asn Arg Ser Arg Val Glu Tyr Leu Phe
            195                 200                 205

Glu Asn Glu Arg Leu Pro Leu Asp Leu Gly Trp Ser Arg Ala Lys Glu
            210                 215                 220

Asn Ile Thr Phe Asp Asp Leu Ser Thr Met Leu Gln Arg Ile Ile Asn
225                 230                 235                 240

Ala Thr Gly Gly Glu Met Asp Phe Arg Ala Thr Ile Ala Leu Pro Arg
            245                 250                 255

Leu Val Tyr Ile Tyr Tyr Glu Glu Ala
            260                 265

<210> SEQ ID NO 11
<211> LENGTH: 263
<212> TYPE: PRT
<213> ORGANISM: Artificial Sequence
<220> FEATURE:
<223> OTHER INFORMATION: UPO 11

<400> SEQUENCE: 11

Met Lys Thr Thr Thr Leu Leu Phe Leu Val Gly Ala Leu Thr Gln Thr
1               5                   10                  15

His Ala Phe Pro Gln Gln Gly Val Pro His Pro Leu Pro Trp Ser Pro
            20                  25                  30

Pro Gly Pro Asn Asp Val Arg Ala Pro Cys Pro Met Leu Asn Thr Leu
            35                  40                  45

Ala Asn His Gly Phe Leu Pro His Asn Gly Lys Asn Ile Thr Gln Gln
        50                  55                  60

His Thr Ile Asn Ala Leu Tyr Asn Ala Leu Gly Ile Asp Ala Glu Leu
65                  70                  75                  80

Ala Thr Tyr Leu His Gln Glu Ala Val Thr Thr Asn Pro Val Pro Asn
            85                  90                  95

Ala Thr Thr Phe Ser Leu Asn Asp Leu Ser Arg His Asp Ile Leu Glu
            100                 105                 110

His Asp Ala Ser Leu Ser Arg Gln Asp Ala Phe Phe Gly Asp Asn His
            115                 120                 125

Asp Phe Asn Gln Thr Ile Phe Asn Gln Thr Arg Ser Tyr Trp Thr Ser
130                 135                 140

Pro Ile Ile Asp Val Lys Gln Ala Leu Ala Arg Gln Ala Arg Val
145                 150                 155                 160

Asn Thr Ser Met Ala Thr Asn Pro Asn Tyr Thr Met Ser Glu Leu Gly
            165                 170                 175

Asp Ala Phe Ser Tyr Gly Glu Thr Ala Ala Tyr Ile Ile Val Leu Gly
            180                 185                 190

Asp Lys Glu Ala Gly Leu Val Asn Arg Ser Arg Val Glu Tyr Leu Phe
            195                 200                 205
```

Glu Asn Glu Arg Leu Pro Val Glu Leu Gly Trp Ser Arg Ala Arg Glu
210                 215                 220

Asn Ile Thr Phe Asp Asp Leu Ser Thr Met Leu Asn Lys Ile Ile Asn
225                 230                 235                 240

Ala Thr Gly Gly Glu Ser Glu Phe Glu Arg Glu Leu Ala Lys Arg Gly
                245                 250                 255

Gly Val His Val Gly Trp Arg
            260

<210> SEQ ID NO 12
<211> LENGTH: 261
<212> TYPE: PRT
<213> ORGANISM: Artificial Sequence
<220> FEATURE:
<223> OTHER INFORMATION: UPO 12

<400> SEQUENCE: 12

Met Lys Ser Leu Ser Phe Ser Leu Ala Leu Gly Phe Gly Ser Thr Leu
1               5                   10                  15

Val Tyr Ser Ala Pro Ser Pro Ser Ser Gly Trp Gln Ala Pro Gly Pro
                20                  25                  30

Asn Asp Val Arg Ala Pro Cys Pro Met Leu Asn Thr Leu Ala Asn His
            35                  40                  45

Gly Phe Leu Pro His Asp Gly Lys Gly Ile Thr Val Asn Lys Thr Ile
        50                  55                  60

Asp Ala Leu Gly Ser Ala Leu Asn Ile Asp Ala Asn Leu Ser Thr Leu
65                  70                  75                  80

Leu Phe Gly Phe Ala Ala Thr Thr Asn Pro Gln Pro Asn Ala Thr Phe
                85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
        115                 120                 125

Glu Ala Val Phe Asn Gln Thr Lys Ser Phe Trp Thr Gly Asp Ile Ile
130                 135                 140

Asp Val Gln Met Ala Ala Asn Ala Arg Ile Val Arg Leu Leu Thr Ser
145                 150                 155                 160

Asn Leu Thr Asn Pro Glu Tyr Ser Leu Ser Asp Leu Gly Ser Ala Phe
                165                 170                 175

Ser Ile Gly Glu Ser Ala Ala Tyr Ile Gly Ile Leu Gly Asp Lys Lys
            180                 185                 190

Ser Ala Thr Val Pro Lys Ser Trp Val Glu Tyr Leu Phe Glu Asn Glu
        195                 200                 205

Arg Leu Pro Tyr Glu Leu Gly Phe Lys Arg Pro Asn Asp Pro Phe Thr
210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Asp Thr Arg Cys
                245                 250                 255

Pro Tyr Gly Tyr His
            260

<210> SEQ ID NO 13
<211> LENGTH: 283
<212> TYPE: PRT
<213> ORGANISM: Artificial Sequence
<220> FEATURE:

<223> OTHER INFORMATION: UPO 13

<400> SEQUENCE: 13

```
Met Lys Thr Leu Phe Leu Leu Thr Leu Ala Ala Phe Thr Pro Val Phe
1               5                   10                  15

Ala Gly Phe Asp Thr Trp Ala Pro Pro Gly Pro Tyr Asp Val Arg Ala
                20                  25                  30

Pro Cys Pro Met Leu Asn Thr Leu Ala Asn His Gly Phe Leu Pro His
            35                  40                  45

Asp Gly His Glu Ile Thr Arg Glu Gln Thr Glu Asn Ala Leu Phe Asp
        50                  55                  60

Ala Leu His Ile Asp Lys Met Leu Gly Ser Ser Leu Phe Asp Phe Ala
65                  70                  75                  80

Met Thr Thr Asn Pro Val Ala Asn Ser Thr Thr Phe Ser Leu Asn Asp
                85                  90                  95

Leu Gly Asn His Asn Val Leu Glu His Asp Ala Ser Leu Ser Arg Ser
            100                 105                 110

Asp Ala Tyr Phe Gly Asn Thr Leu Thr Phe Asn Gln Thr Val Phe Asp
        115                 120                 125

Glu Thr Lys Ser Tyr Trp Thr Asp Glu Thr Val Thr Ile Glu Met Ala
    130                 135                 140

Ser Asn Ala Arg Leu Ala Arg Ile Lys Thr Ser Asn Ala Thr Asn Pro
145                 150                 155                 160

Thr Tyr Ser Met Ser Glu Leu Gly Asn Gly Phe Thr Lys Gly Glu Ser
                165                 170                 175

Ala Ala Tyr Val Val Ile Phe Gly Asp Lys Ile Ser Gly Thr Val Pro
            180                 185                 190

Arg Ala Trp Val Glu Trp Leu Phe Glu Ile Ala Leu Lys Thr Gln Pro
        195                 200                 205

Ser Thr Pro Ser Ile Lys Pro Thr Gln Thr Pro Ser Ser Pro Thr Arg
    210                 215                 220

Leu Leu Leu Lys Arg Leu Gly Arg Gln Leu Met Leu Ile Val Pro Arg
225                 230                 235                 240

Pro Ile Arg Leu Arg Val Leu Arg Asn Thr Pro Pro Leu Arg Leu Ile
                245                 250                 255

Thr Lys Asn Lys Pro Arg Glu Met Ala Pro Asn Leu Leu Ile Leu Ala
            260                 265                 270

Val His Lys Arg Ala Thr Ser Met Gln Lys Arg
        275                 280
```

<210> SEQ ID NO 14
<211> LENGTH: 225
<212> TYPE: PRT
<213> ORGANISM: Artificial Sequence
<220> FEATURE:
<223> OTHER INFORMATION: UPO 14

<400> SEQUENCE: 14

```
Met Arg Thr Ser Leu Leu Pro Ala Leu Ala Ala Val Ser Pro Val Leu
1               5                   10                  15

Ala Gly Phe Asp Thr Trp Ala Pro Pro Gly Pro Tyr Asp Val Arg Gly
                20                  25                  30

Pro Cys Pro Met Leu Asn Thr Leu Thr Asn His Gly Phe Phe Pro His
            35                  40                  45

Asp Gly Gln Asp Ile Asp Arg Glu Thr Thr Glu Asn Ala Leu Phe Asp
        50                  55                  60
```

Ala Leu His Val Asn Lys Thr Leu Ala Ser Phe Leu Arg Ala Asp Ala
65                  70                  75                  80

Tyr His Gly Ser Val Leu Ala Phe Asn His Thr Ile Phe Glu Glu Thr
                85                  90                  95

Lys Ser Tyr Trp Thr Asp Glu Thr Val Thr Leu Lys Met Ala Ala Asp
            100                 105                 110

Ala Arg Tyr Tyr Arg Ile Lys Ser Ser Gln Ala Thr Asn Pro Thr Tyr
        115                 120                 125

Gln Met Ser Glu Leu Gly Asp Ala Phe Thr Tyr Gly Glu Ser Ala Ala
130                 135                 140

Tyr Val Leu Phe Gly Asp Lys Glu Ser Gln Thr Val Pro Arg Ser
145                 150                 155                 160

Trp Val Glu Trp Leu Phe Glu Lys Glu Gln Leu Pro Gln His Leu Gly
                165                 170                 175

Trp Lys Arg Pro Ala Thr Ser Phe Glu Leu Asn Asp Leu Asp Lys Phe
            180                 185                 190

Met Ala Leu Ile Gln Asn Tyr Thr Gln Glu Ile Glu Glu Pro Ser Cys
        195                 200                 205

Glu Ser Arg Lys Gln Arg Arg Lys Pro Arg Gly Pro Ser His Phe Gly
    210                 215                 220

Phe
225

<210> SEQ ID NO 15
<211> LENGTH: 375
<212> TYPE: PRT
<213> ORGANISM: Artificial Sequence
<220> FEATURE:
<223> OTHER INFORMATION: UPO 15

<400> SEQUENCE: 15

Met Ala Lys Phe Ser Thr Leu Phe Ala Phe Ser Ala Leu Ala Ile Gln
1               5                   10                  15

Ala Ile Ala Leu Pro Gln Tyr Arg Ser Leu Ala Gly Leu Ser Glu Arg
            20                  25                  30

Glu Leu Glu Gly Ile Leu Pro Arg Leu Asn Val Val Thr Pro Pro Pro
        35                  40                  45

Ser Pro Pro Gly Pro Pro Asn Asp Thr Ser Val Lys Leu Val Asn Asp
    50                  55                  60

Ala Ala His Pro Phe Met Pro Leu Gln Asp Gly Asp Ile Arg Gly Pro
65                  70                  75                  80

Cys Pro Gly Leu Asn Thr Leu Ala Ser His Gly Tyr Leu Pro Arg Asn
                85                  90                  95

Gly Ile Ala Thr Pro Ala Gln Ile Ile Asn Ala Val Gln Asp Gly Phe
            100                 105                 110

Ser Met Asp Asn Gly Leu Ala Thr Leu Leu Ala Tyr Ala Thr Met Leu
        115                 120                 125

Val Asp Gly Asn Pro Leu Thr Asn Leu Met Ser Ile Gly Gly Lys Ser
130                 135                 140

Pro Leu Thr Gly Met Asp Pro Pro Gln Pro Ala Ile Val Gly Gly Leu
145                 150                 155                 160

Asp Thr His Ala Val Phe Glu Gly Asp Ala Ser Met Thr Arg Ala Asp
                165                 170                 175

Phe Phe Phe Gly Asp Asn His Ser Phe Asn Gln Thr Leu Phe Asn Gln
            180                 185                 190

```
Phe Ala Asn Phe Ser Asn Gln Phe Gly Asp Gly Asn Tyr Asn Leu Thr
            195                 200                 205

Thr Ala Glu Glu Tyr Arg Phe Phe Arg Ile Gln Gln Ser Ile Ala Glu
210                 215                 220

Asn Pro Gln Phe Ser Phe Ile Ser Pro Arg Phe Phe Thr Ala Tyr Phe
225                 230                 235                 240

Glu Ser Ala Phe Pro Leu Val Phe Phe Val Asp Gly Arg Gln Ala Asp
                245                 250                 255

Gly Gln Leu Ser Val Glu Asn Ala Thr Ser Phe Phe Arg Asp Met Gln
                260                 265                 270

Phe Pro Asp Asp Phe His Arg Ala Asp Gly Ser Gln Thr Ala Asp Leu
                275                 280                 285

Val Asn Asn Ala Ala Thr Ala Ile Phe Ser Ala His Pro Met Gln Pro
290                 295                 300

Gly Gly Asn Asn Gly Thr Val Asn Ser Tyr Thr Phe Asp Pro Asn Ser
305                 310                 315                 320

Ala Asn Phe Thr Glu Gly Cys Lys Leu Tyr Thr Asp Phe Val Asn Asn
                325                 330                 335

Val Val Val Pro Leu Tyr Pro Thr Pro Gln Gly Ala Leu Lys Val Asn
                340                 345                 350

Leu Asn Ala Asn Leu Gly Phe Leu Phe Ser Thr Phe Ser Asn Cys Thr
                355                 360                 365

Gln Val Phe Pro Tyr Gly Gln
                370                 375

<210> SEQ ID NO 16
<211> LENGTH: 371
<212> TYPE: PRT
<213> ORGANISM: Artificial Sequence
<220> FEATURE:
<223> OTHER INFORMATION: UPO 16

<400> SEQUENCE: 16

Met Ala Lys Phe Ser Thr Leu Leu Ala Leu Ser Val Leu Ala Ile Gln
1               5                   10                  15

Ala Val Ala Phe Pro Gln His Gln Pro Leu Ala Gly Leu Thr Glu Arg
                20                  25                  30

Glu Leu Glu Asp Leu Leu Pro Arg Phe Lys Pro Val Val Pro Pro Pro
            35                  40                  45

Pro Pro Gly Pro Pro Lys Asp Thr Ser Val Lys Leu Val Asn Asp Lys
50                  55                  60

Asp His Pro Tyr Glu Pro Leu Arg Lys Gly Asp Ile Arg Gly Pro Cys
65                  70                  75                  80

Pro Gly Leu Asn Thr Leu Ala Ser His Gly Tyr Leu Pro Arg Asn Gly
                85                  90                  95

Val Val Thr Pro Ala Gln Ile Ile Asn Ala Val Gln Asp Gly Phe Gly
                100                 105                 110

Met Asp Asn Glu Leu Ala Ile Leu Leu Ala Tyr Ser Thr Met Leu Thr
            115                 120                 125

Asp Gly Asn Val Val Thr Asn Leu Met Ser Ile Gly Gln Lys Thr Pro
130                 135                 140

Leu Thr Gly Pro Asp Pro Pro Ala Pro Ala Ile Val Gly Gly Leu Asn
145                 150                 155                 160

Thr His Gly Thr Phe Glu Gly Asp Ala Gly Leu Thr Arg Ala Asp Phe
                165                 170                 175
```

-continued

Phe Phe Gly Asp Asn His Ser Phe Asn Gln Thr Leu Phe Asn Glu Phe
            180                 185                 190

Val Glu Phe Ser Asn Lys Phe Gly Gly Val Tyr Asn Gln Thr Val
        195                 200                 205

Ala Ala Glu Tyr Arg Phe Phe Arg Ile Gln Gln Ser Thr Ala Glu Asn
    210                 215                 220

Pro Thr Phe Thr Phe Val Thr Pro Arg Phe Val Thr Ala Tyr Arg Glu
225                 230                 235                 240

Ser Val Phe Pro Phe Ile Phe Phe Val Asp Gly Arg Lys Ala Asp Gly
                245                 250                 255

Gln Leu Ser Met Lys Asp Ala Phe Gly Phe Phe Asn Glu Ser Arg Met
            260                 265                 270

Pro Asp Gly Phe His Arg Ala Asp Gly Ser Lys Thr Ala Asp Leu Val
        275                 280                 285

Gly Asn Ala Ser Asp Ala Ile Phe Ala Ala His Pro Val Gln Pro Gly
    290                 295                 300

Ala Asn Ala Gly Lys Val Asn Thr Tyr Thr Pro Asp Pro Asn Ser Pro
305                 310                 315                 320

Thr Asp Asp Cys Gly Leu Tyr Glu Thr Phe Val Asn Leu Met Val Lys
                325                 330                 335

Gln Tyr Pro Asn Pro Gln Gly Val Leu Arg Thr Asn Leu Asn Leu Asn
            340                 345                 350

Leu Gly Phe Phe Phe Gln Gly Phe Pro Gly Cys Thr Gln Leu Phe Pro
        355                 360                 365

Phe Gly Gln
    370

<210> SEQ ID NO 17
<211> LENGTH: 268
<212> TYPE: PRT
<213> ORGANISM: Artificial Sequence
<220> FEATURE:
<223> OTHER INFORMATION: UPO 17

<400> SEQUENCE: 17

Met Leu Gly Ile Arg Leu Val Ser Leu Leu Ala Phe Thr Gly Ser Ala
1               5                   10                  15

Leu Ala Glu Leu Asp Phe Ser Lys Trp Lys Thr Arg Gln Pro Gly Glu
            20                  25                  30

Leu Arg Ala Pro Cys Pro Ala Met Asn Ser Leu Ala Asn His Gly Phe
        35                  40                  45

Ile Gln Arg Asp Gly Lys Asn Ile Thr Val Glu Gly Leu Thr Pro Val
    50                  55                  60

Leu Lys Glu Val Phe His Leu Ser His Glu Leu Ala Phe Thr Val Ser
65                  70                  75                  80

Gln Leu Gly Leu Phe Thr Ala Leu Asp Pro Ser Lys Gly Val Phe Thr
                85                  90                  95

Leu Gln Asp Leu Thr Asp Arg His Asn Val Phe Glu His Asp Ala Ser
            100                 105                 110

Leu Ser Arg Glu Asp Ala Lys Phe Gly Asp Gln Ser Val Leu His
        115                 120                 125

Lys Gly Gln Phe Gln Lys Phe Met Asp His Pro Lys Gly Glu Lys Tyr
    130                 135                 140

Ile Ser Phe Glu Ala Ala Ala Lys Ala Arg Tyr Ala Met Val Gln Asp
145                 150                 155                 160

Ser Arg Lys Arg Asn Pro Asp Phe Thr Tyr Asp Val Thr His Arg Ile
            165                 170                 175

Thr Ser Tyr Gly Glu Thr Ile Lys Tyr Leu Arg Thr Ile Val Glu Pro
            180                 185                 190

Ser Thr Gly Lys Cys Pro Val Asp Trp Ile Lys Ile Leu Phe Glu Gln
            195                 200                 205

Glu Arg Leu Pro Tyr Asn Glu Gly Trp Arg Pro Pro Thr Asn Glu Leu
            210                 215                 220

Ser Gly Phe Ser Leu Ala Ser Glu Val Leu Glu Leu Ala Leu Ile Thr
225                 230                 235                 240

Pro Glu Lys Leu Pro Val Asp Glu Cys Leu Gly Lys Gly Lys Gly Lys
            245                 250                 255

Gly Asn Cys Lys Arg Arg Arg Ser Tyr Leu Gly Ile
            260                 265

<210> SEQ ID NO 18
<211> LENGTH: 371
<212> TYPE: PRT
<213> ORGANISM: Artificial Sequence
<220> FEATURE:
<223> OTHER INFORMATION: UPO 18

<400> SEQUENCE: 18

Met Asn Pro Phe Leu Lys Leu Ala Val Leu Ala Leu Val Thr Ala Pro
1               5                   10                  15

Leu Ala Gly Ala Phe Pro Ser His Arg Ser Leu Gly Gly Leu Ser Ser
            20                  25                  30

Glu Gln Leu Asp Arg Ile Phe Pro Thr Leu Lys Val Ala Pro Pro Glu
            35                  40                  45

Gly Pro Pro Pro Pro Gln Asp Asp Thr Ser Thr Arg Leu Val Asp Asp
        50                  55                  60

Ala Asp His Pro Phe Met Pro Ala Gly Pro Asn Asp Met Arg Gly Pro
65                  70                  75                  80

Cys Pro Gly Leu Asn Thr Leu Ala Ser His Gly Tyr Leu Pro Arg Asn
                85                  90                  95

Gly Ile Ala Thr Pro Ala Gln Val Ile Asn Ala Thr Met Gln Gly Phe
            100                 105                 110

Asn Met Glu Phe Ser Leu Ala Lys Phe Val Thr Tyr Ala Ala Phe Leu
            115                 120                 125

Val Asp Gly Asn Pro Ile Thr Asn Leu Met Ser Ile Gly Gly Lys Ser
    130                 135                 140

Asp Leu Thr Gly Glu Asp Pro Pro Asp Pro Ala Thr Val Gly Gly Leu
145                 150                 155                 160

Asn Thr His Ala Val Phe Glu Gly Asp Ala Ser Met Thr Arg Ala Asp
                165                 170                 175

Ala Phe Phe Gly Asp Asn His Ser Phe Asn Gln Thr Leu Trp Asp Gly
            180                 185                 190

Phe Val Asp Phe Ser Asn Arg Phe Gly Ala Gly Lys Tyr Asn Leu Thr
            195                 200                 205

Val Ala Thr Glu Leu Arg Ile Gln Arg Ile Gln Asp Ser Ile Ala Thr
    210                 215                 220

Asn Pro Gln Phe Ser Phe Val Ser Pro Arg Phe Ile Thr Ala Tyr Ala
225                 230                 235                 240

Glu Ser Thr Phe Pro Ile Asn Phe Phe Ile Asp Gly Arg Gln Gln Asp
                245                 250                 255

```
Gly Gln Leu Asp Leu Asp Ala Ala Ile Ser Phe Phe Arg Asp Met Arg
            260                 265                 270

Tyr Pro Ser Gly Phe Phe Arg Ala Pro Lys Pro Met Gly Val Glu Gly
            275                 280                 285

Ile Glu Thr Ile Ile Ala Ala His Pro Ile Pro Ala Gly Ala Asn Asn
290                 295                 300

Gly Ala Val Asn Thr Tyr Thr Pro Asp Pro His Ser Gly Asp Phe Asn
305                 310                 315                 320

Ser Phe Cys Thr Val Tyr Thr Asn Phe Val Asn Glu Thr Ile Arg Gly
                325                 330                 335

Leu Tyr Pro Ser Pro Thr Gly Ile Leu Lys Asp Ser Leu Asn Arg Asn
            340                 345                 350

Leu Asp Phe Leu His Asp Phe Val Ser Gly Cys Pro Gln Ile Phe Pro
            355                 360                 365

Trp Gly Arg
        370

<210> SEQ ID NO 19
<211> LENGTH: 321
<212> TYPE: PRT
<213> ORGANISM: Artificial Sequence
<220> FEATURE:
<223> OTHER INFORMATION: CPO 19

<400> SEQUENCE: 19

Met Phe Ser Lys Val Leu Pro Phe Val Gly Ala Val Ala Ala Leu Pro
1               5                   10                  15

His Ser Val Arg Gln Glu Pro Gly Ser Gly Ile Gly Tyr Pro Tyr Asp
                20                  25                  30

Asn Asn Thr Leu Pro Tyr Val Ala Pro Gly Pro Thr Asp Ser Arg Ala
            35                  40                  45

Pro Cys Pro Ala Leu Asn Ala Leu Ala Asn His Gly Tyr Ile Pro His
        50                  55                  60

Asp Gly Arg Ala Ile Ser Arg Glu Thr Leu Gln Asn Ala Phe Leu Asn
65                  70                  75                  80

His Met Gly Ile Ala Asn Ser Val Ile Glu Leu Ala Leu Thr Asn Ala
                85                  90                  95

Phe Val Val Cys Glu Tyr Val Thr Gly Ser Asp Cys Gly Asp Ser Leu
            100                 105                 110

Val Asn Leu Thr Leu Leu Ala Glu Pro His Ala Phe Glu His Asp His
        115                 120                 125

Ser Phe Ser Arg Lys Asp Tyr Lys Gln Gly Val Ala Asn Ser Asn Asp
    130                 135                 140

Phe Ile Asp Asn Arg Asn Phe Asp Ala Glu Thr Phe Gln Thr Ser Leu
145                 150                 155                 160

Asp Val Val Ala Gly Lys Thr His Phe Asp Tyr Ala Asp Met Asn Glu
                165                 170                 175

Ile Arg Leu Gln Arg Glu Ser Leu Ser Asn Glu Leu Asp Phe Pro Gly
            180                 185                 190

Trp Phe Thr Glu Ser Lys Pro Ile Gln Asn Val Glu Ser Gly Phe Ile
        195                 200                 205

Phe Ala Leu Val Ser Asp Phe Asn Leu Pro Asp Asn Asp Glu Asn Pro
    210                 215                 220

Leu Val Arg Ile Asp Trp Trp Lys Tyr Trp Phe Thr Asn Glu Ser Phe
225                 230                 235                 240
```

Pro Tyr His Leu Gly Trp His Pro Ser Pro Ala Arg Glu Ile Glu
            245                 250                 255

Phe Val Thr Ser Ala Ser Ser Ala Val Leu Ala Ala Ser Val Thr Ser
        260                 265                 270

Thr Pro Ser Ser Leu Pro Ser Gly Ala Ile Gly Pro Gly Ala Glu Ala
        275                 280                 285

Val Pro Leu Ser Phe Ala Ser Thr Met Thr Pro Phe Leu Leu Ala Thr
    290                 295                 300

Asn Ala Pro Tyr Tyr Ala Gln Asp Pro Thr Leu Arg Pro Gln Arg Gln
305                 310                 315                 320

Ala

<210> SEQ ID NO 20
<211> LENGTH: 376
<212> TYPE: PRT
<213> ORGANISM: Artificial Sequence
<220> FEATURE:
<223> OTHER INFORMATION: CPO 20

<400> SEQUENCE: 20

Met Phe Ser Lys Ile Leu Pro Leu Val Gly Val Ala Ala Ala Leu Pro
1               5                   10                  15

His Trp Leu Gln Leu Arg Gln Glu Pro Asn Ser Gly Ile Gly Tyr Pro
            20                  25                  30

Tyr Asp Asn His Thr Lys Pro Tyr Val His Pro Gly Pro His Asp Ser
        35                  40                  45

Arg Ala Pro Cys Pro Ala Leu Asn Ala Leu Ala Asn His Gly Tyr Ile
    50                  55                  60

Pro His Asn Gly Arg Ala Ile Thr Lys Glu Asn Leu Gln Asn Ala Phe
65                  70                  75                  80

Leu Glu His Met Gly Ile Gly Asn Ser Val Ile Ala Leu Ala Leu Thr
                85                  90                  95

Asn Ala Phe Val Val Cys Glu Tyr Val Thr Gly Gln Asp Cys Gly Asp
            100                 105                 110

Thr Leu Val Asn Leu Thr Leu Leu Ser Glu Pro His Ala Phe Glu His
        115                 120                 125

Asp His Ser Phe Ser Arg Lys Asp Tyr Lys Gln Gly Val Ser Asn Phe
    130                 135                 140

Asn Glu Ile Val Asp Asn Arg Asn Phe Asp Leu Ser Thr Phe Glu Thr
145                 150                 155                 160

Ser Leu Asp Val Val Ala Gly Gln Thr His Phe Gly Tyr Ala Glu Met
                165                 170                 175

Asn Gln Ile Arg Leu Gln Arg Glu Ser Leu Ser Asn Glu Ala Asp Phe
            180                 185                 190

Pro Gly Trp Phe Thr Glu Ser Lys Pro Ile Gln Glu Val Glu Ala Gly
        195                 200                 205

Phe Ile Phe Ala Leu Val Ser Asp Phe Asn Leu Pro Asp Asn Asp Glu
    210                 215                 220

Asn Pro Leu Val Arg Val Asp Trp Trp Lys Tyr Trp Phe Ile Asn Glu
225                 230                 235                 240

Ser Phe Pro Tyr His Leu Gly Trp His Pro Thr Pro Ala Arg Glu
                245                 250                 255

Ile Glu Phe Val Thr Ser Ala Ser Ser Ala Ile Leu Ala Ala Ala Val
            260                 265                 270

```
Thr Ser Thr Pro Ser Ser Leu Pro Ser Gly Ala Ile Gly Pro Gly Ala
        275                 280                 285

Glu Ala Val Pro Leu Ser Phe Ala Ser Thr Met Thr Pro Phe Leu Leu
    290                 295                 300

Ala Thr Asp Ile Pro Tyr Phe Ala His Pro Thr Leu Gly Pro Asn Asp
305                 310                 315                 320

Lys Arg Glu Ala Ala Pro Ala Pro Ala Thr Thr Ser Thr Ala Thr
                325                 330                 335

Phe Lys Asn Pro Tyr Leu Glu Pro Ile Gly Thr Gln Asp Ile Lys Asn
                340                 345                 350

Gln Gln Ala Tyr Val Ser Ser Lys Ala Ala Met Ser Ser Ala Met
            355                 360                 365

Ala Val Asn Lys Ala Arg Ser Leu
    370                 375

<210> SEQ ID NO 21
<211> LENGTH: 371
<212> TYPE: PRT
<213> ORGANISM: Artificial Sequence
<220> FEATURE:
<223> OTHER INFORMATION: UPO 21

<400> SEQUENCE: 21

Met Lys Tyr Phe Pro Leu Phe Pro Thr Leu Val Phe Ala Ala Arg Val
1               5                   10                  15

Val Ala Phe Pro Ala Tyr Ala Ser Leu Ala Gly Leu Ser Gln Gln Glu
                20                  25                  30

Leu Asp Ala Ile Ile Pro Thr Leu Glu Ala Arg Glu Pro Gly Leu Pro
            35                  40                  45

Pro Gly Pro Leu Glu Asn Ser Ser Ala Lys Leu Val Asn Asp Glu Ala
        50                  55                  60

His Pro Trp Lys Pro Leu Arg Pro Gly Asp Ile Arg Gly Pro Cys Pro
65                  70                  75                  80

Gly Leu Asn Thr Leu Ala Ser His Gly Tyr Leu Pro Arg Asn Gly Val
                85                  90                  95

Ala Thr Pro Val Gln Ile Ile Asn Ala Val Gln Glu Gly Leu Asn Phe
                100                 105                 110

Asp Asn Gln Ala Ala Val Phe Ala Thr Tyr Ala Ala His Leu Val Asp
            115                 120                 125

Gly Asn Leu Ile Thr Asp Leu Leu Ser Ile Gly Arg Lys Thr Arg Leu
130                 135                 140

Thr Gly Pro Asp Pro Pro Pro Ala Ser Val Gly Gly Leu Asn Glu
145                 150                 155                 160

His Gly Thr Phe Glu Gly Asp Ala Ser Met Thr Arg Gly Asp Ala Phe
                165                 170                 175

Phe Gly Asn Asn His Asp Phe Asn Glu Thr Leu Phe Glu Gln Leu Val
            180                 185                 190

Asp Tyr Ser Asn Arg Phe Gly Gly Lys Tyr Asn Leu Thr Val Ala
            195                 200                 205

Gly Glu Leu Arg Phe Lys Arg Ile Gln Asp Ser Ile Ala Thr Asn Pro
210                 215                 220

Asn Phe Ser Phe Val Asp Phe Arg Phe Thr Ala Tyr Gly Glu Thr
225                 230                 235                 240

Thr Phe Pro Ala Asn Leu Phe Val Asp Gly Arg Arg Asp Asp Gly Gln
                245                 250                 255
```

Leu Asp Met Asp Ala Ala Arg Ser Phe Phe Gln Phe Ser Arg Met Pro
                260                 265                 270

Asp Asp Phe Phe Arg Ala Pro Ser Pro Arg Ser Gly Thr Gly Val Glu
            275                 280                 285

Val Val Ile Gln Ala His Pro Met Gln Pro Gly Arg Asn Val Gly Lys
        290                 295                 300

Ile Asn Ser Tyr Thr Val Asp Pro Thr Ser Ser Asp Phe Ser Thr Pro
305                 310                 315                 320

Cys Leu Met Tyr Glu Lys Phe Val Asn Ile Thr Val Lys Ser Leu Tyr
                325                 330                 335

Pro Asn Pro Thr Val His Val Arg Lys Ala Leu Asn Thr Asn Leu Asp
            340                 345                 350

Phe Phe Phe Gln Gly Val Ala Ala Gly Cys Thr Gln Val Phe Pro Tyr
            355                 360                 365

Gly Arg Asp
    370

<210> SEQ ID NO 22
<211> LENGTH: 262
<212> TYPE: PRT
<213> ORGANISM: Artificial Sequence
<220> FEATURE:
<223> OTHER INFORMATION: UPO22

<400> SEQUENCE: 22

Met Lys Leu Val Tyr Leu Ser Ser Ala Val Ala Phe Gly Ser Ala Ile
1               5                   10                  15

Ala Asp Thr Ala Pro Trp Glu Gly Pro Gly Pro Asn Asp Val Arg Gly
            20                  25                  30

Pro Cys Pro Met Leu Asn Thr Leu Ala Asn His Gly Phe Leu Pro His
        35                  40                  45

Asp Gly Lys Asn Ile His Val Asn Lys Thr Val Asp Ala Leu Ser Ser
    50                  55                  60

Ala Leu Asn Ile Asp Pro Glu Leu Gly Ser Phe Leu His Ser Phe Ala
65                  70                  75                  80

Val Thr Ala Asn Pro Gln Pro Asn Ala Thr Trp Trp Asn Leu Asp His
                85                  90                  95

Leu Ser Arg His Asn Ile Leu Glu His Asp Ala Ser Leu Ser Arg Gln
                100                 105                 110

Asp Ala Tyr Phe Gly Ala Pro Asp Val Phe Asn Glu Ala Val Phe Asn
            115                 120                 125

Gln Thr Lys Ser Tyr Trp Thr Gly Asp Val Ile Thr Leu Gln Met Ala
    130                 135                 140

Ala Asn Ala Arg Leu Ala Arg Leu Met Thr Ser Asn Leu Thr Asn Pro
145                 150                 155                 160

Glu Tyr Ser Met Ser Asp Leu Gly Ser Ser Phe Ser Ile Gly Glu Ser
                165                 170                 175

Val Ala Tyr Val Ala Ile Leu Gly Ser Lys Glu Thr Arg Thr Val Pro
            180                 185                 190

Lys Ala Tyr Val Glu Tyr Leu Phe Glu Lys Glu Arg Leu Pro Tyr Glu
        195                 200                 205

Leu Gly Phe Lys Lys Ala Glu Thr Pro Met Thr Glu Thr Asp Leu Gly
    210                 215                 220

Asn Leu Met Asp Glu Leu Ile Ser Leu Gln His Phe Pro Gln Ser Pro
225                 230                 235                 240

```
Gly Lys Ile Ala Lys Arg Ser Glu Arg Pro Ser Glu Lys Arg Ala Glu
                245                 250                 255

Lys Arg Cys Pro Phe His
            260
```

<210> SEQ ID NO 23
<211> LENGTH: 267
<212> TYPE: PRT
<213> ORGANISM: Artificial Sequence
<220> FEATURE:
<223> OTHER INFORMATION: UPO23

<400> SEQUENCE: 23

```
Met Lys Thr Ala Thr Leu Leu Phe Leu Ala Ala Gly Leu Thr Gln Thr
1               5                   10                  15

Gln Ala Phe Pro Ser Gln Gly Ala Ala Pro His Pro Leu Pro Trp Ser
            20                  25                  30

Pro Pro Gly Pro Asn Asp Val Arg Ala Pro Cys Pro Met Leu Asn Thr
            35                  40                  45

Leu Ala Asn His Gly Tyr Leu Pro His Asn Gly Lys Asn Ile Thr Glu
        50                  55                  60

Gln His Thr Ile Asn Ala Leu Tyr Asn Ala Leu Gly Ile Asp Ala Glu
65                  70                  75                  80

Leu Ser Ala Phe Leu His Gln Glu Ala Val Thr Thr Asn Pro Thr Pro
                85                  90                  95

Asn Ala Thr Thr Phe Ser Leu Asn Asp Leu Ser Arg His Asp Ile Leu
            100                 105                 110

Glu His Asp Ala Ser Leu Ser Arg Gln Asp Ala Tyr Phe Gly Asp Asn
            115                 120                 125

His Asp Phe Asn Gln Thr Ile Phe Asp Glu Thr Arg Ser Tyr Trp Thr
        130                 135                 140

Ser Pro Ile Ile Asp Val Lys Gln Ala Ala Leu Ser Arg Gln Ala Arg
145                 150                 155                 160

Val Asn Thr Ser Met Ala Thr Asn Pro Asn Tyr Thr Met Ser Glu Leu
                165                 170                 175

Gly Ala Ser Phe Ser Tyr Gly Glu Thr Ala Ala Tyr Ile Ile Val Leu
            180                 185                 190

Gly Asp Lys Glu Asn Gly Leu Val Asn Arg Ser Arg Val Glu Tyr Leu
            195                 200                 205

Phe Glu Asn Glu Arg Leu Pro Leu Asp Leu Gly Trp Thr Arg Ala Lys
        210                 215                 220

Glu Asn Ile Thr Phe Asp Asp Leu Arg Thr Met Leu Asn Arg Ile Val
225                 230                 235                 240

Asn Ala Thr Gly Gly Glu Ser Glu Phe Asp Arg Glu Leu Ala Lys Arg
                245                 250                 255

Gly Gly Val His Val Gly Arg Trp Arg Gly Tyr
            260                 265
```

<210> SEQ ID NO 24
<211> LENGTH: 265
<212> TYPE: PRT
<213> ORGANISM: Artificial Sequence
<220> FEATURE:
<223> OTHER INFORMATION: UPO24

<400> SEQUENCE: 24

```
Met Lys Thr Thr Thr Leu Leu Cys Leu Ala Ala Leu Thr Gln Thr
1               5                   10                  15
```

Tyr Ala Phe Pro Gln Gln Gly Ala Pro His Pro Leu Pro Trp Ser Pro
            20                  25                  30

Pro Gly Pro Asn Asp Val Arg Ala Pro Cys Pro Met Leu Asn Thr Leu
            35                  40                  45

Ala Asn His Gly Tyr Leu Pro His Asn Gly Lys Asp Ile Thr Glu Arg
 50                  55                  60

His Thr Ile Asn Ala Leu Tyr Asn Ala Leu Gly Ile Glu Glu Glu Leu
 65                  70                  75                  80

Ala Ile Tyr Leu His Gln Glu Ala Val Thr Thr Asn Pro Ala Pro Asn
                85                  90                  95

Ala Thr Thr Phe Ser Leu Asn Asp Leu Ser Arg His Asp Ile Leu Glu
            100                 105                 110

His Asp Ala Ser Leu Ser Arg Gln Asp Ala Tyr Phe Gly Asp Asn His
            115                 120                 125

Asp Phe Asn Gln Thr Ile Phe Asp Glu Thr Arg Ser Tyr Trp Thr Ser
130                 135                 140

Pro Ile Ile Asp Val Lys Gln Ala Ala Val Ser Arg Gln Ala Arg Val
145                 150                 155                 160

Asn Thr Ser Met Ala Thr Asn Pro Asn Tyr Thr Met Ser Glu Leu Gly
            165                 170                 175

Asp Ser Phe Ser Tyr Gly Glu Thr Ala Ala Tyr Ile Ile Val Leu Gly
            180                 185                 190

Asp Lys Glu Lys Gly Leu Val Asn Arg Ser Arg Val Glu Tyr Leu Phe
            195                 200                 205

Glu Asn Glu Arg Leu Pro Leu Asp Leu Gly Trp Ser Arg Ala Lys Glu
            210                 215                 220

Asn Ile Thr Phe Asp Asp Leu Ser Thr Met Leu Gln Arg Ile Ile Asn
225                 230                 235                 240

Ala Thr Gly Gly Glu Ser Glu Phe Asp Arg Glu Leu Ala Lys Arg Gly
            245                 250                 255

Gly Val His Val Gly Ser Trp Arg Gly
            260                 265

<210> SEQ ID NO 25
<211> LENGTH: 267
<212> TYPE: PRT
<213> ORGANISM: Artificial Sequence
<220> FEATURE:
<223> OTHER INFORMATION: UPO25

<400> SEQUENCE: 25

Met Lys Thr Thr Pro Leu Leu Phe Phe Ala Ala Gly Leu Ala Gln Thr
1               5                   10                  15

His Ala Phe Pro Ser Gln Gly Gly Ala Pro His Pro Leu Pro Trp Ser
            20                  25                  30

Pro Pro Gly Pro Asn Asp Val Arg Ala Pro Cys Pro Met Leu Asn Thr
            35                  40                  45

Leu Ala Asn His Gly Tyr Leu Pro His Asn Gly Lys Asp Ile Thr Glu
 50                  55                  60

Gln His Thr Ile Asn Ala Leu Tyr Asn Ala Leu Gly Ile Asp Ala Glu
 65                  70                  75                  80

Leu Ala Thr Tyr Leu His Gln Glu Ala Val Thr Thr Asn Pro Ala Pro
                85                  90                  95

Asn Ala Thr Thr Phe Ser Leu Asn Asp Leu Ser Arg His Asp Ile Leu
            100                 105                 110

```
Glu His Asp Ala Ser Leu Ser Arg Gln Asp Ala Phe Phe Gly Asp Asn
            115                 120                 125

His Asp Phe Asn Gln Thr Ile Phe Asp Glu Thr Arg Ser Tyr Trp Thr
130                 135                 140

Ser Pro Ile Ile Asp Val Met Gln Ala Ala Leu Ser Arg Gln Ala Arg
145                 150                 155                 160

Val Asp Thr Ser Met Ala Thr Asn Pro Asn Tyr Thr Met Ser Glu Leu
                165                 170                 175

Gly Ala Ser Phe Ser Tyr Gly Glu Thr Ala Ala Tyr Ile Ile Val Leu
                180                 185                 190

Gly Asp Lys Glu Asn Gly Leu Val Asn Arg Ser Arg Val Glu Tyr Leu
            195                 200                 205

Phe Glu Asn Glu Arg Leu Pro Leu Asp Leu Gly Trp Thr Arg Ala Lys
210                 215                 220

Glu Asn Ile Thr Phe Asp Asp Leu Ser Thr Met Leu Asn Arg Ile Val
225                 230                 235                 240

Asn Ala Thr Gly Gly Glu Ser Glu Phe Asp Arg Glu Leu Ala Lys Arg
                245                 250                 255

Gly Gly Val His Val Gly Lys Trp Arg Gly Tyr
            260                 265

<210> SEQ ID NO 26
<211> LENGTH: 60
<212> TYPE: PRT
<213> ORGANISM: Artificial Sequence
<220> FEATURE:
<223> OTHER INFORMATION: Conserved Motif

<400> SEQUENCE: 26

Tyr Asp Asn Asn Thr Leu Pro Tyr Val Ala Pro Gly Pro Thr Asp Ser
1               5                   10                  15

Arg Ala Pro Cys Pro Ala Leu Asn Ala Leu Ala Asn His Gly Tyr Ile
            20                  25                  30

Pro His Asp Gly Arg Ala Ile Ser Arg Glu Thr Leu Gln Asn Ala Phe
        35                  40                  45

Leu Asn His Met Gly Ile Ala Asn Ser Val Ile Glu
    50                  55                  60

<210> SEQ ID NO 27
<211> LENGTH: 59
<212> TYPE: PRT
<213> ORGANISM: Artificial Sequence
<220> FEATURE:
<223> OTHER INFORMATION: Conserved Motif

<400> SEQUENCE: 27

Val Asn Asp Lys Asp His Pro Trp Lys Pro Leu Arg Pro Gly Asp Ile
1               5                   10                  15

Arg Gly Pro Cys Pro Gly Leu Asn Thr Leu Ala Ser His Gly Tyr Leu
            20                  25                  30

Pro Arg Asn Gly Val Ala Thr Pro Ala Gln Ile Ile Asn Ala Val Gln
        35                  40                  45

Glu Gly Phe Asn Met Asp Asn Ser Val Ala Leu
    50                  55

<210> SEQ ID NO 28
<211> LENGTH: 48
<212> TYPE: PRT
```

```
<213> ORGANISM: Artificial Sequence
<220> FEATURE:
<223> OTHER INFORMATION: Conserved Motif

<400> SEQUENCE: 28

Leu Ala Leu Thr Asn Ala Phe Val Val Cys Glu Tyr Val Thr Gly Ser
1               5                   10                  15

Asp Cys Gly Asp Ser Leu Val Asn Leu Thr Leu Leu Ala Glu Pro His
            20                  25                  30

Ala Phe Glu His Asp His Ser Phe Ser Arg Lys Asp Tyr Lys Gln Gly
        35                  40                  45

<210> SEQ ID NO 29
<211> LENGTH: 60
<212> TYPE: PRT
<213> ORGANISM: Artificial Sequence
<220> FEATURE:
<223> OTHER INFORMATION: Conserved Motif

<400> SEQUENCE: 29

Phe Ala Thr Tyr Glu Ala His Leu Met Val Gly Asn Leu Leu Thr Asp
1               5                   10                  15

Leu Leu Ser Ile Gly Arg Lys Thr Pro Leu Thr Gly Pro Asp Leu Pro
            20                  25                  30

Pro Pro Ala Asn Ile Gly Gly Leu Ser Glu His Gly Leu Phe Glu Gly
        35                  40                  45

Asp Ala Ser Met Thr Arg Gly Asp Ala Phe Phe Gly
    50                  55                  60

<210> SEQ ID NO 30
<211> LENGTH: 261
<212> TYPE: PRT
<213> ORGANISM: Artificial Sequence
<220> FEATURE:
<223> OTHER INFORMATION: UPO 12 variant

<400> SEQUENCE: 30

Met Lys Ser Leu Ser Phe Ser Leu Ala Leu Gly Phe Gly Ser Thr Leu
1               5                   10                  15

Val Tyr Ser Ala Pro Ser Pro Phe Ser Gly Trp Gln Ala Pro Gly Pro
            20                  25                  30

Asn Asp Val Arg Ala Pro Cys Pro Met Leu Asn Thr Leu Ala Asn His
        35                  40                  45

Gly Phe Leu Pro His Asp Gly Lys Gly Ile Thr Val Asn Lys Thr Ile
    50                  55                  60

Asp Ala Leu Gly Ser Ala Leu Asn Ile Asp Ala Asn Leu Ser Thr Leu
65                  70                  75                  80

Leu Phe Gly Phe Ala Ala Thr Thr Asn Pro Gln Pro Asn Ala Thr Phe
                85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
        115                 120                 125

Glu Ala Val Phe Asn Gln Thr Lys Ser Phe Trp Thr Gly Asp Ile Ile
    130                 135                 140

Asp Val Gln Met Ala Ala Asn Ala Arg Ile Val Arg Leu Leu Thr Ser
145                 150                 155                 160

Asn Leu Thr Asn Pro Glu Tyr Ser Leu Ser Asp Leu Gly Ser Ala Phe
                165                 170                 175
```

Ser Ile Gly Glu Ser Ala Ala Tyr Ile Gly Ile Leu Gly Asp Lys Lys
            180                 185                 190

Ser Ala Thr Val Pro Lys Ser Trp Val Glu Tyr Leu Phe Glu Asn Glu
            195                 200                 205

Arg Leu Pro Tyr Glu Leu Gly Phe Lys Arg Pro Asn Asp Pro Phe Thr
210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Asp Thr Arg Cys
                245                 250                 255

Pro Tyr Gly Tyr His
            260

<210> SEQ ID NO 31
<211> LENGTH: 261
<212> TYPE: PRT
<213> ORGANISM: Artificial Sequence
<220> FEATURE:
<223> OTHER INFORMATION: UPO 12 variant

<400> SEQUENCE: 31

Met Lys Ser Leu Ser Phe Ser Leu Ala Leu Gly Phe Gly Ser Thr Leu
1               5                   10                  15

Val Tyr Ser Ala Pro Ser Pro Ser Ser Gly Trp Gln Ala Pro Gly Pro
            20                  25                  30

Asn Asp Val Arg Ala Pro Cys Pro Met Leu Asn Thr Leu Ala Asn His
            35                  40                  45

Gly Phe Leu Pro His Asp Gly Lys Gly Ile Thr Val Asn Lys Thr Ile
50                  55                  60

Asp Ala Leu Gly Ser Ala Leu Asn Ile Asp Ala Asn Leu Ser Thr Leu
65                  70                  75                  80

Leu Phe Gly Phe Ala Ala Thr Thr Asn Pro Gln Pro Asn Ala Thr Phe
                85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
            115                 120                 125

Glu Ala Val Phe Asn Gln Thr Lys Ser Phe Trp Thr Gly Asp Ile Ile
            130                 135                 140

Tyr Val Gln Met Ala Ala Asn Ala Arg Ile Val Arg Leu Leu Thr Ser
145                 150                 155                 160

Asn Leu Thr Asn Pro Glu Tyr Ser Leu Ser Asp Leu Gly Ser Ala Phe
                165                 170                 175

Ser Ile Gly Glu Ser Ala Ala Tyr Ile Gly Ile Leu Gly Asp Lys Lys
            180                 185                 190

Ser Ala Thr Val Pro Lys Ser Trp Val Glu Tyr Leu Phe Glu Asn Glu
            195                 200                 205

Arg Leu Pro Tyr Glu Leu Gly Phe Lys Arg Pro Asn Asp Pro Phe Thr
210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Asp Thr Arg Cys
                245                 250                 255

Pro Tyr Gly Tyr His
            260

<210> SEQ ID NO 32
<211> LENGTH: 261
<212> TYPE: PRT
<213> ORGANISM: Artificial Sequence
<220> FEATURE:
<223> OTHER INFORMATION: UPO 12 variant

<400> SEQUENCE: 32

```
Met Lys Ser Leu Ser Phe Ser Leu Ala Leu Gly Phe Gly Ser Thr Leu
1               5                   10                  15

Val Tyr Ser Ala Pro Ser Pro Ser Ser Gly Trp Gln Ala Pro Gly Pro
            20                  25                  30

Asn Asp Val Arg Ala Pro Cys Pro Met Leu Asn Thr Leu Ala Asn His
        35                  40                  45

Gly Phe Leu Pro His Asp Gly Lys Gly Ile Thr Val Asn Lys Thr Ile
    50                  55                  60

Asp Ala Leu Gly Ser Ala Leu Asn Ile Asp Ala Asn Leu Ser Thr Leu
65                  70                  75                  80

Leu Phe Gly Phe Ala Ala Thr Thr Asn Pro Gln Pro Asn Ala Thr Phe
                85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
        115                 120                 125

Glu Ala Val Phe Asn Gln Thr Lys Ser Phe Trp Thr Gly Asp Ile Ile
130                 135                 140

Asp Val Gln Met Ala Ala Asn Ala Arg Ile Val Arg Leu Leu Thr Ser
145                 150                 155                 160

Asn Leu Thr Asn Pro Glu Tyr Ser Leu Ser Asp Leu Gly Ser Ala Phe
                165                 170                 175

Ser Ile Gly Glu Ser Ala Ala Tyr Ile Gly Ile Leu Gly Asp Lys Lys
            180                 185                 190

Ser Ala Thr Val Pro Lys Ser Trp Val Glu Tyr Leu Phe Glu Asn Glu
        195                 200                 205

Arg Leu Pro Tyr Glu Leu Gly Phe Lys Arg Pro Asn Asp Pro Phe Thr
    210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Asp Thr Arg Ser
                245                 250                 255

Pro Tyr Gly Tyr His
            260
```

<210> SEQ ID NO 33
<211> LENGTH: 255
<212> TYPE: PRT
<213> ORGANISM: Artificial Sequence
<220> FEATURE:
<223> OTHER INFORMATION: UPO 12 variant

<400> SEQUENCE: 33

```
Met Lys Ser Leu Ser Phe Ser Leu Ala Leu Gly Phe Gly Ser Thr Leu
1               5                   10                  15

Val Tyr Ser Ala Pro Ser Pro Ser Ser Gly Trp Gln Ala Pro Gly Pro
            20                  25                  30

Asn Asp Val Arg Ala Pro Cys Pro Met Leu Asn Thr Leu Ala Asn His
```

```
                35                  40                  45
Gly Phe Leu Pro His Asp Gly Lys Gly Ile Thr Val Asn Lys Thr Ile
         50                  55                  60

Asp Ala Leu Gly Ser Ala Leu Asn Ile Asp Ala Asn Leu Ser Thr Leu
 65                  70                  75                  80

Leu Phe Gly Phe Ala Ala Thr Thr Asn Pro Gln Pro Asn Ala Thr Phe
                 85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
        115                 120                 125

Glu Ala Val Phe Asn Gln Thr Lys Ser Phe Trp Thr Gly Asp Ile Ile
    130                 135                 140

Asp Val Gln Met Ala Ala Asn Ala Arg Ile Val Arg Leu Leu Thr Ser
145                 150                 155                 160

Asn Leu Thr Asn Pro Glu Tyr Ser Leu Ser Asp Leu Gly Ser Ala Phe
                165                 170                 175

Ser Ile Gly Glu Ser Ala Ala Tyr Ile Gly Ile Leu Gly Asp Lys Lys
            180                 185                 190

Ser Ala Thr Val Pro Lys Ser Trp Val Glu Tyr Leu Phe Glu Asn Glu
        195                 200                 205

Arg Leu Pro Tyr Glu Leu Gly Phe Lys Arg Pro Asn Asp Pro Phe Thr
    210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Asp Thr Arg
                245                 250                 255

<210> SEQ ID NO 34
<211> LENGTH: 261
<212> TYPE: PRT
<213> ORGANISM: Artificial Sequence
<220> FEATURE:
<223> OTHER INFORMATION: UPO 12 variant

<400> SEQUENCE: 34

Met Lys Ser Leu Ser Phe Ser Leu Ala Leu Gly Phe Gly Ser Thr Leu
 1               5                  10                  15

Val Tyr Ser Ala Pro Ser Pro Ser Ser Gly Trp Gln Ala Pro Gly Pro
                20                  25                  30

Asn Asp Val Arg Ala Pro Cys Pro Met Leu Asn Thr Leu Ala Asn His
            35                  40                  45

Gly Phe Leu Pro His Asp Gly Lys Gly Ile Thr Val Asn Lys Thr Ile
         50                  55                  60

Asp Ala Leu Gly Ser Ala Leu Asn Ile Asp Ala Asn Leu Ser Thr Leu
 65                  70                  75                  80

Leu Phe Gly Phe Ala Ala Thr Thr Asn Pro Gln Pro Asn Ala Thr Phe
                 85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
        115                 120                 125

Glu Ala Val Phe Asn Gln Thr Lys Ser Phe Trp Thr Gly Asp Ile Ile
    130                 135                 140

Asp Val Gln Met Ala Ala Asn Ala Arg Ile Val Arg Leu Leu Thr Ser
```

```
145                 150                 155                 160
Asn Leu Thr Asn Pro Glu Tyr Ser Leu Ser Asp Leu Gly Ser Ala Phe
                165                 170                 175

Ser Ile Gly Glu Ser Ala Ala Tyr Ile Gly Ile Leu Gly Asp Lys Lys
                180                 185                 190

Ser Ala Thr Val Pro Lys Ser Trp Val Glu Tyr Leu Phe Glu Asn Glu
                195                 200                 205

Arg Leu Pro Tyr Glu Leu Gly Phe Lys Arg Pro Asn Asp Pro Phe Thr
                210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Asn Thr Arg Cys
                245                 250                 255

Pro Tyr Gly Tyr His
                260

<210> SEQ ID NO 35
<211> LENGTH: 261
<212> TYPE: PRT
<213> ORGANISM: Artificial Sequence
<220> FEATURE:
<223> OTHER INFORMATION: UPO 12 variant

<400> SEQUENCE: 35

Met Lys Ser Leu Ser Phe Ser Leu Ala Leu Gly Phe Gly Ser Thr Leu
1               5                   10                  15

Val Tyr Ser Ala Pro Ser Pro Ser Ser Gly Trp Gln Ala Pro Gly Pro
                20                  25                  30

Asn Asp Val Arg Ala Pro Cys Pro Met Leu Asn Thr Leu Ala Asn His
                35                  40                  45

Gly Phe Leu Pro His Asp Gly Lys Gly Ile Thr Val Asn Lys Thr Ile
                50                  55                  60

Asp Ala Leu Gly Ser Ala Leu Asn Ile Asp Ala Asn Leu Ser Thr Leu
65                  70                  75                  80

Leu Phe Gly Phe Ala Ala Thr Thr Asn Pro Gln Pro Asn Ala Thr Phe
                85                  90                  95

Phe Asp Leu Asp His Leu Ser Arg His Asn Ile Leu Glu His Asp Ala
                100                 105                 110

Ser Leu Ser Arg Gln Asp Ser Tyr Phe Gly Pro Ala Asp Val Phe Asn
                115                 120                 125

Glu Ala Val Phe Asn Gln Thr Lys Ser Phe Trp Thr Gly Asp Ile Ile
                130                 135                 140

Asp Val Gln Met Ala Ala Asn Ala Arg Ile Val Arg Leu Leu Thr Ser
145                 150                 155                 160

Asn Leu Thr Asn Pro Glu Tyr Ser Leu Ser Asp Leu Gly Ser Ala Phe
                165                 170                 175

Ser Ile Gly Glu Ser Ala Ala Tyr Ile Gly Ile Leu Gly Asp Lys Lys
                180                 185                 190

Ser Ala Thr Val Pro Lys Ser Trp Val Glu Tyr Leu Phe Glu Asn Glu
                195                 200                 205

Arg Leu Pro Tyr Glu Leu Gly Phe Lys Arg Pro Asn Asp Pro Phe Thr
                210                 215                 220

Thr Asp Asp Leu Gly Asp Leu Ser Thr Gln Ile Ile Asn Ala Gln His
225                 230                 235                 240

Phe Pro Gln Ser Pro Gly Lys Val Glu Lys Arg Gly Ile Thr Arg Cys
```

245                 250                 255

Pro Tyr Gly Tyr His
            260

<210> SEQ ID NO 36
<211> LENGTH: 248
<212> TYPE: PRT
<213> ORGANISM: Artificial Sequence
<220> FEATURE:
<223> OTHER INFORMATION: UPO 12 variant

<400> SEQUENCE: 36

Met Lys Ser Leu Ser Phe Ser Leu Ala Leu Gly Phe Gly Ser Thr Leu
1               5                   10                  15

Val Tyr Ser Ala Pro Ser Pro Ser Ser Gly Trp Gln Ala Pro Gly Pro
            20                  25                  30

Asn Asp Val Arg Ala Pro Cys Pro Met Leu Asn Thr Leu Ala Asn His
        35                  40                  45

Gly Phe Leu Pro His Asp Gly Lys Gly Ile Thr Val Asn Lys Thr Ile
    50                  55                  60

Asp Ala Leu Gly Ser Ala Leu Asn Ile Asp Ala Asn Leu Ser Thr Leu
65                  70                  75                  80

Leu Phe Gly Phe Ala Ala Thr Thr Asn Pro Gln Pro Asn Ala Thr Phe
                85                  90                  95

Phe Asp Leu Asp His Leu Ser Arg His Asn Ile Leu Glu His Asp Ala
            100                 105                 110

Ser Leu Ser Arg Gln Asp Ser Tyr Phe Gly Pro Ala Asp Val Phe Asn
        115                 120                 125

Glu Ala Val Phe Asn Gln Thr Lys Ser Phe Trp Thr Gly Asp Ile Ile
    130                 135                 140

Asp Val Gln Met Ala Ala Asn Ala Arg Ile Val Arg Leu Leu Thr Ser
145                 150                 155                 160

Asn Leu Thr Asn Pro Glu Tyr Ser Leu Ser Leu Gly Ser Ala Phe
                165                 170                 175

Ser Ile Gly Glu Ser Ala Ala Tyr Ile Gly Ile Leu Gly Asp Lys Lys
            180                 185                 190

Ser Ala Thr Val Pro Lys Ser Trp Val Glu Tyr Leu Phe Glu Asn Glu
        195                 200                 205

Arg Leu Pro Tyr Glu Leu Gly Phe Lys Arg Pro Asn Asp Pro Phe Thr
    210                 215                 220

Thr Asp Asp Leu Gly Asp Leu Ser Thr Gln Ile Ile Asn Ala Gln His
225                 230                 235                 240

Phe Pro Gln Ser Pro Gly Lys Val
                245

<210> SEQ ID NO 37
<211> LENGTH: 266
<212> TYPE: PRT
<213> ORGANISM: Hypoxylon

<400> SEQUENCE: 37

Met Lys Ser Val Gln Leu Ser Ala Leu Ile Ala Phe Gly Ala Lys Ala
1               5                   10                  15

Val Tyr Ser Phe Pro Ser Ala Asn Ala Pro Trp Ser Gly Pro Gly Thr
            20                  25                  30

Asp Asp Val Arg Gly Pro Cys Pro Met Leu Asn Thr Leu Ala Asn His
        35                  40                  45

```
Gly Phe Leu Pro His Ser Gly Lys Gly Ile Thr Val Asn Lys Thr Ile
            50                  55                  60

Asp Ala Leu Asn Ala Gly Leu Asn Met Glu Ala Asp Leu Ala Ala Leu
 65                  70                  75                  80

Leu Phe Asp Phe Ala Val Thr Thr Asn Pro Thr Pro Asn Ala Ser Tyr
                85                  90                  95

Phe Asp Leu Asp His Leu Thr Arg His Asn Ile Leu Glu His Asp Ala
                100                 105                 110

Ser Ile Ser Arg Gln Asp Ser Tyr Phe Gly Arg Ala Asp Ile Leu Asn
            115                 120                 125

Glu Ala Val Phe Asn Gln Thr Lys Ser Tyr Trp Thr Gly Glu Leu Val
    130                 135                 140

Asp Ile Gln Met Ala Ala Asn Ala Arg Val Ala Arg Leu Met Thr Ser
145                 150                 155                 160

Asn Leu Thr Asn Pro Glu Tyr Ser Leu Ser Asp Thr Gly Ser Val Phe
                165                 170                 175

Ser Ile Gly Glu Ser Ala Ala Tyr Val Gly Ile Leu Gly Asp Lys Val
            180                 185                 190

Ser Gly Thr Val Pro Lys Thr Trp Leu Ile Tyr Leu Phe Glu Gln Glu
    195                 200                 205

Arg Leu Pro Tyr Glu Leu Gly Phe Lys Arg Pro Val Asp Pro Phe Thr
    210                 215                 220

Glu Asp Asp Leu Phe Asn Met Ser Glu Ala Ile Arg Asp Ala Gln His
225                 230                 235                 240

Phe Pro Gln Asp Ile Gly Lys Val Thr Lys Arg Gly Asn Lys Ala Arg
                245                 250                 255

Cys Pro His Gly Tyr Cys Ile Glu Val Leu
                260                 265

<210> SEQ ID NO 38
<211> LENGTH: 250
<212> TYPE: PRT
<213> ORGANISM: Rosellinia necatrix

<400> SEQUENCE: 38

Met Lys Leu Thr Thr Leu Leu Phe Pro Ala Val Val Leu Gly Ala Ala
 1               5                  10                  15

Cys Pro Tyr Gly Thr Phe Lys Pro Glu Glu Pro Thr Asp Thr Arg Gly
                20                  25                  30

Val Cys Pro Met Leu Asn Ala Leu Ala Asn His Gly Phe Leu Pro Arg
            35                  40                  45

Asp Gly Arg Asn Ile Asn Glu Asn Gln Thr Val Thr Ala Leu Asn Asn
 50                  55                  60

Ala Leu Asn Leu Thr Pro Asp Phe Gly Arg Phe Leu Phe Thr Ala Gly
 65                  70                  75                  80

Arg Leu Ser Asn Pro Lys Pro Asn Ser Thr Thr Phe Asp Leu Asn His
                85                  90                  95

Leu Asp Arg His Asn Leu Phe Glu His Asp Gly Ser Leu Ser Arg Gln
                100                 105                 110

Asp Ala His Phe Gly Gln Trp Ser Arg Phe Asn Gln Thr Val Trp Asn
            115                 120                 125

Trp Thr Met Gln Tyr Trp Thr Gly Asp Ile Leu Asp Val Gln Met Val
    130                 135                 140

Ala Asn Gly Arg Ala Gln Arg His Thr Arg Ser Asn Leu Thr Asn Pro
```

```
                145                 150                 155                 160
        Asp Tyr Ala Leu Ser Val Val Gly Tyr Asp Phe Ser Val Ala Glu Asn
                        165                 170                 175

Ala Ala Leu Leu Ser Ile Ile Gly Asp Lys Val Thr Gln Thr Cys Pro
                        180                 185                 190

Lys Lys Phe Val Asp Tyr Leu Phe Val Asn Glu Glu Leu Pro Tyr Ser
                        195                 200                 205

Val Gly Trp Lys Lys Ser Glu Leu Pro Ile Ala Leu Glu Asp Leu Ile
                        210                 215                 220

Arg Thr Phe Arg Asp Ile Glu Leu Ala Thr Ala Phe Pro Ala Pro Pro
        225                 230                 235                 240

Pro Pro Asp Asn Ser Gly Glu Ile Phe Ala
                        245                 250

<210> SEQ ID NO 39
<211> LENGTH: 263
<212> TYPE: PRT
<213> ORGANISM: Daldinia sp. EC12

<400> SEQUENCE: 39

Met Lys Leu Thr Phe Met Ser Ser Val Val Thr Leu Gly Ser Ala Val
        1               5                   10                  15

Ala Ala Tyr Pro Thr Ser Trp Glu Ala Pro Gly Pro Asn Asp Val Arg
                        20                  25                  30

Gly Pro Cys Pro Met Leu Asn Thr Leu Ala Asn His Gly Phe Leu Pro
                        35                  40                  45

His Asp Gly Lys Asn Ile Asn Val Asn Asn Thr Ala Glu Ala Leu Ser
                        50                  55                  60

Lys Gly Leu Asn Leu Ala Trp Glu Leu Gly Val Asp Leu His Asp Phe
        65                  70                  75                  80

Ala Val Met Ala Asn Pro Gln Pro Asn Ala Thr Thr Phe Asp Leu Asp
                        85                  90                  95

His Leu Ser Arg His Asn Val Leu Glu His Asp Gly Ser Leu Ser Arg
                        100                 105                 110

Gln Asp Ala His Phe Gly Pro Pro Asp Val Phe Asn Glu Ala Val Phe
                        115                 120                 125

Asn Gln Thr Val Ser Tyr Trp Thr Gly Asp Val Val Thr Met Gln Met
                        130                 135                 140

Ala Ala Asn Ala Arg Leu Ala Arg Leu Met Thr Ser Asn Leu Thr Asn
        145                 150                 155                 160

Pro Glu Tyr Ser Leu Ser Asp Leu Gly Ser Gly Phe Ser Ile Gly Glu
                        165                 170                 175

Ser Val Val Tyr Leu Leu Val Leu Gly Asn Lys Asp Thr Ala Glu Ala
                        180                 185                 190

Pro Lys Asn Tyr Leu Glu Tyr Trp Phe Arg Asn Glu Arg Leu Pro Tyr
                        195                 200                 205

Glu Leu Gly Trp Glu Arg Pro Asn Val Ile Met Thr Gly Asp Asp Leu
                        210                 215                 220

Gly Asn Ala Met Asp Lys Leu Val Thr Leu Gln His Phe Pro Gln Ser
        225                 230                 235                 240

Pro Gly Lys Ile Thr Ser Asp Pro Glu Lys Ala Ser Ala Lys Leu Ala
                        245                 250                 255

Gly Lys Arg His Leu Phe His
                        260
```

```
<210> SEQ ID NO 40
<211> LENGTH: 265
<212> TYPE: PRT
<213> ORGANISM: Monosporascus

<400> SEQUENCE: 40

Met Lys Phe Glu Leu Ala Ala Thr Ile Leu Ala Ala Gly Thr Ala Ser
1               5                   10                  15

Ala Phe Arg Leu Lys Ala Arg Asp Thr Tyr Asp Trp His Pro Pro Ala
            20                  25                  30

Tyr Gly Asp Val Arg Gly Pro Cys Pro Met Leu Asn Thr Leu Ala Asn
        35                  40                  45

His Gly Tyr Leu Pro Arg Asn Gly Lys Asp Ile Thr Glu Asn Arg Thr
    50                  55                  60

Ile Glu Ala Leu Gly Thr Ala Leu Ser Ile Asp Ser Glu Leu Ala Gln
65                  70                  75                  80

Leu Leu Phe Glu Gln Ala Ile Thr Thr Asn Pro Ala Pro Asn Ala Thr
                85                  90                  95

Thr Phe Ser Leu Asn Asp Leu Val Arg His Asn Ile Leu Glu His Asp
            100                 105                 110

Ala Ser Leu Ser Arg Val Asp Phe Tyr Phe Gly Asn Pro Gln Pro Phe
        115                 120                 125

Asn Gln Thr Val Phe Ala Gln Thr Arg Ser Tyr Trp Thr Thr Pro Ile
    130                 135                 140

Ile Asp Val Gln Gln Ala Ala Asn Ala Arg Trp Ala Arg Val Glu Thr
145                 150                 155                 160

Ser Asn Ala Thr Asn Pro Asn Phe Thr Leu Ser Thr Leu Gly Glu Arg
                165                 170                 175

Phe Ser Tyr Gly Glu Ser Ala Ala Tyr Ile Val Ile Leu Gly Asn Lys
            180                 185                 190

Ile Thr Gly Thr Val Pro Arg Asp Trp Val Glu Tyr Leu Phe Glu Asn
        195                 200                 205

Glu Arg Leu Pro Leu Glu Ile Gly Trp Thr Arg Thr Gly Ser Ile
    210                 215                 220

Thr Arg Asn Asp Leu Glu Asp Val Met Gln Gln Ile Tyr Ala Ala Thr
225                 230                 235                 240

Pro Asn Asn Asn Ala Thr Thr Asn Ser Trp Arg Gly Asn Pro Arg Ala
                245                 250                 255

Leu His Met Ala Val Arg Ala Ser Ala
            260                 265

<210> SEQ ID NO 41
<211> LENGTH: 273
<212> TYPE: PRT
<213> ORGANISM: Aspergillus aculeatus

<400> SEQUENCE: 41

Met Arg Tyr Phe Val Leu Ala Cys Ala Pro Leu Leu Tyr Ala Val Thr
1               5                   10                  15

Leu Ala Phe Pro Arg Ala Asp Tyr Val Ser Glu Gly Lys Leu Pro Ala
            20                  25                  30

Gly His Pro Pro Leu Asp Trp Lys Pro Ala Gly Leu Gly Asp Ala Arg
        35                  40                  45

Ala Pro Cys Pro Met Leu Asn Thr Leu Ala Asn His Gly Tyr Leu Pro
    50                  55                  60
```

```
His Asp Gly Lys Asp Ile Thr Lys Ala His Thr Ile Ala Ala Leu His
65                  70                  75                  80

Ser Ala Leu Asn Ile Asp Arg Glu Leu Ala Gln Tyr Leu Phe Gln Glu
                85                  90                  95

Ala Leu Thr Thr Asn Pro Ala Ala Asn Ala Thr Thr Phe Ser Leu Asn
            100                 105                 110

Asp Leu Ser Arg His Asn Ile Leu Glu His Asp Ala Ser Leu Ser Arg
        115                 120                 125

Leu Asp Tyr Tyr Phe Gly Asp Asn His Asp Phe Asn Gln Ala Ile Phe
        130                 135                 140

Asp Gln Thr Arg Gln His Trp Pro Asp Pro Ile Ile Thr Val Gln Ala
145                 150                 155                 160

Ala Ala Asn Ala Arg Glu Ala Arg Val Arg Thr Ser Asn Ala Thr Asn
                165                 170                 175

Pro Thr Phe Thr Leu Ser Glu Leu Gly Thr Ala Phe Gly Tyr Gly Glu
            180                 185                 190

Thr Ala Ala Tyr Ile Ile Ile Leu Gly Asn Lys Thr Ser Gly Leu Val
        195                 200                 205

Asp Arg Ser Trp Val Glu Tyr Leu Phe Glu Asn Glu Arg Leu Pro Val
        210                 215                 220

Glu Leu Gly Trp Thr Arg His Glu Glu Ala Val Ser Met Asp Asp Leu
225                 230                 235                 240

Glu Gly Met Met Gln Glu Val Ile Asn Ala Thr Gly His Ala Glu Glu
                245                 250                 255

Val Lys Arg Glu Leu Val Arg Arg Gly Asp Leu His Val Gly Arg Arg
            260                 265                 270

Ala
```